(12) United States Patent
Mazeaud et al.

(10) Patent No.: US 8,834,853 B2
(45) Date of Patent: Sep. 16, 2014

US008834853B2

(54) COATED DEHYDRATED MICROORGANISMS WITH ENHANCED STABILITY AND VIABILITY

(75) Inventors: Isabelle Mazeaud, Chatellerault (FR); Kathryn Tse, Valby (DK); Jean-Philippe Obert, Chatellerault (FR); Claudette Berger, Mennecy (FR); Geoffrey Babin, Noyant de Touraine (FR); Patrick Chaigneau, Chatellerault (FR); Hans Hedegaard Jensen, Horsens (DK); Erwan Henri, Les Ormes (FR)

(73) Assignee: DuPont Nutrition Bioscience Aps, Copenhagen (DK)

( * ) Notice: Subject to any disclaimer, the term of this patent is extended or adjusted under 35 U.S.C. 154(b) by 54 days.

(21) Appl. No.: 13/388,392

(22) PCT Filed: Aug. 13, 2010

(86) PCT No.: PCT/EP2010/061819
§ 371 (c)(1),
(2), (4) Date: Feb. 1, 2012

(87) PCT Pub. No.: WO2011/018509
PCT Pub. Date: Feb. 17, 2011

(65) Prior Publication Data
US 2012/0142531 A1 Jun. 7, 2012

Related U.S. Application Data

(60) Provisional application No. 61/233,899, filed on Aug. 14, 2009, provisional application No. 61/331,918, filed on May 6, 2010.

(51) Int. Cl.
| | | |
|---|---|---|
| A01N 63/00 | (2006.01) |
| A61K 39/02 | (2006.01) |
| A61K 45/00 | (2006.01) |
| A23L 1/03 | (2006.01) |
| A23L 1/00 | (2006.01) |
| C12N 1/04 | (2006.01) |
| A23K 1/00 | (2006.01) |
| A23L 1/30 | (2006.01) |

(52) U.S. Cl.
CPC ............... *C12N 1/04* (2013.01); *A23L 1/0345* (2013.01); *A23L 1/0029* (2013.01); *A23K 1/009* (2013.01); *A23L 1/3014* (2013.01)

USPC .......... 424/50; 424/93.1; 424/93.3; 424/93.4; 424/234.1; 424/282.1; 504/117

(58) Field of Classification Search
None
See application file for complete search history.

(56) References Cited

U.S. PATENT DOCUMENTS

| | | | | |
|---|---|---|---|---|
| 4,956,295 | A | * | 9/1990 | Sudoma .................... 435/252.1 |
| 5,275,943 | A | * | 1/1994 | DiTuro ........................ 435/179 |
| 6,365,148 | B1 | | 4/2002 | Kim et al. |
| 6,919,172 | B2 | | 7/2005 | DePablo et al. |
| 7,157,258 | B2 | | 1/2007 | Durand et al. |
| 2010/0303962 | A1 | * | 12/2010 | Penhasi et al. ................. 426/61 |

FOREIGN PATENT DOCUMENTS

| | | |
|---|---|---|
| DE | 3432394 | 1/1986 |
| EP | 0778778 | 3/2002 |
| EP | 1514553 | 3/2005 |
| EP | 1753440 | 2/2008 |
| WO | 2008/035332 | 3/2008 |

OTHER PUBLICATIONS

International Search Report and Written Opinion in PCT/EP2010/061819, dated Nov. 5, 2010.

* cited by examiner

*Primary Examiner* — Alton Pryor
(74) *Attorney, Agent, or Firm* — McAndrews, Held & Malloy Ltd.

(57) ABSTRACT

The present invention relates to coated dehydrated microorganisms comprising a dehydrated microorganism surrounded by at least one coating, said coating comprising by dry weight at least 25% of hygroscopic salt(s) and wherein the pH of the coating is compatible with viability of the coated dehydrated microorganism. The coating can be partially crystalline, the salt(s) in the coating having preferably a crystallinity degree of up to 60% once applied onto the dehydrated microorganism. The present invention also relates to liquid coating compositions, methods for coating and protecting a dehydrated microorganism. Finally, the present invention relates to a method for the preparation of food products, feed products, consumer healthcare products or agri-products as well as to a food product, feed product, a consumer healthcare product or an agri-product containing such coated dehydrated microorgansims.

30 Claims, 16 Drawing Sheets

COATED DEHYDRATED MICROORGANISMS WITH ENHANCED STABILITY AND VIABILITY

The present application is filed pursuant to 35 U.S.C. 371 as a U.S. National Phase application of International Patent Application No. PCT/EP2010/061819, which was filed Aug. 13, 2010, claiming the benefit of priority to U.S. Provisional Patent Application No. 61/331,918, which was filed on May 6, 2010, and U.S. Provisional Patent Application No. 61/233,899, which was filed on Aug. 14, 2009. The entire text of the aforementioned applications is incorporated herein by reference in its entirety.

FIELD OF THE INVENTION

The present invention relates to coated dehydrated microorganisms having enhanced stability and viability.

BACKGROUND OF THE INVENTION

Freeze-drying processes are frequently used to preserve microorganisms. Indeed, the low operating temperatures of freeze-drying processes lead to minimal damage in microorganisms. Moreover, it is known in the art that low storage temperatures can be an essential element in maintaining the viability and stability of such freeze-dried cells. It is also known in the art, that cells which are freeze-dried in the presence of protective agents are better suited to maintain their viability and stability than cells which are freeze-dried without the addition of said protective agents. For example, U.S. Pat. No. 6,919,172 (Wisconsin Alumni Research Foundation) relates to the use of a protective mixture (i.e. sucrose and potassium phosphates) mixed with biological material in order to form a preservation medium, prior to the biological medium undergoing at least one preservation process (eg. freezing, freeze-drying, vacuum-drying or spray-drying). After being subjected to a preservation process, the biological material is capable of remaining stable when stored in dry conditions at room temperature. However, the probiotic microorganisms of U.S. Pat. No. 6,919,172 which have been preserved to provide increased stability during shipping and storage in sealed containers cannot usually withstand the simultaneous high temperature and/or high humidity conditions which are typically encountered in long-term storage and secondary processes used in feed products, food products (e.g. cereals, nutritional bars, recombined cheese, infant formulas), consumer healthcare products (including dietary supplements, nutraceuticals, over-the-counter products) as well as agri-products. Indeed, the viable microoganisms are often inactivated by heat and/or moisture and/or other processing conditions or storage conditions, thereby decreasing their viability in the final product over time, during storage and/or during consumption, in such a way that the desired effect of the final product containing the microorganisms is eventually lost.

In order to overcome this problem, numerous coating processes for microorganisms have been developed to protect them against undesirable elements such as high temperature and high humidity levels. These coating processes are often based on coating materials such as fats or low permeability polymers such as shellac and hydroxypropylmethyl cellulose (HPMC). For example, U.S. Pat. No. 7,157,258 (Lallemand) deals with coating of dehydrated microorganisms by using hydrophobic barriers such as fat and waxes with melting points greater than 60° C., while EP 1753440 B1 (Merck), U.S. Pat. No. 6,365,148 (Il Yang Pharm Co. Ltd.) and EP 0778778 B1 (University New South Wales) use polymeric barriers such as HPMC or starch. These moisture barriers are intended to provide protection of the dehydrated microorganisms by preventing or delaying penetration of water into the coating, thereby avoiding diffusion of moisture to the underlaying dehydrated microorganism. If the coating allows moisture to pass, then the dehydrated microorganism may absorb moisture, thereby altering its viability.

However, the Applicant has prepared dehydrated microorganisms coated with commonly used compounds such as fats, shellac or HPMC and noticed that the viability of such microorganisms containing products was not sufficiently maintained. Indeed, as can be seen in the results section of the present patent application (especially Example 4, Table 5 and Example 7, Table 8), the materials used in the prior art to coat the microorganisms do not enhance the thermostability of the microorganisms nor provide enhanced viability over a longer period of time in medium or high humidity environments when compared to non-coated dehydrated microorganisms.

Consequently, despite the teachings above, there still exists a need in the art for coated dehydrated microorganisms, whereby the microorganisms are able to retain most of their activity during and after manufacturing and are able to resist the damaging conditions encountered for example in secondary processes used for the preparation of feed/food products, consumer healthcare products or agri-products or during long term storage of these products, wherein said processes/long term storage often involve a combination of high temperature and/or high moisture, thereby responding to a widely sought-after and currently unmet demand for dehydrated microorganisms with improved stability.

SUMMARY OF THE INVENTION

The Applicant has surprisingly found that the addition of at least one hygroscopic salt layer surrounding the dehydrated microorganisms enhances the survival rate (i.e. viability) of these dehydrated microorganisms, especially in high humidity and/or high temperature conditions. Indeed, whereas the skilled man typically uses hydrophobic (e.g. fats), low permeability compounds (e.g. shellac or HPMC) or non-hygroscopic salt(s) as coatings in order to prevent moisture uptake, the Applicant surprisingly has found that at least one coating comprising hygroscopic salt(s) enables processing and storage of dehydrated microorganisms in conditions involving high humidity and/or high temperature without altering microorganisms viability.

The invention thus particularly relates to a coated dehydrated microorganism comprising a dehydrated microorganism surrounded by at least one coating, said coating comprising by dry weight at least 25% of hygroscopic salt or mixture thereof as hereafter defined, and wherein the pH of the coating is compatible with viability of the coated dehydrated microorganism. The "at least one coating" of the present invention is therefore an "at least one hygroscopic salt coating".

The coating can also comprise by dry weight 0 to 60% of at least one non hygroscopic salt.

Optionally, other ingredients can be included into the coating, such as polyhydroxy compounds, anti-sticking agents, compounds having health and/or nutritional benefits (anti-oxidants, vitamins, minerals, prebiotics, peptides, proteins, . . . ), hydrocolloids, fillers, lubricants, binders, acids, alkali, hydrophobic species, polymers, and mixtures thereof. These other optional ingredients are preferably in a quantity by dry weight of 0 to 70%.

The invention thus particularly relates to a coated dehydrated microorganism comprising a dehydrated microorganism surrounded by at least one coating, said coating comprising by dry weight:

at least 25% of a hygroscopic salt or mixture thereof,
    0 to 60% of a non hygroscopic salt or mixture thereof,
    0 to 70% of other optional ingredient(s)

and wherein the pH of the coating is compatible with viability of the coated dehydrated microorganism.

One or more layers of hygroscopic salt coating according to the present invention (respectively named "1$^{st}$ hygroscopic salt coating", "2$^{nd}$ hygroscopic salt coating"... ) can be used to coat the dehydrated microorganism, with the same or a different composition. The invention thus particularly relates to a coated dehydrated microorganism comprising a dehydrated microorganism surrounded by at least one coating, or at least two, or at least three or or at least four coatings as defined according to the invention. One or more outer coating layers surrounding the hygroscopic salt coating(s) (respectively named "1$^{st}$ outer coating layer", "2$^{nd}$ outer coating layer... ") can also be added. These optional outer coating layers can comprise conventional compounds such as fats; fatty acids (e.g. stearic acid); emulsifiers (such as mono and di-glycerides); oils; waxes; resins; low permeability polymers (e.g. shellac, sepifilm, polyvinyl pyrolidone, poly ethylene glycol); hydrocolloids (e.g. carrageenan, alginates or gum arabic or xanthan gum or guar gum); starches which may be used as native or modified starches derived from potatoes, corn, whey, rice, potatoe, tapioca; cyclodextrines; polyols (e.g. mannitol); cellulose and cellulose derivatives (HPMC, cellulose esters, cellulose ethers) and mixtures thereof.

The outer coating layers may be used to provide further resistance to the dehydrated microorganism, particularly to protect against inactivation by gastric and/or oxidative environments and/or conditions with unfavourable pH. These layers can also provide enhanced mechanical resistance, enhanced resistance to steam treatment or enhanced handling properties (e.g., improved solids flow) to the coated dehydrated microorganism.

It has been shown that the coating of the invention provides enhanced resistance to inactivation during secondary processes used for the preparation of food, feed, consumer healthcare products or agri-products and/or provides long term shelf-life stability required in food, feed, consumer healthcare products and agri-products. Consequently, the coated dehydrated microorganism according to the present invention can be employed in functional foods, feed products, consumer healthcare products and agri-products. This new technology is expected to increase sales of key dehydrated microorganisms, particularly key probiotic microorganisms and direct fed microbials, as it is responding to a sought-after market demand for enabling the use of dehydrated microorganisms in new applications such as food, feed, consumer healthcare products and agri-products where current commercial freeze-dried microorganisms lack long-term and processing stability.

All cited references are incorporated by reference.

DEFINITIONS

The term "coating" used in the present invention means any layer (or coating layer) surrounding the dehydrated microorganism once the liquid coating composition is applied and dried.

The quantity of ingredient(s) of the coating is expressed in percentage, which is a percentage by dry weight (wt % dry) and related to the coating layer itself (and not to the coated dehydrated microorganism). The percentages are inclusive of any bound waters of crystallization.

In the present invention, the term "salt(s)" also encompasses salt hydrates. So hygroscopic salt(s) include hygroscopic salt hydrates and non hygroscopic salt(s) include non hygroscopic salt hydrates.

The expression "at least 25% of hygroscopic salt(s)" is synonymous with the expression "at least 25% of a hygroscopic salt or mixture thereof". It means either:

at least 25% of a single hygroscopic salt; or
    at least 25% of a mixture of several hygroscopic salts (for example at least 20% of a first hygroscopic salt+at least 5% of another hygroscopic salt).

The same interpretation shall be made with the other preferred percentages later mentioned in the application.

"Hygroscopicity is the tendency of a substance to absorb moisture from the air". Hygroscopic reads "(of a substance) tending to absorb moisture from the air" (Oxford English Dictionary).

Hygroscopicity can be characterized by these two parameters: (a) the Moisture Holding Capacity (MHC) and (b) the Moisture Uptake Rate (MUR).

Hygroscopicity can be defined as the relative amount of water a material can absorb. Accordingly, the Moisture Holding Capacity (MHC) is the equilibrium amount of water a material can absorb when exposed to a given relative humidity. "Relative humidity of air (RH) is the ratio of the partial pressure of water vapour to its vapour pressure at that temperature" (Atkins, Physical Chemistry, OUP, 1978, p 199). In the present application, Moisture Holding Capacity (MHC) refers to the equilibrium quantity of moisture absorbed by the coating or by the coated dehydrated microorganism, on a gravimetric basis, when exposed to an environment of controlled relative humidity. It can be measured by recording the weight gain of the coating or of the coated dehydrated microorganism, until no further weight gain is observed.

MHC can be expressed either volumetrically (in units of mg/cm$^3$) or gravimetrically (in weight percent (% w/w)), on the basis of the starting material prior to being exposed to humidity. It is important to note that MHC may dependent on the amount of exposed surface area and the thickness of a material. MHC can be further analyzed according to the formula described by Sharma and Patel, "study and evaluation of hygroscopic behaviour of phosphatic fertilizers" IFA Technical Conference, 1-4 Oct. 2000, New Orleans, La., USA:

$$MHC=MA/MP, \text{ where:}$$

MA=moisture absorption, (mg/cm$^2$), a measure of how much moisture is taken up into a given surface area of the material (mg/cm$^2$); and MP=moisture penentration (cm), a measure of the depth of moisture penetration.

(b) The Moisture Uptake Rate (MUR):

The hygroscopicity of a salt can be measured by the MUR ("Additive to biological substances. III. The moisture content and moisture uptake of commonly used carrier agents undergoing processing conditions similar to those used in the preparation of international biological standards", E Tarelli and al., Journal of Biological Standardization, 1987, 15, 331-340). There is also a kinetic dimension to hygroscopicity. The Moisture Uptake Rate (MUR) is the MHC per unit time, measured for a given % RH, at a given temperature and for a given time period, measured in hours or days. In the present invention, a salt having a MUR of at least 20% w/w at 25° C. at 75% RH after 7 days will be considered as a hygroscopic salt and a salt having a MUR of less than 20% w/w at 25° C. at 75% RH after 7 days will be considered as a non hygroscopic salt. A detailed protocol for MUR determination with data is given in example 9. It has to be understood that the MUR and therefore the hygroscopic or non hygroscopic nature of a salt depends upon the atmospheric conditions (especially the temperature or the % RH) under which it is measured. The definition of a hygroscopic or non hygroscopic salt provided in this application is limited to the following specific conditions: after storage of the salt at 25° C. and at 75% RH for 7 days. For example in the literature sodium sulphate is sometimes cited as a hygroscopic salt and at others times as a non hygroscopic salt, depending on the ambient humidity and temperature. In the present invention, it is classified as a non hygroscopic salt because its MUR was measured at 25° C. at 75% RH after 7 days and was less than 20% w/w. In other literature or patents, it could be considered as hygroscopic for example when the MUR is measured at higher % RH.

So as used in the present invention, a hygroscopic salt has to be understood as an inorganic or an organic salt (salt hydrates being encompassed) with a MUR of at least 20% w/w at 25° C. at 75% RH after 7 days. The degree of hygroscopicity varies considerably amongst hygroscopic salts (that is to say that some salts are very hygroscopic in comparison with some others).

Preferably the hygroscopic salt according to the invention has a MUR of at least 30% w/w at 25° C. at 75% RH after 7 days, more preferably a MUR of at least 40% w/w at 25° C. at 75% RH after 7 days, more preferably a MUR of at least 50% w/w at 25° C. at 75% RH after 7 days and even more preferably a MUR of at least 60% w/w at 25° C. at 75% RH after 7 days.

Some examples of hygroscopic salts according to the invention are dipotassium phosphate ($K_2HPO_4$), disodium hydrogen phosphate anhydrous ($Na_2HPO_4$), sodium hexametaphosphate ($NaPO_3)_6$, sodium acetate anhydrous ($CH_3COONa$), magnesium nitrate ($Mg(NO_3)_2$), calcium bromide ($CaBr$), lithium bromide ($LiBr$), calcium chloride ($CaCl_2$), magnesium chloride ($MgCl_2$), lithium chloride ($LiCl$), phosphorus pentoxide ($P_4O_{10}$), disodium hydrogen phosphate dihydrate ($Na_2HPO_4$-$2H_2O$), disodium hydrogen phosphate heptahydrate ($Na_2HPO_4$-$7H_2O$), ammonium acetate ($CH_3COONH_3$), calcium acetate ($CH3COO)_2Ca$, potassium acetate ($CH_3COOK$), potassium carbonate ($K_2CO_3$), sodium carbonate ($Na_2CO_3$), sodium formate ($NaCHO_2$), potassium citrate monohydrate ($K_3C_6H_5O_7$.$H_2O$), Sodium citrate pentahydrate ($C_6H_5Na_3O_7$. $5H_2O$) and mixtures thereof.

For example:
$K_2HPO_4$ has a MUR of 45.6% w/w at 25° C. at 75% RH after 7 days,
$K_2CO_3$ has a MUR of 50.7% w/w at 25° C. at 75% RH after 7 days,
$MgCl_2$ has a MUR of 53.7% w/w at 25° C. at 75% RH after 7 days.

In addition, the expression "hygroscopic salt or mixture thereof" encompasses the two following aspects:
(a) the salt(s) is/are initially hygroscopic (per se), that is to say that before being applied onto the dehydrated coated micororganism, it/they has/have a MUR of at least 20% w/w at 25° C. at 75% RH after 7 days; and/or:
(b) one or more of the salt(s) is/are not initially hygroscopic but it/they become(s) hygroscopic once applied onto the dehydrated microorganism (i.e. once processed). In other words, before being applied onto the dehydrated, it/they has/have not a MUR of at least 20% w/w at 25° C. at 75% RH after 7 days but it/they has/have a MUR of at least 20% w/w at 25° C. at 75% RH after 7 days once the coating is applied onto the microorganism. By way of example, it has been surprisingly shown in sample 28 that the addition of a certain amount of NaOH to a non hygroscopic salt such as $KH_2PO_4$ provides a suitable coating containing hygroscopic salt coming from the reaction $KH_2PO_4$ with NaOH (alteration of the non-hygroscopic nature of this salt, leading to a hygroscopic one).

So the hygroscopic salt(s) is(are) a hygroscopic salt per se and/or becomes a hygroscopic salt after being applied onto the dehydrated microorganisms.

In addition, the material itself, the temperature, the humidity and drying conditions under which the coating is applied will influence "the degree of hydration" of the coating and thereby the hygroscopicity of the salts(s) in the coating.

As used herein, a non-hygroscopic salt according to the invention is an organic or an inorganic salt (salt hydrates being encompassed) with a MUR at 25° C. and 75% RH after 7 days of less than 20% w/w. Preferably a non-hygroscopic salt according to the invention has a MUR of less than 10%, more preferably of less than 5% w/w at 25° C. at 75% RH after 7 days.

Examples of non hygroscopic salts according to the invention are monopotassium phosphate ($KH_2PO_4$), sodium acetate tri hydrate ($CH_3COONa.3H_2O$), calcium sulphate dihydrate ($CaSO_3.2H_2O$), sodium sulphate ($Na_2SO_4$), magnesium sulphate ($MgSO_4$), potassium sulphate ($K_2SO_4$), sodium chloride (NaCl), potassium chloride (KCl), calcium carbonate (CaCO3), calcium lactate (($CH_3CHOHCOO)_2Ca$), calcium citrate tetrahydrate (($Ca_3C_6H_5O_7)_2.4H_2O$), sodium citrate dihydrate ($HOC(COONa)(CH_2COONa)_2.2H_2O$), and mixtures thereof.

In the present application, a pH of the coating "compatible with viability of the coated dehydrated microorganism" means that the pH is chosen in such a way that it does not alter the microorganism viability. It varies upon strains but it should generally be between 5.5 and 7.9, preferably between 6 and 7.5. In the meaning of the present invention, this pH refers to the pH measured after the coated dehydrated microorganism of the present invention is suspended in water in an amount of 10 wt %.

In the present application, "final products" refer to food products, feed products, consumer healthcare products or agri-products incorporating the coated dehydrated microorganisms of the present invention.

DETAILED DESCRIPTION OF THE INVENTION

The inventors have surprisingly found that presence in the coating of particular salts, i.e. hygroscopic salt(s), in a sufficient amount, leads to an increase in viability of the coated dehydrated microorganism. Without wishing to be bound by theory, the inventors surmise that the microorganism stabilizing effect obtained with the coating is dependent on the ability of the coating to absorb moisture, which is directly related to the presence of hygroscopic salt(s) that readily absorb(s) moisture. In addition, when processed to coat the dehydrated microorganisms, the hygroscopic salt layer comprising such hygroscopic salt(s) may take the form of an amorphous or partially amorphous (semi-crystalline) state, which allows for enhanced diffusion of moisture and/or a higher amount of moisture absorption into the coating bulk phase. The inventors have shown that when the coating is amorphous or not fully crystalline once processed (i.e. applied onto the dehydrated microorganisms), its capacity to absorb moisture and/or its rate of moisture absorption is/are significantly greater and surprisingly the viability is enhanced compared to coatings showing low hygroscopicity.

The invention thus particularly relates to a coated dehydrated microorganism comprising a dehydrated microorganism surrounded by at least one coating, said coating comprising by dry weight at least 25% of hygroscopic salt or mixture thereof, and wherein the pH of the coating is compatible with viability of the coated dehydrated microorganism.

The invention is also about a coated dehydrated microorganism consisting of a dehydrated microorganism surrounded by at least one coating, said coating comprising by dry weight at least 25% of hygroscopic salt or mixture thereof, and wherein the pH of the coating is compatible with viability of the coated dehydrated microorganism.

The coating contains preferably at least 28% by dry weight of a hygroscopic salt or mixture of hygroscopic salts, more preferably at least 30%, more preferably at least 40%, more preferably at least 50%, more preferably at least 60%, more preferably at least 70%, more preferably at least 80%, of a hygroscopic salt or mixture of hygroscopic salts.

In a specific embodiment the coating consists of 100% by dry weight of a hygroscopic salt or mixture of hygroscopic salts.

In one embodiment, the hygroscopic salt(s) of the coating according to the invention is(are) selected from the group comprising or consisting of dipotassium phosphate ($K_2HPO_4$), disodium hydrogen phosphate anhydrous ($Na_2HPO_4$), sodium hexametaphosphate ($NaPO_3)_6$, sodium acetate anhydrous ($CH_3COONa$), magnesium nitrate ($Mg(NO_3)_2$), calcium bromide ($CaBr$), lithium bromide ($LiBr$), calcium chloride ($CaCl_2$), magnesium chloride ($MgCl_2$), lithium chloride ($LiCl$), phosphorus pentoxide ($P_4O_{10}$), disodium hydrogen phosphate dihydrate ($Na_2HPO_4 \cdot 2H_2O$), disodium hydrogen phosphate heptahydrate ($Na_2HPO_4 \cdot 7H_2O$), ammonium acetate ($CH_3COONH_3$), calcium acetate ($CH3COO)_2Ca$, potassium acetate ($CH_3COOK$), potassium carbonate ($K_2CO_3$), sodium carbonate ($Na_2CO_3$), sodium formate ($NaCHO_2$), potassium citrate monohydrate ($K_3C_6H_5O_7 \cdot H_2O$), Sodium citrate pentahydrate ($C_6H_5Na_3O_7 \cdot 5H_2O$) and mixture thereof.

Magnesium chloride ($MgCl_2$) and dipotassium phosphate ($K_2HPO_4$) are the preferred hygroscopic salts, dipotassium phosphate ($K_2HPO_4$) being the most preferred one. Therefore in a particular embodiment, the dehydrated microorganism is surrounded by at least one coating, said coating comprising $K_2HPO_4$ as hygroscopic salt or comprising a mixture of hygroscopic salts including $K_2HPO_4$.

In a particular embodiment, the dehydrated microorganism is surrounded by at least one coating comprising $MgCl_2$. In a particular embodiment, the dehydrated microorganism is surrounded by at least one coating consisting of $MgCl_2$ (sample 25 of table 1).

In a particular embodiment, the coating comprises a mixture of at least two hygroscopic salts.

It is important that the pH of the coating is compatible with viability of the coated dehydrated microorganism. Suitable pH for coating the dehydrated microorganism according to the present invention can be obtained by several means. The pH of the coating can be readily compatible with microorganism viability, depending on the nature of the compounds chosen to prepare the coating according to the invention. For example the preparation of a coating consisting of a neutral hygroscopic salt allows getting a suitable pH. In that case there is no need to adjust the pH of the coating.

A compatible pH can be obtained by adequately combining compounds of the coating, as some materials are more acid than others.

Alternatively, the pH can be modulated by the addition of standard alkali (e.g. NaOH, KOH) or acids (e.g. lactic acid) to the coating solution. By way of example, one who is intended to prepare a coating comprising $K_2HPO_4$ as hygroscopic salt can add an acid such as lactic acid, to reduce the pH of the resulting coating, as $K_2HPO_4$ is a slightly basic salt. He can also prepare a mixture adding a certain amount of $KH_2PO_4$ to $K_2HPO_4$ to reduce the pH of the resulting coating, (because of the acidic nature of $KH_2PO_4$).

Therefore in a particular embodiment, the dehydrated microorganisms are surrounded by at least one coating comprising at least $K_2HPO_4$ and at least an acid. In another particular embodiment the coating comprises at least $K_2HPO_4$ and $KH_2PO_4$.

A pH compatible with the viability of the coated dehydrated microorganism varies upon strains but it should generally be between 5.5 to 7.9, preferably between 6 to 7.5. In view of its composition, the coating of the present invention has a pH value which is suitable for enhancing the microorganism viability during application of the coating onto the dehydrated micoorganisms, during storage of the coated dehydrated microorganisms in dry conditions, during incorporation and storage of the coated dehydrated microorganisms in finished products and following rehydration of the microorganisms. Typically, the coated dehydrated microorganism according to the invention provides a solution/suspension having a pH of from 5.5 to 7.9, preferably from 6 to 7.5, when redissolved/resuspended in water in an amount of 10 wt %.

The coating can also comprise by dry weight 0 to 60% of a non hygroscopic salt or mixture thereof. In a particular embodiment the coating contains from 5% to 60%, preferably from 10% to 60%, preferably from 15% to 50%, and more preferably from 20 to 35% of a non hygroscopic salt or mixture thereof. In a particular embodiment the coating contains less than 50%, or less than 40%, or less than 30%, or less than 20%, or less than 10% or less than 5% of a non hygroscopic salt or mixture thereof.

In one embodiment, the non-hygroscopic salt(s) of the coating according to the invention is(are) selected from the group comprising or consisting of monopotassium phosphate ($KH_2PO_4$), sodium acetate tri hydrate ($CH3COONa \cdot 3H_2O$), calcium sulphate dihydrate ($CaSO_3 \cdot 2H_2O$), sodium sulphate ($Na_2SO_4$), magnesium sulphate ($MgSO_4$), potassium sulphate ($K_2SO_4$), sodium chloride ($NaCl$), potassium chloride ($KCl$), calcium carbonate ($CaCO3$), calcium lactate (($CH_3CHOHCOO)_2Ca$), calcium citrate tetrahydrate (($Ca_3C_6H_5O_7)_2 \cdot 4H_2O$), sodium citrate dihydrate ($HOC(COONa)(CH_2COONa)_2 \cdot 2H_2O$), and mixtures thereof, monopotassium phosphate ($KH_2PO_4$) being the most preferred non-hygroscopic salt(s).

In one embodiment the coating comprises monopotassium phosphate ($KH_2PO_4$).

In a particular embodiment, the coating according to the invention comprises a mixture of at least one hygroscopic salt with at least one non hygroscopic salt. In a particular embodiment, the dehydrated microorganism is surrounded by at least one coating comprising dipotassium phosphate ($K_2HPO_4$) and monopotassium phosphate ($KH_2PO_4$). In a specific embodiment, the dehydrated microorganism is surrounded by at least one coating consisting of dipotassium phosphate ($K_2HPO_4$) and monopotassium phosphate ($KH_2PO_4$). In a particular embodiment, the coating comprises dipotassium phosphate ($K_2HPO_4$) and sodium acetate tri hydrate ($CH_3COONa \cdot 3H_2O$). Their ratio can be from 1:99 to 99:1. They can be present under an equimolar ratio.

Optionally other ingredients can be included into the coating, such as polyhydroxy compounds, anti-sticking agents, compounds having health and/or nutritional benefits (anti-oxidants, vitamins, minerals, prebiotics, peptides, proteins . . . ), hydrocolloids, fillers, lubricants, binders, acids, alkali, hydrophobic species, polymers, and mixtures thereof. These other optional ingredients are preferably in a quantity by dry weight of 0 to 70%, more preferably from 10% to 60%, even more preferably from 17 to 40%.

These optional ingredients can be used to improve processability of the coating (i.e. applied onto the dehydrated microorganism). For example talc or starches (whey starch, rice starch) are inert ingredients that could be used as anti-sticking agent of the coating. These optional ingredients can also be used to bring an additional benefit/effect into the final product (e.g. vitamin supplementation). They can also be used to adjust the pH of the coating to a value that is "compatible with the viability of the coated dehydrated microorganism".

The "polyhydroxy compound(s)" is(are) typically selected from the group comprising saccharides, carbohydrates, polyalcohols (or polyols), derivatives thereof and mixtures thereof. Mannitol can be cited as an example of polyoalcohols. Saccharides can be natural and synthetic monosaccharides and polysaccharides. Polysaccharides refer to saccharides containing two or more monosaccharide units. Starch and modified starches can be cited as example of polysaccharides.

The individual polyhydroxy compounds can be used alone, or in combination with other types of polyhydroxy compounds. From the wide variety of useful polyhydroxy compounds, the use of monosaccharides and polysaccharides, or starch hydrolysate products such as dextrines and mixture thereof is preferred. Disaccharides, such as maltose, lactose, and sucrose are preferred for use in the present invention, with sucrose being most preferred.

"Anti-sticking agents" (also called "anti-caking agents" or "anti-agglomeration agents") that can be used in accordance with the present invention include talc, silica (precipitated or fumed silicas), starches (including native starches derived from potatoes, corn, whey, rice, tapioca). Talc and rice starch are one of the most preferred agents.

The coating according to the present invention can contain compounds having health and/or nutritional beneficts such as anti-oxidants, vitamins, minerals, prebiotics, peptides, proteins . . . .

Typically, "anti-oxidants" which may be comprised in the coating according to the invention can be chosen from the group comprising monosodium glutamate, ascorbic acid (Vitamin C), lactobionic acid, tertiary butyl hydroquinone, gluthathione, propyl gallate, ascorbyl palmitate, alfa-tocopherol (Vitamin E), polyphenols, catalase, glucose oxydase, EDTA.

"Prebiotic" is defined as a non-digestible food ingredient that beneficially affects the host by selectively stimulating the growth and/or the activity of one or a limited number of beneficial bacteria. Prebiotics are typically non-digestible carbohydrates (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and transgalacto-oligosaccharides (GOS or TOS). Other suitable prebiotics include palatinoseoligosaccharides, soybean oligosaccharides, gentiooligosaccharides, xylooligomers, non-degradable starches, lactosaccharose, lactulose, lactitol, maltitol, polydextrose (i.e. Litesse®) or the like.

Typically, "peptides" are compounds comprising generally less than 50 amino acids. Peptides can be either oligopeptides (10 amino acids or less) or polypeptides (more than 10 amino acids).

"Proteins" are compounds comprising generally more than 100 amino acids. As examples of proteins we can cite film-forming proteins, such as whey protein, caseinate, casein, globulin. In a particular embodiment, the proteins are non-enzymatic proteins.

Typically, "fillers" which may be comprised in the coating according to the invention are selected from the group comprising of talc, silica (precipitated or fumed silicas).

Typically "acids" and "alkali" can be added especially to obtain a pH compatible with the viability of the coated dehydrated microorganism of the present invention. From the wide variety of acids and alkali that could be used, lactic acid, sodium hydroxide and ammonium hydroxide are preferred.

Typically, "lubricants" which may be comprised in the coating according to the invention are selected from the group comprising magnesium stearate, propylene glycol.

Typically, examples of "hydrocolloids" which may be comprised in the coating according to the invention are carrageenans, alginates or gum arabic or Xanthan gum, guar gum.

Typically, "binders" which may be comprised in the coating according to the invention can be matodextrine for example.

Typically, "hydrophobic species" which may be comprised in the coating according to the invention can be chosen from the group comprising fats, fatty acids, emulsifiers such as mono and di-glycerides, oils, waxes . . . .

Typically, some examples of "polymers" which may be comprised in the coating according to the invention are starches which may be used as native or modified starches derived from potatoes, corn, whey, rice, potatoe, tapioca; cyclodextrines, cellulose and cellulose derivatives (cellulose ester, cellulose ethers); low permeability polymers (e.g. shellac, HPMC, polyvinyl pyrolidone, poly ethylene glycol).

In a particular embodiment the invention thus particularly relates to a coated dehydrated microorganism comprising a dehydrated microorganism surrounded by at least one coating, said coating comprising by dry weight:
at least 25% of a hygroscopic salt or mixture thereof,
from 15% to 50% of a non hygroscopic salt or mixture thereof and/or from 10 to 60% of optional ingredient(s)
and wherein the pH of the coating is compatible with viability of the coated dehydrated microorganism.

According to a typical embodiment, the coating consists of $K_2HPO_4$ (hygroscopic salt) and $KH_2PO_4$ (non hygroscopic salt). In a specific embodiment the coating consists of $K_2HPO_4$ (50-85%) and $KH_2PO_4$ (15-50%). In a specific embodiment $K_2HPO_4$ and $KH_2PO_4$ are in an equimolar quantity (50%).

According to a typical embodiment, the coating comprises or consists of $K_2HPO_4$ (hygroscopic salt) or a mixture of salts comprising $K_2HPO_4$, and optional ingredient(s) (talc, rice starch and/or sucrose . . . ). A preferred coating is $K_2HPO_4$ (60-90 wt % dry) and talc (10-40 wt % dry). A particular preferred coating of the invention is $K_2HPO_4$ (83 wt % dry) and talc (17 wt % dry) (see sample 27 of table 1).

Another particular preferred coating of the invention can be obtained by mixing $KH_2PO_4$ (non hygroscopic salt) with NaOH (optional ingredient). The addition of NaOH allows adjustment of the pH of the coating to pH 6.5 and it also reacts with $KH_2PO_4$ to surprisingly provide a suitable hygroscopic coating. Without being bound to any theory, the inventors believe that the equilibrium of the salt in solution is changed by addition of NaOH and that the non-hygroscopic character of $KH_2PO_4$ is altered once applied onto the dehydrated microorganism. For example a particular coating is $KH_2PO_4$ (83 wt % dry) and talc (17 wt % dry) (see sample 28 of table 1).

The three pKa values for phosphoric acid are 2.16, 7.21 and 12.32. Therefore, for a pH lower than 2.16, phosphate will be present in an aqueous solution mainly as the $H_3PO_4$ form. For a pH between 2.16 and 7.21, phosphate will be present in an aqueous solution mainly as the $H_2PO_4^-$ form. For a pH between 7.21 and 12.32, phosphate will be present in an aqueous solution mainly as the $HPO_4^-$ form. Above pH 12.32, phosphate will be present in an aqueous solution mainly as the $PO_4^-$ form.

Regarding the sample 28 ($KH_2PO_4$), phosphate will be present in solution mainly as the $H_2PO_4^-$ form. Before pH adjustment with the base, this salt solution has a pH of 5 (see pH value of sample 16, Table 20). When a base is added to $K_2HPO_4$, the equilibrium is shifted from $H_2PO_4^-$ form towards the formation of the $HPO_4^-$ form. * Therefore, modifying the pH of a salt by the addition of a base (or an acid) can change significantly the phosphate form in solution. Therefore, modifying the pH of a salt by the addition of a base (or an acid) can change also significantly the hygroscopicity of the salt upon processing as a result of the change in phosphate form in solution. Indeed, we know that $K_2HPO_4$ (mostly $HPO_4^-$ form in solution) is a hygroscopic salt in the dried state whereas $KH_2PO_4$ (mostly $H_2PO_4^-$ form in solution) is non hygroscopic salt in the dry state. (Indeed, the pH adjustment done on the sample 28 leads to an increase in the $HPO_4^-$ form which is then resulting in a hygroscopic salt coating after processing. By adjusting the pH of a salt solution, it is then possible to obtain a hygroscopic salt in the coating after processing even if the salt used in the liquid coating composition was initially not hygroscopic.

According to a typical embodiment, the coating comprises or consists of $K_2HPO_4$ (hygroscopic salt) and a non hygroscopic salt (sodium acetate tri hydrate, $KH_2PO_4$ . . . ) and at least one optional ingredient (talc, starch, sucrose . . . ) A particular preferred coating of the invention is $K_2HPO_4$ (30 wt % dry), sodium acetate tri hydrate (30 wt % dry), sucrose (17 wt % dry) and talc (14 wt % dry) (see sample 26 of table 1).

Another preferred coating is $K_2HPO_4$ (25-65 wt % dry), $KH_2PO_4$ (15-50 wt % dry), talc (10-30 wt % dry). A particular preferred coating of the invention is K2HPO4 (48 wt % dry), KH2PO4 (35 wt % dry), talc (17 wt % dry) (see sample 10 of table 1). Another particular preferred coating consists of $K_2HPO_4$ (63 wt % dry), $KH_2PO_4$ (20 wt % dry), and talc (17 wt % dry) (see sample 22 of table 1).

Another particular coating consists of an equi-molar quantity of $KH_2PO_4$ and $K_2HPO_4$ with talc.

According to another typical embodiment, the coated dehydrated microorganism comprises a dehydrated microorganism surrounded by at least one coating comprising or consisting of $K_2HPO_4$ (hygroscopic salt) and $KH_2PO_4$ (non hygroscopic salt), and several optional ingredients (for example sucrose and either talc or starch). A preferred coating is $K_2HPO_4$ (25-50 wt % dry), $KH_2PO_4$ (20-40 wt % dry), sucrose (10-30 wt % dry) and talc (10-30 wt % dry), more preferably a coating of $K_2HPO_4$ (30-45 wt % dry), $KH_2PO_4$ (25-35 wt % dry), sucrose (15-25 wt % dry) and talc (10-20 wt % dry). A particular preferred coating of the invention is $K_2HPO_4$ (40 wt % dry), $KH_2PO_4$ (29 wt % dry), sucrose (17 wt % dry) and talc (14 wt % dry) (see sample 11 of table 1).

The inventors surmise that a high MHC or a high MUR of a coating is a result of the physical properties of the hygroscopic salt(s) contained within the coating and of the structure of the coating. Indeed the hygroscopic salt(s) is/are capable of absorbing or retaining moisture within the coated layer without altering microorganism viability, which is surprising. When the inventors had prepared coated dehydrated microorganisms comprising a dehydrated microorganism surrounded by at least one coating comprising the hygroscopic salt(s), they found that this coating layer comprising such hygroscopic salt(s) leads to an amorphous or partially amorphous (semi-crystalline) state, particularly when using techniques leading to rapid deshydratation of the coating (spray-drying or fluid-bed coating). Moisture absorption will depend on the amount and the behaviour of the hygroscopic salt(s) and on the structure of the final coating. Without wishing to be bound by theory, the inventors hypothesize that this amorphous or partially amorphous state could explain in part the enhanced microorganism viability. Indeed the inventors have shown that when the coating is not fully crystalline once processed to obtain a dry coating ("once processed" means once applied onto the dehydrated microorganism), its capacity to absorb moisture is significantly greater and surprisingly the viability is enhanced compared to coatings which are non hygroscopic. the benefit conferred by the coating in the dried state relates to the amount of moisture the solid coating can absorb, and this amount is greater for amorphous (non-crystalline) or for partially amorphous (semi-crystalline) coatings. Amorphous or partially amorphous (semi-crystalline) state allows for enhanced moisture absorption into the coating bulk phase. Presence of amorphous structure in the coating induces higher MUR and continual increase in the percentage of moisture uptake. Relatively low percentage of amorphous material can absorb considerable amount of moisture into their structure (Encyclopedia of Pharma tech, Vol 6). Both MUR and MHC will depend on the amount and the behaviour of the hygrospic salts, as well as on the structure of the final coating.

The inventors have shown that when the coating is amorphous or not fully crystalline once processed (i.e. applied onto the dehydrated microorganism), its capacity to absorb moisture is significantly greater and surprisingly the viability is enhanced compared to coatings which are non hygroscopic: the benefit conferred by the coating in the dried state relates to the amount of moisture the solid coating can absorb, and this amount is greater for amorphous (non-crystalline) or partially amorphous (semi-crystalline) coatings.

According to the invention a "crystalline state" means that the state is characterized by a perfectly ordered lattice in which there is long-range atomic order, while a "non-crystalline" (or "amorphous") state is characterized by a disordered lattice in which there is no long-range order of the positions of the atoms. These represent two extremes of lattice order and intermediate states are possible. In principle, given a sufficiently high drying rate, any liquid composition can be made into an amorphous solid. Drying reduces molecular mobility. If the drying rate is faster than the rate at which molecules can organize into a more thermodynamically favorable crystalline state, then an amorphous solid will be formed. In contrast, if molecules have sufficient time to organize into a structure with two- or three-dimensional order, then a crystalline (or semi-crystalline) solid will be formed. Amorphous materials can also be produced by additives which interfere with the ability of the primary constituent to crystallize.

When hygroscopic salt(s) is/are processed either alone/together or in a blend with at least one non hygroscopic salt and/or at least one optional other ingredient, using a technique allowing for rapid dehydration such as fluid-bed coating, it results in a disordered solid of low crystallinity. This state of "low crystallinity" has a beneficial effect in the dried state. Indeed, the benefit conferred in the dried state relates to the amount of moisture the solid can absorb; this amount is greater for coatings presenting amorphous structure.

To prepare the dehydrated coated microorganisms according to the invention, processes used to obtain dried solids leading to partially or fully amorphous coatings are therefore preferred. For example, fluid-bed-coating is one of the most preferred techniques to prepare the coated dehydrated microoganisms as it leads to rapid deshydratation and it can result in an amorphous structure.

In one embodiment, said the salt (s) present in the coating (hygroscopic salt(s) and non hygroscopic salt (s)) has/have a salt crystallinity degree (grams of salt(s) under the crystalline form divided by the grams of coating) of up to 60% once the coating is processed (i.e. once the coating is applied onto the dehydrated microorganism), preferably up to 50%, more preferably up to 40% and even more preferably up to 30%.

The crystallinity degree of the salt(s) present in the coating was determined on the coating once processed, that is to say after the liquid coating composition is applied onto the dehydrated microorganism and dried. According to the invention, the expression "crystallinity degree" means the fractional amount of salt(s) of the coating, expressed as a percentage by mass that is generally present in a crystalline state, the remainder of the salts of the coating being present in an amorphous state.

The degree of crystallinity can be measured by various techniques known to one skilled in the art, such as i) X-ray diffraction (see *Encyclopaedia of Pharmaceutical Technology*, 2002) or ii) isothermal Differential Scanning calorimetry (isothermal DSC) (*Kedward, MacNaughtanm Blanchard and Mitchell*, 1998).

When using X-ray diffraction (XRD), the X-ray diffraction pattern of every crystalline form of a compound is unique, the technique is widely used for the identification and characterization of solid phases. The technique can also reveal differences in the crystallinity of compounds. The XRD pattern of an amorphous (non-crystalline) compound will consist of one or more broad diffuse halos (*Encyclopaedia of Pharmaceutical Technology*, 2002, page 3005).

The degree of crystallinity according to the invention can also be measured using a DSC (Differential Scanning calorimetry). For examplea Netzch DSC 204 (Netzsch, Germany) equipped with an intracooler was used for all measurements with $N_2$ as flushing agent according to TEST A. Test A consists of the following protocol: Samples of 10 mg of the coating were weighed and immediately hermetically sealed into into aluminium DSC pans. The scan was run by first cooling and holding each sample at an initial temperature of −50° C. for 2 minutes. The samples were then heated from −50° C. to 330° C. at 12° C. $min^{-1}$ and held at 330° C. for 3 minutes. This test was used in example 11 to characterize the amorphous state of the coating obtained by fluid-bed drying. The test was carried out on the coating itself produced under the same process conditions as those used to coat the dehydrated microorganisms, as described in example 11. Hence, the thermograms shown in FIGS. 10 to 12 are characteristic of the structure of the coating of the present invention. The degree of crystallinity of the salt(s) of the coating is independent of the presence of the underlaying dehydrated microorganisms since each consists of a separate layer.

The degree of crystallinity can also be measured using other suitable techniques such as TMA (Thermal Mechanical Analysis) that will measure the response of coating to changes in temperature and a glass transition temperature characteristic of an amorphous structure can be determined. The technique uses probes that are placed into the coating.

According to a particular embodiment, the coating has a Moisture Uptake Rate (MUR) of at least 15%, preferably at least 20%, preferably at least 30%, at 25° C. and at 75% relative humidity (RH) after 7 days.

According to a particular embodiment, the coated dehydrated microorganism has Moisture Uptake Rate of at least 8%, at 25° C. and at 75% relative humidity (RH) after 7 days.

Water sorption isotherms were conducted to characterize the hygroscopicity of the coated dehydrated microorganism. The coated dehydrated microorganism (or the coating of the invention) exhibited a strong change in its water content as a function of relative humidity, thereby indicating a highly hygroscopic behaviour. In addition, the profile showed a continuous increase in water content, which is characteristic of an amorphous or partially amorphous structure.

Moreover, as already mentioned, it is advantageous to process the coating in such a way as to ensure a rapid rate of drying (eg. by fluid-bed coating) as this prevents the creation of an ordered structure, leading to the formation of a solid solution. The low crystalline structure is therefore the result of a phase transition during the process and does not reflect the initial solid state of each individual salt. A partially crystalline coating containing at least 25% of a hygroscopic salt or mixture thereof, has a significantly greater capacity to absorb moisture. Surprisingly, the viability of the dehydrated microorganism is enhanced by this enhanced moisture absorbing capacity, provided that there is a pH compatible with viability of the coated dehydrated microorganism. Without wishing to be bound by theory, the inventors think that this phenomenon could be partially linked to the fact that the coating is not fully crystalline once processed, especially when rapid rate drying techniques are used.

In a particular embodiment, the coated dehydrated microorganism according to the invention has a stability after it is manufactured, during storage in dry conditions, and before end-use of minimum 40% survival, preferably at least 50% survival, preferably at least 60% survival, preferably at least 70% survival, preferably at least 80% survival and preferably 90% survival upon storage from 15° C. to 40° C. for up to 2 years when stored in sealed conditions.

A high viable bacteria survival rate is obtained in the intended applications after several months of storage of final products (e.g. in food products, feed products, consumer healthcare products or agri-products) comprising the coated dehydrated microorganisms according to the invention (e.g. after 1 month of storage, even after 2 months, even after 3 months, even after 5 months, even after 9 months, even after 12 months, even after 2 years, even longer . . . ), especially when stored at ambient temperatures (e.g. from 15° C. to 40° C., especially from 20-35° C., for example at 23° C. or 30° C.), and especially when the water activity (aw) of the final product is greater than 0.10. The coating of the present invention is therefore a stabilizing coating for dehydrated microorganisms.

In a particular embodiment, the coated dehydrated microorganism according to the invention is capable to have a viability loss of <1.5 LOG, most preferably of <1.0 LOG, most preferably of <0.5 LOG, most preferably of <0.2 LOG, and most preferably of <0.1 LOG upon 12 months storage at temperature from 15° C. to 40° C., in a feed product, a food product, a consumer healthcare product or an agri-product having an aw greater than 0.10.

The viability loss is the reduction of the number of viable cells as measured by cfu (colony forming unit) before and after any exposure. It is generally expressed in LOG. According to the invention, the term LOG or E or $^E$ is intended to mean decimal logarithm, i.e., a multiplicative factor of ten.

In another particular embodiment, the coated dehydrated microorganism according to the invention is capable to have viability loss of <3 LOG, most preferably of <1.5 LOG, most preferably of <1.0 LOG, most preferably of <0.5 LOG, and most preferably of <0.2 LOG upon 2 years storage at temperature from 15° C. to 40° C., in a feed product, a food product, a consumer healthcare product or an agri-product having an aw greater than 0.10.

The coating according to the invention is a stabilizing coating which surrounds and protects dehydrated microorganisms against moisture and/or heat. The technology can be used for sensitive dehydrated microorganisms. By "sensitive" it is meant having a low viability when exposed to high humidity and/or high temperature. These coated dehydrated living microorganisms will have an increased survival rate in stressfull conditions as well as an extended shelflife (e.g. of at least 1 month, or of at least 2 months, or of at least 5 months or of at least 12 months or of at least 2 years or even longer, especially when stored at ambient temperatures, e.g. from 15° C. to 40° C., especially from 20-35° C., for example at 23° C. or 30° C., and especially when aw in the final product is greater than 0.10). In addition, if conventional outercoating(s) (such as fats; fatty acids (e.g. stearic acid); emulsifiers (such as mono and di-glycerides); oils; waxes; resins; low permeability polymers (e.g. shellac, sepifilm, polyvinyl pyrolidone, poly ethylene glycol); hydrocolloids (e.g. carrageenans, alginates or gum arabic or xanthan gum or guar gum); starches which may be used as native or modified starches derived from potatoes, corn, whey, rice, potatoe, tapioca; cyclodextrines; polyols (e.g. mannitol); cellulose and cellulose derivatives (HPMC, cellulose esters, cellulose ethers), and mixtures thereof) is/are added, the coated dehydrated microorganism, especially coated sensitive dehydrated microorganism, will be more resistant to unfavorable pH for an enhanced survival into the gastrointestinal tract and/or to oxidative environments and/or to processes including steam-treatment, and it will retain most of its activity.

Another advantage provided by the present invention is that the coated dehydrated microorganisms that are obtained do not stick together under ambient conditions despite the use of hygroscopic salt(s). Free-flowing particulates of dehydrated microorganisms with enhanced viability are therefore obtained.

The dehydrated microorganism of the invention is typically selected from the group comprising yeasts, molds, fungi, bacteria or any mixture thereof. One or several kinds of microorganisms can be coated.

Examples of suitable yeasts are: *Kluyveromyces* spp, *Debaryomyces* spp, *Yarrowia* spp, *Pichia* spp, *Williopsis* spp, *Saccharomyces* spp.

Examples of suitable fungi/molds are: *Penicillium* spp, *Geotrichum* spp, *Lecanicillium* spp, *Trichothecium* spp.

Examples of suitable bacteria are: coryneform bacteria such as for example *Arthrobacter* spp, *Corynebacterium* spp, *Brevibacterium* spp, or lactic acid bacteria.

The dehydrated microorganism is preferably a lactic acid bacteria. According to the invention, the term "lactic acid bacteria" includes any bacteria capable of producing, as the major metabolic end product of carbohydrate fermentation, lactic acid or at least one of its derivatives (including, but not limited to, propionic acid). The term is therefore intended to include propionic acid bacteria (PAB), which produce propionic acid as a carbohydrate fermentation product.

Preferably the bacteria for use in the present invention are lactic acid bacteria which are generally recognised as safe for animal or human consumption (i.e. GRAS approved).

Suitable lactic acid bacteria may be selected from the genus *Lactococcus, Lactobacillus, Leuconostoc, Bifidobacterium, Carnobacterium, Enterococcus, Propionibacterium, Pediococcus, Streptococcus* and mixtures thereof.

Typically, the microorganisms are probiotics or DFM (Direct Fed Microbials). According to the invention "probiotics" or "DFMs" means live microorganisms which when administered in adequate amounts confer a health benefit on the host, the host being a human in the case of probiotics and an animal in the case of DFMs. The probiotic microorganisms or DFMs most commonly used are principally bacteria and yeasts of the following genera: *Lactobacillus* spp., *Streptococcus* spp., *Enterococcus* spp., *Bifidobacterium* spp. and *Saccharomyces* spp.

In a typical embodiment, the coated dehydrated microorganism according to the invention is selected from the group of *Lactobacillus*. Typically, the microorganisms used are *L. acidophilus* or *L. plantarum*, and more preferably *L. acidophilus* NCFM commercially used by the Applicant under the name *L. acidophilus* NCFM® or *L. plantarum* Lp115 having been deposited according to the Budapest Treaty on Feb. 9, 2009 in the name of Danisco Deutschland GmbH, Busch-Johannsen-Str.1 25899, Niebüll, Germany, at the Deutsche Sammlung von Mikroorganismen and Zellkulturen located at Inhoffenstr. 7 B, D-38124 Braunscheiwg, Germany under no. DSM22266.

The coated dehydrated microorganism can contain from $10^4$ to $10^{14}$ cfu/g, preferably from $10^7$ to $10^{11}$ cfu/g by weight of the coated dehydrated microorganism.

Typically, the dehydrated microorganisms can be obtained by conventionally used methods, such as "freeze-drying" or by "spray-coating of the microorganisms onto an inert core".

Preparation of the dehydrated microorganism can be but is not limited to freeze-drying and spray-coating microorganisms onto an inert core. Other possible methods are 1) absorption of microorganisms or oil-suspended microorganisms on a porous inert carrier, 2) spray-drying of microorganisms, optionally followed by agglomeration, spray-granulation and high shear granulation of the microorganisms, and 3) any other methods known to the skilled man in the art and which provide a dehydrated microorganism in a form suitable for further coating.

According to a typical embodiment, the liquid coating composition is spray-coated onto the dehydrated microorganism in order to get the coated dehydrated microorganism of the invention.

A preferred embodiment of the invention is therefore a dehydrated microorganism, which is spray-coated with a liquid composition so as to obtain a coated dehydrated microorganism comprising a dehydrated microorganism surrounded by at least one coating, said coating comprising by dry weight at least 25% of hygroscopic salt or mixture thereof and wherein the pH of the coating is compatible with viability of the coated dehydrated microorganism.

Typically, any method allowing a rapid rate of drying of the liquid coating composition may be used to spray-coat the coating onto the microorganisms, in order to obtain the formation of a non-crystalline or partially crystalline coating. Preferably, the coating is done in a fluid-bed type coating apparatus.

In a typical embodiment, the coated dehydrated microorganism which has already been coated with at least one layer of coating according to the invention (also referred to as $1^{st}$ coating), may be subsequently coated with at least one further coating (also referred to as outercoating(s)) comprising for example any conventional coating components such as fats; fatty acids (e.g. stearic acid); emulsifiers (such as mono and di-glycerides); oils; waxes; resins; low permeability polymers (e.g. shellac, sepifilm, polyvinyl pyrolidone, poly ethylene glycol); hydrocolloids (e.g. carrageenans, alginates or gum arabic or xanthan gum or guar gum); starches which may be used as native or modified starches derived from potatoes, corn, whey, rice, potatoe, tapioca; cyclodextrines; polyols (e.g. mannitol); cellulose and cellulose derivatives (HPMC, cellulose esters, cellulose ethers), and mixtures thereof.

The outercoating(s) allow(s), in addition to an increased resistance to high temperature and/or high humidity levels provided by the coating according to the invention ($1^{st}$ coating), to get an increased resistance of the dehydrated microorganisms to gastric and/or oxidative environments and/or conditions with unfavourable pH, especially when the coated dehydrated microorganisms are particularly sensitive. It has also the advantage to help these dehydrated microorganisms to resist to processes using steam-treatment, as it is the case in most of the processes to prepare for example feed products or recombined cheese.

Typically, the coating according to the invention is in a quantity of at least 10% by weight of the coated dehydrated microorganism, preferably at least 20%, more preferably at least 30%, more preferably at least 50% and even more preferably at least 70%, even more preferably at least 80%, even more preferably at least 90% by weight of the coated dehydrated microorganism. In a particular embodiment the coated dehydrated microorganism comprising a dehydrated microorganism surrounded by several layers of coating according to the invention that may comprise different compositions. Outercoating(s)) comprising for example any conventional coating components can be then added.

Another object of the present invention is a liquid coating composition comprising at least 25% of a hygroscopic salt or mixture thereof by weight of dry solids contained in the coating composition. By liquid coating composition, it has to be understood that the liquid mixture of component(s) prepared before it is applied onto the dehydrated microorganism and dried. All of the preferred embodiments which have been previously described, such as for example, in relation to the types of components, the range of pH, also apply to the liquid coating composition.

Another object of the present invention is a method for coating a dehydrated microorganism, said method comprising the steps of:
(a) preparing a liquid coating composition
(b) coating a dehydrated microorganism with the liquid coating composition obtained after step (a), preferably by spray-coating to obtain a coated dehydrated microorganism.

In a particular embodiment, the liquid coating composition comprises a hygroscopic salt or mixture thereof.

The process allows obtaining a coated dehydrated microorganism according to the invention, i.e. comprising a dehydrated microorganism surrounded by at least one coating comprising by dry weight at least 25% of hygroscopic salt or mixture thereof and wherein the pH of the coating is compatible with viability of the coated dehydrated microorganism.

The hygroscopic salt(s) is/are preferably dissolved into an aqueous medium.

0 to 60% by dry weight of a non hygroscopic salt or mixture thereof, and/or 0 to 70% by dry weight of other optional ingredient(s) can also be ingredients of the liquid coating composition. They can be added either dissolved or suspended into to the liquid coating composition.

All of the preferred embodiments which have been previously described, such as for example, in relation to the types of components contained within the coating, the nature of the coating (e.g. degree of crystallinity, MUR . . . ) and/or the microorganisms, also apply to the method for coating a dehydrated microorganism.

According to a preferred embodiment, step (b) must be performed at a temperature suitable to ensure rapid drying thereby preventing crystallization of the salts(s) of the coating surrounded the dehydrated microorganism, while preserving the viability of the coated microorganism. The temperature and duration of processing are chosen to ensure the amorphous or partially crystalline nature of the coating according to the invention, resulting from phase transition during the process.

Steps (a) and (b) can be repeated several times, to provide a coated dehydrated microorganism coated by several layers. The composition of these different layers can be the same or different.

The method for coating a dehydrated microorganism can further comprise a step (c):
(c) coating the coated dehydrated microorganism obtained after step (b) with at least one outercoating. This at least outercoating is preferably made using conventional compounds such as fats; fatty acids (e.g. stearic acid); emulsifiers (such as mono and di-glycerides); oils; waxes; resins; low permeability polymers (e.g. shellac, sepifilm, polyvinyl pyrolidone, poly ethylene glycol); hydrocolloids (e.g. carrageenans, alginates or gum arabic or xanthan gum or guar gum); starches which may be used as native or modified starches derived from potatoes, corn, whey, rice, potatoe, tapioca; cyclodextrines; polyols (e.g. mannitol); cellulose and cellulose derivatives (HPMC, cellulose esters, cellulose ethers), and mixtures thereof.

The liquid coating composition of the invention will be applied onto the dehydrated microorganism, i.e. in a separate coating layer.

The coated dehydrated microorganism can be prepared by two preferred methods which have shown significant improvement in stability over commercial freeze-dried microorganims powders:
1) Liquid Route (i.e. includes the application of liquid culture of microorganisms by fluid-bed drying onto an inert core, see FIG. 1A), or
2) Solid Route (i.e. includes the preparation of a dried culture, see FIG. 1B).

General Description of the "Liquid Route" Method

One method to produce the highly stable dehydrated microorganisms of the present invention with increased survival rate in stressful conditions and extended shelf-life is the "liquid-route" method. This method involves preparing a primary particle by spray-coating an inert carrier particle (i.e an inert core) with a liquid preparation of microorganisms. The primary particle is therefore composed of an inert core coated by at least one thin layer of dehydrated living microorganisms. The primary particle is then further coated with a coating according to the present invention. In this case, where the liquid culture of microorganisms is sprayed onto an inert core, it is necessary to control both the formulation of the microorganism-containing layer and the process conditions, in order to maximise the microorganism survival. In terms of the microorganism-containing layer, both the composition of the formulation and the pH of the formulation need to be optimized.

A preferred method to prepare both the primary and the coated particle is through fluid-bed coating. In this approach, the primary particle is prepared by fluidizing the inert core material on an air stream and spraying the liquid culture of microorganisms onto the core material. Process conditions are chosen so as to ensure: i) maximized physical yields (i.e. ratio between the material recovered at the end of the process to the material added during the process), ii) maintenance of the viability of the microorganism, iii) minimized residual moisture in the microorganism-containing layer.

The primary particle is then further spray-coated with a liquid coating composition according to the invention. The liquid coating composition is prepared by ensuring that the requisite amounts of the desired components and the optional components are either fully dissolved in an aqueous medium (eg. distilled water) or suspended in the liquid coating composition. This liquid coating composition is then sprayed onto the primary particles which are fluidized by an air stream. Process conditions are chosen so as to ensure: i) production of a coating in a partially crystalline state, ii) maximized physical yields (i.e. ratio between the material recovered at the end of the process to the material added during the process), iii) minimal rewetting of the dried living microorganism-containing layer, iv) rapid drying of the coating solution on the particle surface, v) formation of a multi-layer coating structure which is uniformly distributed over the surface of the primary particle (see example 1).

General Description of "Solid Route" Method

Another method for producing the highly stable dried composition containing coated living dehydrated microorganisms of the present invention with increased survival in stressful conditions and extended shelflife is the "solid route" method. In this method, the liquid coating composition of the invention is directly spray-coated onto dried dehydrated microorganism in a fluid-bed process. The dried dehydrated microorganisms may be a freeze-dried powder. Other possible methods used to obtain the dried dehydrated microorganism are α) absorption of microorganisms or oil-suspended microorganisms on a porous inert carrier, β) spray-drying of microorganisms, optionally followed by agglomeration, spray-granulation and high shear granulation of the microorganisms and δ) any other suitable methods known to the skilled man in the art. In a preferred embodiment the dried powder is a freeze-dried powder. The dried dehydrated microorganism powder can be obtained by methods previously described in prior art, such as for example in WO03/018778.

Another object of the present invention is a method for protecting a dehydrated microorganism, said method comprising preparing a coated dehydrated microorganism by surrounded the dehydrated microorganism with at least one coating comprising by dry weight at least 25% of a hygroscopic salt or mixture of hygroscopic salts and wherein the pH of the coating is compatible with viability of the coated dehydrated microorganism. Another object of the present invention is the use of at least one coating comprising by dry weight at least 25% of a hygroscopic salt or a mixture thereof, wherein the pH of the coating is compatible with viability of the coated dehydrated microorganism, for protecting a dehydrated microorganism.

In a particular embodiment the dehydrated microorganism is coated by several layers. The composition of these different layers can be the same or different.

In another particular embodiment there is at least one outercoating, which is preferably made using conventional compounds such as fats; fatty acids (e.g. stearic acid); emulsifiers (such as mono and di-glycerides); oils; waxes; resins; low permeability polymers (e.g. shellac, sepifilm, polyvinyl pyrolidone, poly ethylene glycol); hydrocolloids (e.g. carrageenans, alginates or gum arabic or xanthan gum or guar gum); starches which may be used as native or modified starches derived from potatoes, corn, whey, rice, potatoe, tapioca; cyclodextrines; polyols (e.g. mannitol); cellulose and cellulose derivatives (HPMC, cellulose esters, cellulose ethers), and mixtures thereof.

As already mentioned, the coated dehydrated microorganism according to the invention has a stability after it is manufatured, during storage in dry conditions, and before end-use of minimum 40% survival, preferably at least 50% survival, preferably at least 60% survival, preferably at least 70% survival, preferably at least 80% survival and more preferably 90% survival upon storage from 15° C. to 40° C. (especially from 20° C. to 35° C., for example at 23° C. or 30° C.) for up to 2 years when stored in sealed conditions, e.g. in a hermetic sachet.

In a particular embodiment the coated dehydrated microorganism according to the invention has a viability loss of <1.5 LOG, most preferably of <1.0 LOG, most preferably of <0.5 LOG, most preferably of <0.2 LOG, and most preferably of <0.1 LOG upon 12 months storage at temperature from 15° C. to 40° C. (especially from 20° C. to 35° C., for example at 23° C. or 30° C.), in a feed product, a food product, a consumer healthcare product or an agri-product, especially having an aw greater than 0.10.

In a particular embodiment the coated dehydrated microorganism according to the invention has a viability loss of <3 LOG, most preferably of <1.5 LOG, most preferably of <1.0 LOG, most preferably of <0.5 LOG, and most preferably of <0.2 LOG upon 2 years storage at temperature from 15° C. to 40° C. (especially from 20° C. to 35° C., for example at 23° C. or 30° C.), in a feed product, a food product, a consumer healthcare product or an agri-product, especially having an aw greater than 0.10.

The coating of the present invention is therefore a stabilizing coating for dehydrated microorganisms.

All of the preferred embodiments which have been previously described, such as for example, in relation to the types of components contained within the coating, the nature of the coating (e.g. degree of crystallinity, MUR . . . ) and/or the microorganisms, also apply to the method (or use) for protecting a dehydrated microorganism.

Another object of the present invention is a method for the preparation of food products, feed products, consumer healthcare products or agri-products, wherein the coated dehydrated microorganism as defined in the invention or as obtained according to the method of preparation of the present invention is subsequently added to a food product, a feed product, a consumer healthcare product or an agri-product.

According to the present invention "food" means products suitable for human consumption. They are materials which contain or consist of essential body nutrients, such as carbohydrates, fats, proteins, vitamins, or minerals, and is ingested and assimilated by an organism to produce energy, stimulate growth, and maintain life, presented in the form of a solid, liquid or paste for practical consumption. These materials are often combined and mixed at high temperature and contain high humidity. The coated dehydrated microorganisms of the present invention are suitable for use in food products. They can be mixed with the food materials which can be subsequently baked, steam treated, compressed, granulated and/or molded (nutritional bars, string cheese, breakfast cereals, etc. . . . ). For steam treatment, it is preferred that the coated dehydrated microorganisms contain at least one outercoating made using conventional compounds, especially for the sensitive microorganisms.

The coated dehydrated microorganism of the present invention can be used as an ingredient in the preparation of foods selected from the group comprising nutritional bars, breakfast cereals, infant formulas, biscuits cakes, cake mixes, snack foods, balanced foods and drinks, fruit fillings, cake glaze, chocolate bakery fillings, cheese cake flavoured fillings, fruit flavoured cake fillings, cake and doughnut icings, instant bakery filling creams, filings for cookies, ready-to-use bakery fillings, reduced calorie fillings, desserts, confectionery products (eg. gummi bears, candies, chocolates and chocolate chips, pralines, chewing gums, popcicles), beverages such as beverage powders, soft drinks, fruit juices, beverages comprising whey proteins, health teas, cocoa drinks, milk-based drinks, calcium fortified soy plain and chocolate milks, calcium fortified coffee beverages, lactic acid bacteria-based drinks, adult nutritional beverages, acidified soy/juice beverages, aseptic/retorted chocolate drinks, yoghurts, drinking yoghurts, cheeses, string cheeses, recombined cheeses, ice creams, sherbets. Amongst food products, nutritional bars, breakfast cereals, infant formulas and beverage powders are particularly preferred.

According to the present invention "feed" means products suitable for animal consumption and can be selected from the group comprising "pet foods" (cakes, biscuits, chews, snacks . . . for pets), silage products and pelleted feeds. The term "animal" has to be understood under a wide meaning. It can refer to a "polygastric herbivore" which includes, but is not limited to, bovinae, cervidae, antilocapridae and camelidae. It can refer for example to a "polygastric ruminant" which includes, but is not limited to cows, sheeps, ewes, goats, dears, camels, giraffes. It can also refer to a "monogastric herbivore" such as equines and porcines as well as to domesticated animal or pets (dogs, cats, rabbits, birds, rats, mice, guinea pigs, fishes, reptils . . . ). It can also refer to poultry, chicken, chick and also to any kind of animals from aquaculture area such as shrimps etc. . . .

The coated dehydrated microorganism of the invention may be added to unpelletized feed mixture, which may be subsequently treated with steam and/or which are steam pelleted or dried. The unpelleted mixture refers to premixes and mashes. "Premixes" typically contain vitamin and minerals. Other ingredients such as grains and clays may also be added to premixes. "Mashes" typically contain the complete animal diet. "Pellets" are particles of spherical or cylindrical shape typically created by compressing the original feed mixture which can contain the coated dehydrated microorganisms of the invention. Before compression, the feed mixture is steamed treated in a conditioner for 30 seconds to 5 min at temperature varying from 60° C. to 95° C. using injected steam. As mentioned above, because of steam treatment, it is preferred that the coated dehydrated microorganisms contain at least one outercoating made using conventional compounds, especially for the sensitive microorganisms. The stream treated feed mixture is then transfered to a pellet mill or extruder and finally to a pellet cooler.

The coated dehydrated microorganism of the invention may be included into gels or other oil delivery systems in order to directly supplement the animals. It can also be powders or other dry formulations for top dressing feed for example.

According to the present invention, "consumer healthcare products" include dietary supplements, nutraceuticals and over-the-counter products. A consumer can be a human and/or an animal.

According to the present invention a "dietary supplement" (also referred to as a food supplement or nutritional supplement), means a preparation intended to provide nutrients, such as vitamins, minerals, fiber, fatty acids or amino acids, which are missing or are not consumed in sufficient quantity in a person's diet. A dietary supplement can be for human and/or animal consumption.

According to the present invention, the term "nutraceutical" means a functional food which is capable of providing not only a nutritional effect and/or a taste satisfaction, but is also capable of delivering therapeutic (or other beneficial) effects to the consumer.

According to the present invention, "over-the-counter product" means non prescription medicines which can prevent certain diseases or reduce symptoms associated with gut health or immune health, thereby promoting gut health or improving the immune function. For example, these products allow prevention and treatment of allergies, prevention and treatment of respiratory tract infection and other emerging applications of probiotics and direct fed microbials (DFMs).

According to the present invention the expression "agri-product" encompasses biopesticides, biofertilizers, products for plant care, composts and by-products as well as products of bioenergy (bio ethanol, bio ester).

These products (food, feed, consumer healthcare products and agri-products) can be prepared in any kind of form such as in liquid, suspension, semi-solid, tablets, capsules, pellets, pills, powder, gels or other delivery systems, etc. In a typical embodiment, the coated dehydrated microorganisms of the present invention can be incorporated into a microperforrated straw or any other microperforrated packaging technologies or devices All of the preferred embodiments which have been previously described, such as for example, in relation to the types of components contained within the coating, the nature of the coating (e.g. degree of crystallinity, MUR . . . ) and/or the microorganisms, also apply to the method for the preparation of food product, feed product, consumer healthcare products or agri-products.

Another object of the present invention is food products, feed products, consumer healthcare products or agri-products comprising coated dehydrated microorganisms as defined or as obtained in the present invention. A high bacteria survival is obtained after several months of storage of final products comprising the coated dehydrated microorganisms according to the invention (e.g. after 1 month of storage, even after 2 months, even after 3 months, even after 5 months, even after 9 months, even after 12 months, even after 2 years, even longer . . . ), especially when stored at ambient temperatures (e.g. from 15 to 40° C., especially from 20° C. to 35° C., for example at 23 or 30° C.) and especially the aw of the final products is greater than 0.10.

All of the preferred embodiments which have been previously described, such as for example, in relation to the types of components contained within the coating, the nature of the coating (e.g. degree of crystallinity, MUR . . . ) and/or the microorganisms, also apply to the food products, feed products, consumer healthcare products and agri-products comprising said coated dehydrated microorganism.

Another object of the present invention is coated dehydrated microorganism obtainable by the method of preparation of the present invention.

Another object of the present invention is coated dehydrated microorganism directly obtained by the method of preparation of the present invention.

All of the preferred embodiments which have been previously described, such as for example, in relation to the types of components contained within the coating, the nature of the coating (e.g. degree of crystallinity, MUR . . . ) and/or the microorganisms, also apply to the coated dehydrated microorganism obtainable/obtained by the method of preparation of the present invention.

Another object of the present invention is the use of the coated dehydrated microorganism according to the invention to produce a recombined cheese, said recombined cheese being produced by the following steps:

i) grinding of the curd,
ii) addition of hydrocolloids (no melting salts) to give the right texture to the final product,
iii) heating to 60° C., and
iv) stirring at 60° C. while adding the coated dehydrated microorganisms.

All of the preferred embodiments which have been previously described, such as for example, in relation to the types of components contained within the coating, the nature of the coating (e.g. degree of crystallinity, MUR . . . ) and/or the microorganisms, also apply to the use of the coated dehydrated microorganism to produce a recombined cheese. However, as steam-treatment is generally used in the production of recombined cheese, it is preferred that the coated dehydrated microorganism according to the present invention contains at least one outercoating, which is preferably made using conventional compounds such as fats; fatty acids (e.g. stearic acid); emulsifiers (such as mono and di-glycerides); oils; waxes; resins; low permeability polymers (e.g. shellac, sepifilm, polyvinyl pyrolidone, poly ethylene glycol); hydrocolloids (e.g. carrageenans, alginates or gum arabic or xanthan gum or guar gum); starches which may be used as native or modified starches derived from potatoes, corn, whey, rice, potatoe, tapioca; cyclodextrines; polyols (e.g. mannitol), cellulose and cellulose derivatives (HPMC, cellulose esters, cellulose ethers), and mixtures thereof.

Other features and advantages of the invention will emerge upon reading the following non limiting examples.

BRIEF DESCRIPTION OF THE FIGURES

FIG. 1 B) is a schematic representation of coated dehydrated microorganisms via the solid route, wherein the starting biological material is a freeze-dried microorganism powder.

FIG. 2 B is a survival graph of coated (sample 11) and uncoated (sample 2) $L.$ $acidophilus$ NCFM into chocolate bar stored at 30° C. * Coating of sample 11: $K_2HPO_4$ (40% dry), $KH_2PO_4$ (29% dry), sucrose (17% dry), talc (14% dry).

EXAMPLES

Figure 1A:
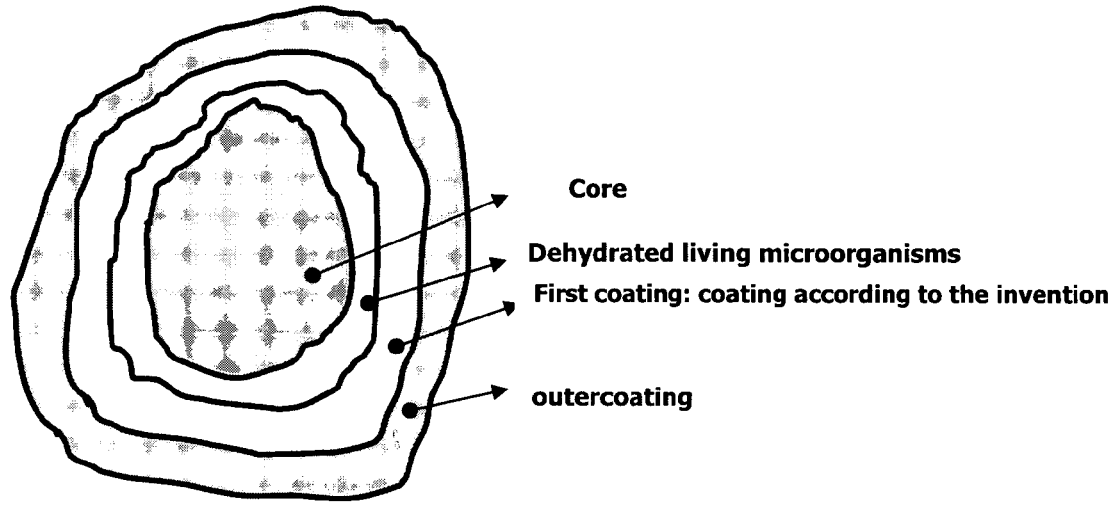
FIG. 1 A) is a schematic representation of coated dehydrated microorganisms via the liquid route, wherein the starting biological material is a liquid microorganism concentrate.
Figure 1B:
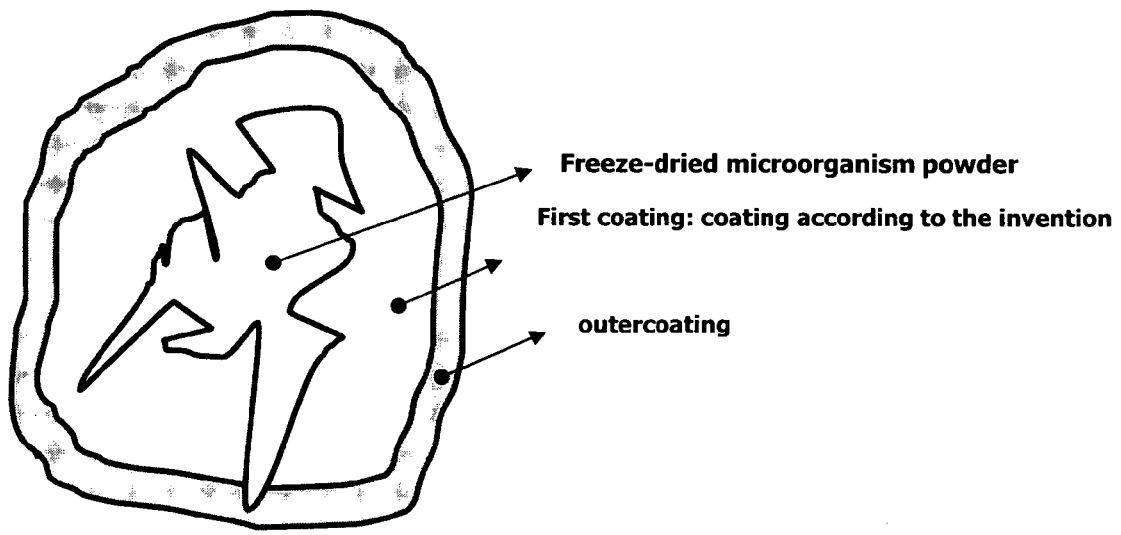

Table 1 is a summary of all tested samples. Some refer to the dehydrated microorganisms coated with the coating of the present invention, while others are dehydrated microorganisms which are coated with a different composition and which do not demonstrate an enhanced microorganism stability in stressed conditions.

TABLE 1

| Sample | Dehydrated microorganisms | 1st coating | Outercoating(s) | Comments |
|---|---|---|---|---|
| 1 | Fluid-bed dried NCFM | None | None | Control, uncoated microorganism |
| 2 | Freeze-dried NCFM | None | None | Control, uncoated microorganism |
| 3 | Freeze-dried Lp115 | None | None | Control, uncoated microorganism |
| 4 | Fluid-bed dried NCFM | None | PS101 Sun flower oil | Conventional coating |
| 5 | Fluid-bed dried NCFM | None | Stearine | Conventional coating |
| 6 | Fluid-bed dried NCFM | None | Sepifilm LP30 | Conventional coating |
| 7 | Fluid-bed dried NCFM | None | Shellac | Conventional coating |
| 8 | Fluid-bed dried NCFM | None | HPMC | Conventional coating |
| 9 | Fluid-bed dried NCFM | None | PS101/Sepifilm LP30 | Conventional coating |
| 10 | Fluid-bed dried NCFM | $K_2HPO_4$ (48% dry), $KH_2PO_4$ (35% dry), sucrose (0% dry), talc (17% dry) | None | An example of coating according to the invention |
| 11 | Fluid-bed dried NCFM | $K_2HPO_4$ (40% dry), $KH_2PO_4$ (29% dry), sucrose (17% dry), talc (14% dry) | None | An example of coating according to the invention |
| 12 | Fluid-bed dried NCFM | $K_2HPO_4$ (14% dry), $KH_2PO_4$ (11% dry), sucrose (54% dry), talc (22% dry) | None | An example of a coating outside the invention |
| 13 | Fluid-bed dried NCFM | $Na_2SO_4$ | None | An example of a coating outside the invention |
| 14 | Fluid-bed dried NCFM | $MgSO_4$ | None | An example of a coating outside the invention |
| 15 | Fluid-bed dried NCFM | $K_2HPO_4$ (83% dry), talc (17% dry) | None | An example of a coating outside the invention (pH not suitable) |
| 16 | Fluid-bed dried NCFM | $KH_2PO_4$ (83% dry), talc (17% dry) | None | An example of a coating outside the invention |
| 17 | Fluid-bed dried NCFM | $K_2HPO_4$ (40% dry), $KH_2PO_4$ (29% dry), sucrose (17% dry), talc (14% dry) | Sepifilm LP30 | An example of coating according to the invention |
| 18 | Fluid-bed dried NCFM | $K_2HPO_4$ (40% dry), $KH_2PO_4$ (29% dry), sucrose (17% dry), talc (14% dry) | Shellac | An example of coating according to the invention |
| 19 | Fluid-bed dried Lp115 | $K_2HPO_4$ (40% dry), $KH_2PO_4$ (29% dry), sucrose (17% dry), talc (14% dry) | Sepifilm Lp30 | An example of coating according to the invention. |
| 20 | Freeze-dried NCFM | $K_2HPO_4$ (40% dry), $KH_2PO_4$ (29% dry), sucrose (17% dry), talc (14% dry) | None | An example of coating according to the invention. |
| 21 | Freeze-dried NCFM | $Na_2SO_4$ | None | An example of a coating outside the invention |
| 22 | Fluid-bed dried NCFM | $K_2HPO_4$ (63% dry), $KH_2PO_4$ (20% dry), talc (17% dry) | None | An example of coating according to the invention. |

TABLE 1-continued

| Sample | Dehydrated microorganisms | 1st coating | Outercoating(s) | Comments |
|---|---|---|---|---|
| 23 | Fluid-bed dried NCFM | $K_2HPO_4$ (23% dry), $KH_2PO_4$ (60% dry), talc (17% dry) | None | An example of a coating outside the invention |
| 24 | Fluid-bed dried NCFM | $K_2HPO_4$ (19% dry), $KH_2PO_4$ (15% dry), Sucrose (52% dry) talc (14% dry) | None | An example of a coating outside the invention |
| 25 | Fluid-bed dried NCFM | $MgCl_2$ (100% dry) | none | An example of coating according to the invention. |
| 26 | Fluid-bed dried NCFM | $K_2HPO_4$ (30% dry), sodium acetate tri hydrate (30% dry), Sucrose (17%) talc (14% dry) | none | An example of coating according to the invention. |
| 27 | Fluid-bed dried NCFM | $K_2HPO_4$ (83% dry), talc (17% dry), pH adjusted to 6.5 with lactic acid | none | An example of coating according to the invention. |
| 28 | Fluid-bed dried NCFM | $KH_2PO_4$ (83% dry), talc (17% dry), pH adjusted to 6.5 with NaOH | none | An example of coating according to the invention |

Note:
All of the percentages refer to the "dry" coating (wt % dry), Samples were made with 30 wt % 1st coating by weight of the coated dehydrated microorganisms

Example 1

Liquid Route-Type Composition

This trial was carried out in an Aeromatic MP-1 fluid bed, run in top-spray mode, using a distributor plate with 8% opening. The spray nozzle was a Schlick 1 mm nozzle, which was placed in the lowest position throughout the process. A Watson-Marlow pump was used to convey the spray material to the nozzle.

Preparation of Primary Particle:

The primary particle was prepared by spray-coating an inert carrier particle (i.e an inert core) with a liquid composition containing *L. acidophilus* NCFM.

The liquid composition containing the microorganisms (culture mixture) was prepared by mixing the following ingredients:

| Ingredients | Amount (%) |
|---|---|
| Liquid culture concentrate* | 64.0 |
| Sucrose | 6.7 |
| milk protein (Promilk 852A) | 6.7 |
| Maltitol | 12.0 |
| Wheat Starch | 10.6 |
| Total | 100.0 |

*Liquid culture concentrate used was *L. acidophilus* NCFM

The pH of the mixture was adjusted to 7.5 with 10M $NH_4OH$.

The fluid bed was charged with 2.8 kg of sucrose cores. Then 0.8 kg of the culture mixture was spray-coated onto the cores, using the following process parameters:

| Parameters | Setting |
|---|---|
| Product Air Temperature | 40° C. |
| Inlet Air Temperature | 55° C. |
| Fluidizing Air Flow Rate | 90 m³/hr |
| Spray Temperature | 5° C. |
| Atomizing Air Pressure | 2.2 bar |
| Atomizing Air Temperature | 40° C. |
| Spray Rate | 1.00 kg/hr |

Preparation of the Coating Layer
The following liquid coating composition was prepared:

| Ingredients | Amount (%) | Amount (wt % dry) |
|---|---|---|
| Sucrose | 7.5 | 17 |
| $KH_2PO_4$ | 12.6 | 29 |
| $K_2HPO_4$ | 17.2 | 40 |
| Talc | 6.2 | 14 |
| Distilled water | 56.5 | — |
| Total | 100 | 100 |

This liquid coating composition was prepared by dissolving the sucrose and potassium phosphate salts in water and then dispersing the talc (which is added as an anti-agglomeration agent). The mixture was 43.5% dry solids.

The fluid bed was charged with 2.4 kg of the primary particle. Then, 2.8 kg of the liquid coating composition was spray-coated onto the primary particles, using the following process parameters:

| Parameters | Setting |
|---|---|
| Product Air Temperature | 50° C. |
| Inlet Air Temperature | 56° C. |
| Fluidizing Air Flow Rate | 150 m³/hr |
| Spray Temperature | 20° C. |
| Atomizing Air Pressure | 2.2 bar |

| Parameters | Setting |
|---|---|
| Atomizing Air Temperature | 40° C. |
| Spray Rate | 0.50 kg/hr |

After the liquid coating composition has been spray coated on the primary particles, a post-drying step is carried out until a stable humidity value is achieved in the exhaust air. The resultant coated dehydrated microorganism corresponds to sample 11. It has a final composition of: 59% inert core; 8% culture mixture; 33% coating of the invention.

The other related coated dehydrated microorganism of table 1 (samples 10, 12-19, 22-28) were prepared in the same way but using different $1^{st}$ coating composition formula.

Some of the coated dehydrated microrganims were further coated with a conventional outercoating (to get samples 17, 18 and 19. One of the following materials was used:
- SEPIFILM® LP30 composed of Hydroxypropyl methyl cellulose, microcrystalline cellulose, and stearic acid from Seppic (a subsidiary of the Air Liquid Group);
- Shellac (MARCOAT® 125, aqueous based shellac solution (25%), from Innovative Material Technologies);

Particles of samples 4 to 9 were only coated with a conventional outercoating (no hygroscopic salt coating of the invention was added). One of the following materials was used:
- SEPIFILM® LP30;
- Shellac;
- triglycerides (GRINDSTED® PS101 from Danisco),
- STEARINE® TM 50/50 from Exaflor (mixture of stearic acid and palmitic acid 50/50).
- Hydroxypropyl methyl cellulose (HPMC, METHOCEL® E15 from Dow Chemicals).

It would also have been possible to use these other conventional outercoating ingredients:
- Modified starch (LYCOAT® RS780 from Roquette Freres SA or PURE-COTE® from Grain Processing Corporation);
- monoglycerides,
- mixture of mono- and diglycerides,
- fully hydrogenated triglycerides,
- fatty acids,
- hydrocolloids

Example 2

Solid Route-Type Composition

The coated dehydrated microorganisms were prepared in a fluid bed process using a GF-3 (made by Glatt Air Techniques, Binzen, Germany) in bottom-spray mode.

The following liquid coating composition was prepared (same as first coating composition as in example 1):

| Ingredients | Amount (%) | Amount (wt % dry) |
|---|---|---|
| Sucrose | 7.5 | 17 |
| KH$_2$PO$_4$ | 12.6 | 29 |
| K$_2$HPO$_4$ | 17.2 | 40 |
| Talc | 6.2 | 14 |
| Distilled water | 56.5 | — |
| Total | 100 | 100 |

This liquid coating composition was prepared by dissolving the sucrose and potassium phosphate salts in water and then dispersing the talc (which is added as an anti-agglomeration agent). The mixture was about 43% dry solids.

1000 g of the freeze-dried powder of *L. acidophilus* NCFM were charged and fluidized using a heated bed temperature of 55° C. Then, 1180 g of the liquid coating composition according to the invention was spray-coated onto the freeze-dried powder using the following process parameters:

| Parameters | Setting |
|---|---|
| Product Air Temperature | 50° C. |
| Inlet Air Temperature | 60° C. |
| Fluidizing Air Flow Rate | 150 m$^3$/hr |
| Spray Temperature | 20° C. |
| Atomizing Air Pressure | 2.5 bar |
| Atomizing Air Temperature | 40° C. |
| Spray Rate | 0.70 kg/hr |

After the liquid coating composition has been spray coated onto the freeze-dried powder, a post-drying step is carried out until a constant humidity is achieved in the exhaust air.

The resultant coated dehydrated microorganisms had a final composition of: 66% freeze-dried microorganism; 34% coating of the invention. The resultant particle corresponds to sample 20.

The other related coated dehydrated microorganisms of table 1 (namely sample 21) were prepared in the same way but using a different first coating formula.

It is possible to further coat the coated dehydrated microorganisms with a conventional outercoating (not done for samples 20 and 21). The same materials used in Example 1 for the outercoating could be used herein.

Example 3

Thermostability

Heat resistance of dehydrated *L. acidophilus* NCFM coated with a first coating prepared according to Example 1 (liquid route) was compared to dehydrated *L. acidophilus* NCFM coated with conventional coatings: fat (PS101/sunflower oil) or low permeability polymer (Sepifilm LP30). The control consists of uncoated dehydrated *L. acidophilus* NCFM cells.

1 g samples of each preparation were introduced into separate sealed hermetic sachets and kept in a water bath at 50° C.

The sealed hermetic sachet from each preparation was then withdrawn from the water bath after 24 hours and the concentration of viable bacteria was immediately determined after appropriate dilution by standard plating method (Table 2).

TABLE 2

| Sample | Before heat treatment (RT) | After heat treatment (24 hrs/50° C.) | Viability loss (Log) |
|---|---|---|---|
| 1 | $2.50^{E+10}$ | $1.10^{E+09}$ | 1.36 |
| 4 | $1.70^{E+10}$ | $1.72^{E+05}$ | 4.99 |
| 6 | $7.10^{E+09}$ | $3.48^{E+05}$ | 4.31 |
| 11 | $1.40^{E+10}$ | $6.30^{E+09}$ | 0.35 |

RT = room temperature

From the results in Table 2, it can be observed that the coating according to the invention (sample 11) significantly improves thermostability of the dehydrated microorganism compared to the uncoated dehydrated microorganism (sample 1), the dehydrated microorganisms coated with fat coating (sample 4) and the dehydrated microorganisms coated with sepifilm LP30 coating (sample 6).

Moreover, as illustrated in Table 3 below, it can be observed that the coatings $K_2HPO_4$ (48% dry), $KH_2PO_4$ (35% dry), talc (17% dry) and sucrose (0% dry) (sample 10) and $K_2HPO_4$ (40% dry), $KH_2PO_4$ (29% dry), talc (14% dry) and sucrose (17% dry) (sample 11) are more efficient in protecting the bacteria L. acidophilus NCFM from heat. Indeed, the thermostability of these two samples is much greater than:

the thermostability of coated dehydrated microorganism comprising dehydrated microorganism surrounded by a coating comprising a hygroscopic salt in an too low amount, such as sample 12 ($K_2HPO_4$ (14% dry), $KH_2PO_4$ (11% dry), talc (22% dry) and sucrose (54% dry)).

or the thermostability of coated dehydrated microorganism comprising dehydrated microorganism surrounded by a coating that does not comprise any hygroscopic salt (samples 13 and 14 comprise only a non hygroscopic salt, sodium sulphate and magnesium sulphate respectively)

TABLE 3

| Sample | Before heat treatment (RT) | After heat treatment (24 hrs/50° C.) | Viability loss (Log) |
| --- | --- | --- | --- |
| 10 | $1.00^{E+10}$ | $2.80^{E+09}$ | 0.55 |
| 11 | $1.40^{E+10}$ | $6.30^{E+09}$ | 0.35 |
| 12 | $5.00^{E+09}$ | $2.60^{E+07}$ | 2.28 |
| 13 | $5.50^{E+09}$ | $1.90^{E+06}$ | 3.46 |
| 14 | $5.50^{E+09}$ | $2.80^{E+06}$ | 3.29 |

RT = room temperature

The samples were also tested under more stringent conditions, e.g. 64° C. for 18 hours in order to better discriminate between the salt coatings providing high thermoprotection versus those providing lower thermoprotection.

TABLE 4

| Sample | Before heat treatment (RT) | After heat treatment (18 hrs/ 64° C./) | Viability loss (Log) |
| --- | --- | --- | --- |
| 26 | 1.61E+10 | 4.81E+09 | 0.5 |
| 27 | 1.20E+10 | 2.70E+09 | 0.6 |
| 28 | 1.90E+10 | 5.00E+09 | 0.6 |
| 11 | 3.85E+09 | 1.60E+08 | 1.4 |
| 25 | 1.49E+09 | 4.60E+07 | 1.5 |
| 12 | 2.88E+09 | 3.30E+06 | 2.9 |
| 13 | 3.38E+09 | 1.30E+06 | 3.4 |
| 16 | 9.30E+08 | <10 000 | >5.0 |
| 14 | 1.48E+09 | <10 000 | >5.2 |
| 15 | 2.20E+09 | <10 000 | >5.3 |

As can be seen from Table 4, it can be observed that the following coatings $K_2HPO_4$ (30% dry), sodium acetate tri hydrate (30% dry), talc (14% dry) and sucrose (17% dry) (sample 26);

$K_2HPO_4$ (83%) talc (17%) and, pH adjusted to 6.5 (sample 27);

$KH_2PO_4$ (83%) talc (17%) and, pH adjusted to 6.5 (sample 28); and $K_2HPO_4$ (40% dry), $KH_2PO_4$ (29% dry), talc (14% dry) and sucrose (17% dry) (sample 11), $MgCl_2$ (100% dry) (sample 25)

are very efficient in protecting the bacteria L. acidophilus NCFM from heat.

On the contrary, coated bacteria L. acidophilus NCFM surrounded by a coating which either does not contain any hygroscopic salt (samples 13 and 14) or which contain hygroscopic salts in an insufficient amount (sample 12) or which does not have the suitable pH (samples 15 and 16) were much less resistant to heat compared to samples 25, 26, 27, 28 and 11.

Example 4

Stability During Recombined Cheese Processing

The recombined cheese trial involved the following steps:
i) grinding of the curd,
ii) addition of hydrocolloids (no melting salts) to give the right texture to the final product,
iii) heating to 60° C., and
iv) stirring at 60° C.

Samples of uncoated (control) or coated L. acidophilus NCFM were added to the molten mixture under stirring at 60° C. The stirring was continued for about 1 minute and followed by the moulding phase. Finally the moulded recombined cheese containing L. acidophilus NCFM was rapidly cooled down. The viability of the coated dehydrated L. acidophilus NCFM in the recombined cheese process was then evaluated and compared against uncoated dehydrated L. acidophilus NCFM (control). Results are presented in Table 5.

TABLE 5

| Sample | Before heat treatment (RT) | After heat treatment (60° C., 1 min) | Survival to process | Viability loss in process (Log) | Protection factor over control |
| --- | --- | --- | --- | --- | --- |
| 2 | $1.00^{E+08}$ | $1.00^{E+04}$ | 0.01% | 4.0 | n.a. |
| 5 | $1.00^{E+07}$ | $1.00^{E+03}$ | 0.01% | 4.0 | 0 |
| 8 | $7.92^{E+06}$ | $8.00^{E+04}$ | 1.0% | 2.0 | 10 |
| 9 | $1.00^{E+07}$ | $2.00^{E+05}$ | 2.0% | 1.7 | 20 |
| 17 | $4.94^{E+06}$ | $1.20^{E+06}$ | 24.1% | 0.6 | 2431 |
| 18 | $1.15^{E+07}$ | $4.00^{E+06}$ | 34.9% | 0.5 | 3491 |

RT = room temperature,
n.a. non applicable (control)

From the experiment, it can be observed that the coated dehydrated microorganism comprising dehydrated microorganism surrounded by a first coating composed of the coating of the invention and with an outercoating comprising a polymer (samples 17 and 18) have a significantly enhanced survival rate following the recombined cheese processing. Moreover, they also have an improved stability over the uncoated bacteria (sample 2), the fat-coated bacteria (sample 5), the polymer-coated bacteria (sample 8) and the fat-coated+polymer-subcoated bacteria (sample 9). This shows the efficiency of the coating according to the invention.

Example 5

Feed Pelleting Stability

Dehydrated L. acidophilus NCFM or L. plantarum Lp115 coated with a first coating consisting of a coating according to the invention followed by a polymer outercoating were pelletized using harsh conditions (see below). The stability of these bacteria following pelletization was compared to that of the uncoated dehydrated L. acidophilus NCFM or L. plantarum Lp115 (controls).

Specifically, each test sample (i.e. 240 g of coated dehydrated bacteria) was mixed into 10 kg of premix feed and mixed for 10 min. This 10 kg premix feed (containing the 240 g of coated dehydrated bacteria) was then added to 150 kg of feed in a large horizontal mixer and mixed for 15 min before conditioning. The feed was then treated for 30 seconds at 75°

C. by injecting "dry steam" (i.e. 3.5 to 4.5% wt water) directly into the feed prior to feed pelletization. The feed pellets were obtained using a 3 mm dye. The pellets were then cooled by blowing air around them using a fan. After 5 minutes, the temperature was lowered to 30° C. After 15 additional minutes, the temperature was again lowered to room temperature. At this stage, the pellets had a dry matter content (% DM) of about 80-90% and aw>0.10. The concentration of viable bacteria remaining after pelletization was subsequently determined by standard plating methods.

Composition of the Premix Feed (Corn-Based Feed)

| Corn Diet Ingredients | Percent |
| --- | --- |
| Corn | 61.01% |
| Soybean meal 48 | 31.52% |
| Soy oil | 4.00% |
| Sodium bicarbonate | 0.40% |
| DL Methionine | 0.20% |
| Limestone | 1.16% |
| Dicalcium Phos | 1.46% |
| VIT/MIN Beta Avitren 90 | 0.25% |
| TOTAL | 100.00% |

TABLE 6

| Sample | Before heat treatment (RT) | After heat treatment (60° C., 1 min) | Viability loss in processing (Log) | Protection factor over control |
| --- | --- | --- | --- | --- |
| 2 | $2.70^{E+08}$ | $3.79^{E+05}$ | 3.00 | n.a. |
| 17 | $1.48^{E+05}$ | $9.90^{E+03}$ | 1.6 | 18 |
| 3 | $6.90^{E+05}$ | $1.56^{E+05}$ | 3.6 | n.a. |
| 19 | $3.23^{E+05}$ | $1.04^{E+04}$ | 0.96 | 545 |

RT = room temperature,
n.a. non applicable (control)

As can be observed in Table 6 above, the stability of the dehydrated bacteria coated with the coating according to the invention (samples 17 and 19) following pellitization was enhanced compared to the uncoated dehydrated bacteria (samples 2 and 3).

Example 6

Stability in Intermediate Moisture Powder

The viability of dehydrated *L. acidophilus* NCFM in freeze-dried form (control) and as coated dehydrated *L. acidophilus* NCFM (made by the liquid route) has been studied in the following conditions:
Maltodextrine powder Glucidex IT6 from Roquette initially having a water activity (aw) equal to 0.2, was exposed to an environment in which the relative humidity was 40% until the 'aw' of the maltodextrine reached and equilibrated at an aw=0.4.

The bacteria preparation was mixed into the maltodextrin powder (aw=0.4) at a ratio of 10% wt of coated bacteria and 90% wt of maltodextrin powder. 10 g of the mixture was then placed into glass vials which were subsequently sealed with a moisture proof cap. The vials were kept at 30° C. in an incubator. Each month, a vial of the mixture was analyzed for its content of viable cells by standard plating methods. The results are listed in Table 7. The concentration of viable cells is expressed as CFU/g and as a percentage of the concentration of each samples at T=0.

TABLE 7

| Sample | T = 0 | 1 month | % survival | Protection factor over control |
| --- | --- | --- | --- | --- |
| 2 | $1.50^{E+11}$ | $6.80^{E+09}$ | 5% | n.a. |
| 10 | $8.80^{E+09}$ | $1.56^{E+09}$ | 18% | 4 |
| 11 | $1.40^{E+10}$ | $9.00^{E+09}$ | 64% | 13 |
| 15 | $1.90^{E+09}$ | $1.08^{E+08}$ | 6% | 1 |
| 16 | $5.10^{E+09}$ | $6.65^{E+07}$ | 1% | 0 | n.a. non applicable (control)

The coating comprising a hygroscopic salt such as $K_2HPO_4$ but with an uncompatible pH (sample 15) or comprising a non hygroscopic salt such as $KH_2PO_4$ (sample 16) offers no benefits or very limited benefits, whereas the coating according to the present invention (samples 10 and 11) clearly improve the viability of the dehydrated *L. acidophilus* NCFM at intermediate moisture and provide an increase in stability up to 13 times over uncoated dehydrated *L. acidophilus* NCFM (see Table 7). See example 13 showing the effect of the pH on $K_2HPO_4$ coating.

Example 7

Stability in Nutritional Bar

Granola® bars were prepared as follows:
hydrating pectin (GRINDSTED Pectin CF 140 B) in hot water under high agitation,
blending it together with corn syrup (42 DE Corn Syrup) and sugar,
heating the pectin slurry-corn syrup+sugar mixture to 106° C. (~12.5% water loss, 82% dry matter) to make the binding syrup,
cooling the binding syrup to 55° C.,
pouring 410 g of the cooled binding syrup over 590 g of Cascadian Farms® granola cereal, and mixing thoroughly,
rolling out the preparation between two sheets of oiled parchment paper and allowing to cool,
cutting the rolled out preparation into 34 g bars (each bar having a moisture content=8.1% and an aw=0.5 at the time of manufacture),
melting chocolate and adding the test samples containing the bacteria *L. acidophilus* NCFM in the chocolate at 28° C.,
depositing 6 g of the chocolate-bacteria mixture onto the bar (i.e. 6 g chocolate-bacteria mixture onto approximately 34 g of granola bar).
the bars with the chocolate-bacteria mix were stored at 23° C. (tables 8 and 9) or 30° C. (table 10) and the concentration of viable cells was measured after a storage period of 1, 2, 3, 5, 9 and 12 months at 23° C. or at 30° C., by standard plating methods.

TABLE 8

| Sample | Aw at Time 0 | Time 0 | 1 Month | 2 Months | 3 Months | 5 Months | Protection factor over control |
| --- | --- | --- | --- | --- | --- | --- | --- |
| 2 | 0.51 | $9.93^{E+09}$ (100%) | $5.10^{E+09}$ (51%) | $3.86^{E+09}$ (39%) | $1.21^{E+09}$ (12%) | $8.02^{E+08}$ (8%) | n.a. |
| 4 | n.a. | $1.33^{E+10}$ (100%) | $6.54^{E+09}$ (49%) | $3.29^{E+09}$ (25%) | $1.63^{E+09}$ (12%) | $2.14^{E+08}$ (1.6%) | 0 |
| 6 | n.a. | $1.02^{E+10}$ (100%) | $5.98^{E+09}$ (58%) | $2.80^{E+09}$ (27%) | $1.06^{E+09}$ (10%) | $2.32^{E+08}$ (2%) | 0 |

TABLE 8-continued

| Sample | Aw at Time 0 | Time 0 | 1 Month | 2 Months | 3 Months | 5 Months | Protection factor over control |
|---|---|---|---|---|---|---|---|
| 7 | 0.54 | $1.16^{E+10}$ (100%) | $1.05^{E+10}$ (90%) | $5.51^{E+09}$ (47%) | $1.74^{E+09}$ (15%) | $5.72^{E+08}$ (5%) | 0 | n.a. non applicable (control)

The results in Table 8 shows that when stored at 23° C., the viability of dehydrated *L. acidophilus* NCFM coated with conventional coatings such as fat (sample 4), low permeability polymer Sepifilm LP30 (sample 6) or shellac (sample 7) as previously described in the prior art is not maintained, the concentration of viable cells decreasing more than 1.5 LOG over a 5 months storage at 25° C. in granola bars and providing no improved stability over the uncoated dehydrated bacteria (sample 2).

As some final products have a water activity "aw" which could be lower, a similar experiment was conducted, but with a reduced aw, giving somewhat dryer conditions.

TABLE 9

| Sample | aw at T = 0 | T = 0 | 1 Month | 2 Months | 3 Months | 5 Months | 9 Months | 12 Months | *Protection factor over the control |
|---|---|---|---|---|---|---|---|---|---|
| 2 | 0.35 | $5.91^{E+09}$ (100%) | $4.43^{E+09}$ (75%) | $3.48^{E+09}$ (59%) | $7.76^{E+09}$ (30%) | $9.36^{E+08}$ (16%) | $1.29^{E+08}$ (2%) | $1.34^{E+08}$ (2%) | n.a. |
| 11 | 0.36 | $5.56^{E+09}$ (100%) | $3.41^{E+09}$ (61%) | $4.25^{E+09}$ (76%) | $3.83^{E+09}$ (69%) | $3.36^{E+09}$ (60%) | $3.88^{E+09}$ (70%) | $3.36^{E+09}$ (60%) | 35 |
| 17 | 0.31 | $8.46^{E+09}$ (100%) | $6.93^{E+09}$ (82%) | $6.69^{E+09}$ (79%) | $6.75^{E+09}$ (80%) | $3.56^{E+09}$ (42%) | $2.96^{E+09}$ (35%) | not measured | 27 |
| 18 | 0.32 | $8.58^{E+09}$ (100%) | $5.65^{E+09}$ (66%) | $5.02^{E+09}$ (59%) | $5.36^{E+09}$ (62%) | $4.00^{E+09}$ (47%) | $3.53^{E+09}$ (41%) | $3.42^{E+09}$ (40%) | 20 | n.a. non applicable (control)
*Protection factor calculated at 9 month-storage, 25° C.

Results from Table 9 show that when stored at 23° C., presence of the coating according to the invention (samples 11, 17 and 18) results in improved bacteria stability over uncoated dehydrated bacteria (sample 2). Sample 11 offers the greatest protection over a long-time period (12 months).

Figure 2:
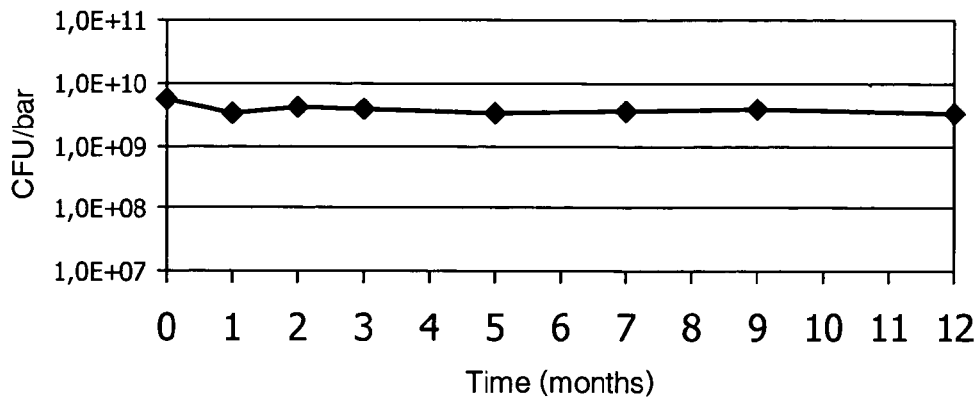
FIG. 2 A is a survival graph of coated (sample 11) $L.$ $acidophilus$ NCFM into chocolate bar stored at 23° C. Composition of sample 11: $K_2HPO_4$ (40% dry), $KH_2PO_4$ (29% dry), sucrose (17% dry), talc (14% dry).
Figure 2:
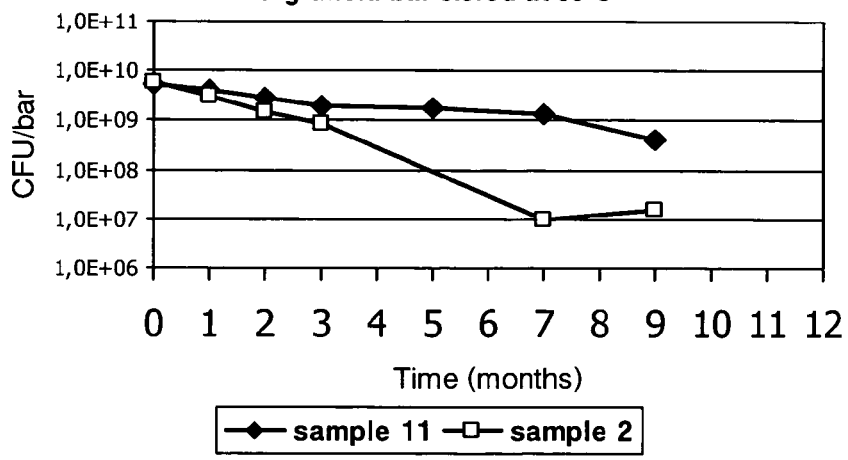

After 12 months storage at 23° C. in the chocolate coating of the Granola® bar, the viability of *L. acidophilus* NCFM coated with the coating according to the invention remains high, for example, a viability of 60% is obtained after 12 months of storage with sample 11 (see FIG. 2 A).

When stored at 30° C., the protection offered by the coating of the present invention (samples 11, 17 and 18) was significantly enhanced compared to the uncoated dehydrated bateria (sample 2).

After 9 months storage at 30° C. in the chocolate coating of the Granola® bar, the viability of *L. acidophilus* NCFM coated with the coating(s) according to the invention is significantly higher than the one obtained with uncoated microorganisms, for example, it is 1.5 LOG or 24 times higher after 9 months of storage with sample 11 (see FIG. 2 B). It is more than 2 LOG or more than 80 times higher for samples 17 and 18.

In Table 11, the tested samples containing the microorganisms *L. acidophilus* were added directly into the cooled binding syrup and Cascadian Farms® granola cereal, and mixed thoroughly, before making the bars and storing them at ambiant temperature. After a six-month storage, the stability of the *L. acidophilus* NCFM coated with the coating according to the invention (sample 11) was improved by a factor of 300 over uncoated bacteria.

TABLE 11

| Sample | aw at T = 0 | T = 0 | 1 Month | 3 Months | 6 Months | *Protection factor over the control |
|---|---|---|---|---|---|---|
| 2 | 0.32 | $3.15^{E+08}$ (100%) | $2.23^{E+08}$ (71%) | $2.77^{E+07}$ (9%) | $8.83^{E+05}$ (0.3%) | n.a. |
| 11 | 0.32 | $1.78^{+08}$ (100%) | $2.14^{+08}$ (100%) | $2.51^{E+08}$ (100%) | $1.55^{E+08}$ (87%) | 290 | n.a. non applicable (control)
*Protection factor calculated at 6 month-storage, 25° C.

TABLE 10

| Sample | aw at T = 0 | T = 0 | 1 Month | 2 Months | 3 Months | 5 Months | 7 Months | 9 Months | *Protection factor over the control |
|---|---|---|---|---|---|---|---|---|---|
| 2 | 0.35 | $5.91^{E+09}$ (100%) | $3.15^{E+09}$ (53%) | $1.51^{E+09}$ (26%) | $9.00^{E+08}$ (15%) | $1.66^{E+06}$ (0.03%) | $9.50^{E+06}$ (0.2%) | $1.52^{E+07}$ (0.3%) | n.a. |
| 11 | 0.36 | $5.56^{E+09}$ (100%) | $4.23^{E+09}$ (76%) | $2.92^{E+09}$ (53%) | $2.05^{E+09}$ (37%) | $1.81^{E+09}$ (33%) | $1.35^{E+09}$ (24%) | $4.36^{E+08}$ (7.3%) | 24 |
| 17 | 0.31 | $8.46^{E+09}$ (100%) | $5.6^{E+09}$ (66%) | $1.60^{E+09}$ (19%) | $2.58^{E+09}$ (31%) | $5.82^{E+08}$ (7%) | Not measured | $2.99^{E+09}$ (35.3%) | 117 |
| 18 | 0.32 | $8.58^{E+09}$ (100%) | $4.905^{E+09}$ (57%) | $2.14^{E+09}$ (25%) | $2.49^{E+09}$ (29%) | $4.36^{E+08}$ (5%) | $2.68^{E+09}$ (20%) | $2.07^{E+09}$ (24%) | 80 | n.a. non applicable (control)
*Protection factor calculated at 9 month-storage, 30° C.

Example 8

Stability in SlimFast® Optima French Vanilla Shake Mix

The viability of L. acidophilus NCFM in freeze-dried form (sample 2) and in the coated particles (samples 11, 17 and 18) has been studied in the following conditions:

The test samples were blended into SlimFast® powder (commercial SlimFast® Optima French Vanilla shake mix with aw=0.35) at a ratio of test sample to Slimfast® powder of 1:10.

The mixtures were then divided into 10 g samples in separate sealed hermetic sachets.

The sachets were kept in an incubator at 30° C.

At time 0 and after 3, 6, 9 and 12 months storage at 30° C., a sachet of each blend was analysed for the content of viable cells, by standard plating methods.

TABLE 12

| Sample | Aw T = 0 | T = 0 | 3 Months | 6 Months | 9 Months | 12 Months | *Protection factor over the control |
|---|---|---|---|---|---|---|---|
| 2 | 0.35 | $2.5^{E+10}$ (100%) | $1.22^{E+10}$ (49%) | $2.2^{E+09}$ (9%) | $2.5^{E+08}$ (1%) | $1.1^{E+07}$ (0.04%) | n.a. |
| 11 | 0.36 | $1.37^{E+09}$ (100%) | $8.63^{E+08}$ (63%) | $5.03^{E}+08$ (36%) | $2.3^{E+08}$ (17%) | $7.0^{E+07}$ (5.1%) | 128 |
| 17 | 0.31 | $8.46^{E+09}$ (100%) | $6.93^{E+09}$ (82%) | $2.23^{E}+08$ (29%) | $1.28^{E+08}$ (17%) | $4.2^{E+07}$ (5.3%) | 132 |
| 18 | 0.32 | $8.58^{E+09}$ (100%) | $5.65^{E+09}$ (66%) | $4.23^{E+07}$ (6%) | $8.03^{E+06}$ (1%) | $1.8^{E+06}$ (0.25%) | 6 | n.a. non applicable (control)
*Protection factor calculated at 12 month-storage, 30° C.

The results from Table 12 show that the presence of the coating according to the invention (samples 11, 17 and 18) results in improved stability over uncoated dehydrated bacteria (sample 2).

Example 9

Moisture Uptake Rate (MUR) Determination

Glass desiccators containing saturated salt solutions of NaCl (in order to adjust the enclosed salt to 75% RH) were stored at 25° C. Various samples in open trays were loaded in the desiccators and incubated over time.

The weight of the test material used is adjusted in order to ensure accurate weighing (e.g sample mass>2 grams) as well as a low sample thickness (e.g. less than 1 cm) to avoid moisture content heterogeneity within the test sample.

For example, the MUR test on $K_2HPO_4$ salt was done by adding 4.7 grams of $K_2HPO_4$ salt in a plastic tray. The plastric tray had the following charactistics:

Mass of the tray: 3.4 grams
Area of the tray: 10.2 cm2 (circular tray with a diameter of 3.6 cm)
Height of the tray: 1.5 cm For MUR experiments, the circular plastic tray is filled to half of its height with the sample to be tested. Subsequently, the moisture absorption of the sample was determined by weighing the samples before and during the incubation period at various time intervals. The MUR was determined for each measurement according to the equation 1.

$MUR(t)$ in %=$(mt-mt0)/mt0$    Equation 1:

MUR (t): percentage of the water uptake
mt0: initial mass of sample
mt: mass of sample at the measurement time Table 13 gives the moisture uptake rate (MUR) of various salts after 2, 5 and 7 days exposure at 25° C. and 75% RH:

TABLE 13

Moisture uptake rate (MUR) of various salts measured at 75% RH, 25° C. at 2, 5 and 7 days (% moisture of the salt weight)

| Salts | 2 Days | 5 Days | 7 Days |
|---|---|---|---|
| Calcium chloride (CaCl2) | 36.2% | 63.4% | 88.3% |
| Sodium acetate anhydrous (CH3COONa) | 36% | 54% | n.m. |
| Magnesium chloride (MgCl$_2$) | 18.7% | 41.8% | 53.7% |
| Potassium carbonate (K$_2$CO$_3$) | 21.1% | 37.9% | 50.7% |
| Dipotassium phosphate (K$_2$HPO$_4$) | 21.0% | 36.5% | 45.6% |
| Magnesium sulfate (MgSO$_4$) | 0.1% | 0.2% | 0.2% |
| Calcium lactate (CH$_3$CHOHCOOCa) | 0.4% | 0.7% | 0.7% |
| Sodium sulfate (Na$_2$SO$_4$) | 0.0% | 0.0% | 0.1% |
| Calcium carbonate (CaCO$_3$) | 0.0% | 0.1% | 0.1% |
| Monopotassium phosphate (KH$_2$PO$_4$) | 0.0% | 0.0% | 0.0% |
| Sodium acetate trihydrate ((CH$_3$COO)$_2$Na•3H2O) | 0.0% | 0.0% | 0.0% |
| Tri-sodium citrate dihydrate (HOC(COONa)(CH$_2$COONa)$_2$) | −0.1% | −0.2% | −0.2% |

It can be concluded from this table that calcium chloride (CaCl$_2$), sodium acetate anhydrous (CH$_3$COONa), magnesium chloride (MgCl$_2$) dipotassium phosphate (K$_2$HPO$_4$), potassium carbonate (K$_2$CO$_3$), and are considered as hygroscopic salts according to this invention as they have MUR values (25° C., 75% RH) at 7 days significantly above to 20% w/w.

It can be concluded also from the same table that magnesium sulfate (MgSO$_4$), calcium lactate ((CH$_3$CHOHCOOCa), sodium sulfate (Na$_2$SO$_4$), calcium carbonate (CaCO$_3$), monopotassium phosphate (KH$_2$PO$_4$), sodium acetate tri hydrate ((CH$_3$COO)$_2$Na.3H$_2$O) and tri-sodium citrate dihydrate (HOC(COONa)(CH$_2$COONa)$_2$) are considered as non hygroscopic salts according to this invention as they have MUR values (25° C., 75% RH) at 7 days significantly less than 20% w/w.

Figure 3:
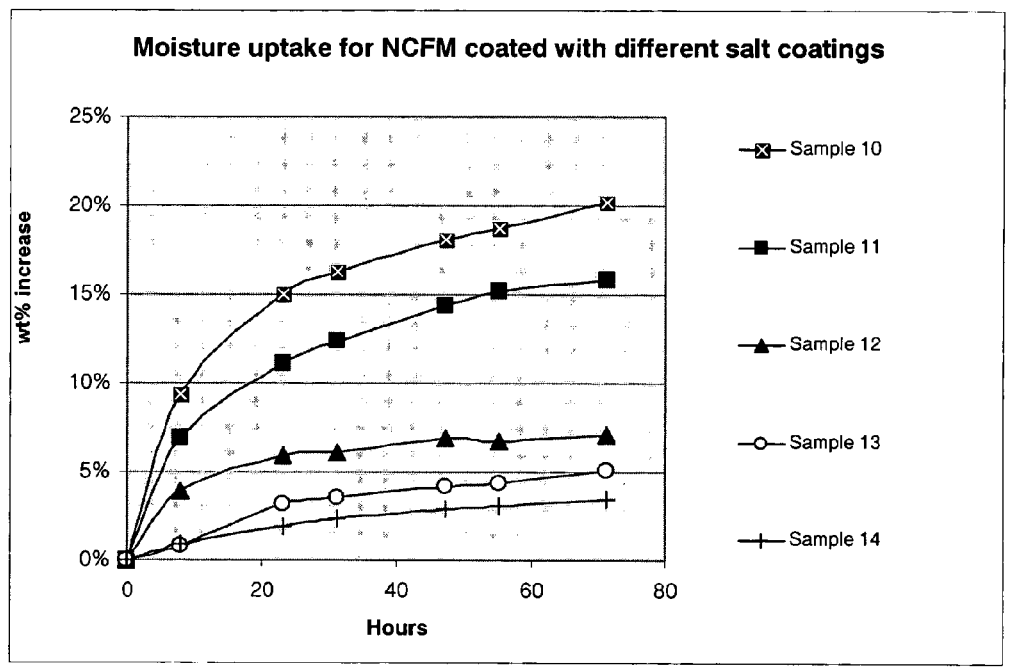
FIG. 3 is a moisture uptake graph for coated $L.$ $acidophilus$ NCFM at 75% RH and 37° C. All are dehydrated $L.$ $acidophilus$ NCFM prepared via the liquid route and surrounded by a coating of: Sample 10: $K_2HPO_4$ (48% dry), $KH_2PO_4$ (35% dry), sucrose (0% dry), talc (17% dry). Sample 11: $K_2HPO_4$ (40% dry), $KH_2PO_4$ (29% dry), sucrose (17% dry), talc (14% dry). Sample 12: $K_2HPO_4$ (14% dry), $KH_2PO_4$ (11% dry), sucrose (54% dry), talc (22% dry). Sample 13: $Na_2SO_4$. Sample 14: $MgSO_4$.

FIG. 3 shows the moisture uptake rate of coated dehydrated microorganisms samples. Glass desiccators containing saturated salt solutions of NaCl (in order to adjust the coated dehydrated microorganisms samples to 75% RH) were stored at 37° C. Various samples in open trays were loaded in the desiccators and incubated for 3 days. Subsequently, the moisture absorption of the samples was determined by weighing the samples before and during the incubation period at various time intervals. FIG. 3 shows the % weight gain of the coated dehydrated microorganisms as a function of time at 75% RH and 37° C. for 3 days.

It can be concluded from FIG. 3, that a coating which contains either 40% or 48% hygroscopic salt ($K_2HPO_4$) (samples 10 and 11) is better suited to absorb moisture, than a coating comprising only 14% hygroscopic salt ($K_2HPO_4$) and 76% optional other ingredients (talc and sucrose) (sample 12). This difference in moisture absorption is related to amount of hygroscopic salts and/or to the structure of the coating containing the hygroscopic salts, e.g. to the partially crystalline degree of the coating once processed. Coatings with a too low amount of hygroscopic salt (i.e. under 25%) at the expense of a too high optional other ingredients content (i.e. above 70%, sample 12) or coatings using only non hygroscopic salts (i.e. $Na_2SO_4$ in sample 13, $MgSO_4$ in sample 14), are inefficient to absorb adequate amounts of moisture.

Example 10

X-Ray Powder Diffractometry

Investigation into the nature of salt coatings as it relates to the stabilization effects on dehydrated microorganisms. The "crystalline" vs "amorphous" nature of the different salt coating has been determined using X-ray diffraction analysis.

Description of Method:

An XRD-powder analysis is made by placing the material in the sample holder and the upper surface is levelled. The sample is placed in the X-ray diffractometer, where X-rays are focussed upon it. The X-rays are scattered depending on the arrangement of atoms in the sample. If the atoms are arranged in an ordered, repeating structure, as in crystals, the XRD pattern will show a series of sharp peaks. As every crystalline material produces a unique X-ray diffraction pattern, it is possible to determine the composition of a sample by subtracting known components from the sample pattern and then comparing the residual pattern with those in a library (e.g. The International Centre for Diffraction Data (ICDD) reference collection) or known reference patterns.

Coated Dehydrated Microorganism:

- Coated dehydrated microorganism obtained by the liquid route, wherein the coating is $K_2HPO_4$ (48% dry), $KH_2PO_4$ (35% dry), talc (17% dry) and 0% sucrose, co-processed by spray-coating (sample 10) (FIG. 4—weakly crystalline).
- Coated microorganism obtained by the liquid route, wherein the coating is $K_2HPO_4$ (40% dry), KH2PO4 (29% dry), talc (14% dry) and sucrose (17% dry), co-processed by spray-coating (sample 11) (FIG. 5—weakly crystalline, salts not crystalline).
- Coated microorganism obtained by the liquid route, wherein the coating is $K_2HPO_4$ (14% dry), $KH_2PO_4$ (11% dry), talc (22% dry) and sucrose (54% dry) co-processed by spray-coating (sample 12) (FIG. 6—weakly crystalline, small amount of crystalline sucrose as anhydrate, salts not crystalline)
- Coated micro-organism prepared by the liquid route but with a coating of one non hygroscopic salt ($KH_2PO_4$) with talc co-processed by spray-coating (sample 16) (FIG. 7—Predominantly crystalline)
- Coated microorganism obtained by the solid route, wherein the coating is $K_2HPO_4$ (40% dry), $KH_2PO_4$ (29% dry), talc (14% dry) and sucrose (17%), co-processed by spray-coating (sample 20) (FIG. 8—weakly crystalline, thus largely amorphous)
- Coated microorganism obtained by the solid route, wherein the coating is $Na_2SO_4$, co-processed by spray-coating (sample 21) (FIG. 9—largely crystalline, thus weakly amorphous).

The physical state of the coating produced according to the invention is shown to be partially crystalline. At high sucrose content (sample 12), the salts and sucrose mixture show the onset of sucrose crystallization, but there is no salt crystallization. However, as shown from FIG. 3, high sucrose content coatings (e.g. sample 12) reduced the MUR of the coated layer and therefore the benefits conferred by the low crystallinity solid state is significantly reduced.

Example 11

Degree of Crystallinity and Glass Transition Temperature by Differential Scanning Calorimetry (DSC)

Method:

The glass transition temperature of the coating and degree of crystallinity of the salt(s) in the coating of the present invention were obtained using DSC. A Netzch DSC 204 (Netzsch, Germany) equipped with an intracooler was used for all measurements with $N_2$ as flushing agent. Samples of 10 mg were weighed into standard aluminium pans as quickly as possible to avoid water sorption. The pans were sealed and each sample was cooled and held at an initial temperature of −50° C. for 2 minutes. The samples were then heated from −50° C. to 330° C. at 12° C. $min_{-1}$ and held at 330° C. for 3 minutes.

Preparation of Samples:

Tests were performed on the dried coating produced under the same process conditions as those used to apply the coating onto the dehydrated microorganisms of the present invention. The coating analyzed in this test was not applied onto the primary particle to avoid interference from the core. Indeed, peaks from the core material were found to occur at the same temperature as some of the peaks of the coating materials 30 wt % aqueous solutions of the mono-potassium phosphate ($KH_2PO_4$) dipotassium phosphate ($K_2HPO_4$) and mixture of 45% $K_2HPO_4$, 35% $KH_2PO_4$, and 20% sucrose were prepared and each solution was atomized and dried in the fluid-bed, resulting respectively in sample A, B and C Table 14 described the composition of the dried salt coatings (samples A, B and C) analysed by DSC and Table 15 summarizes the process parameters used to these samples. The samples were post-dried for 15 min at product temperature of 55° C.

TABLE 14

| Sample | Dried salt coating composition $KH_2PO_4$ (dry wt %) | $K_2HPO_4$ (dry wt %) | Sucrose (dry wt %) |
|---|---|---|---|
| A | 100% | | |
| B | | 100% | |
| C | 35% | 45% | 20% |

TABLE 15

| Process parameters | Values |
|---|---|
| Step-up | Bottom spray |
| Nozzle | 1.2 mm |
| Inlet temperature | 70° C. |
| Product temperature | 55° C. |
| Atomization pressure | 3.5 bars |
| Air Flow | 120 m3/h |

Figure 10:
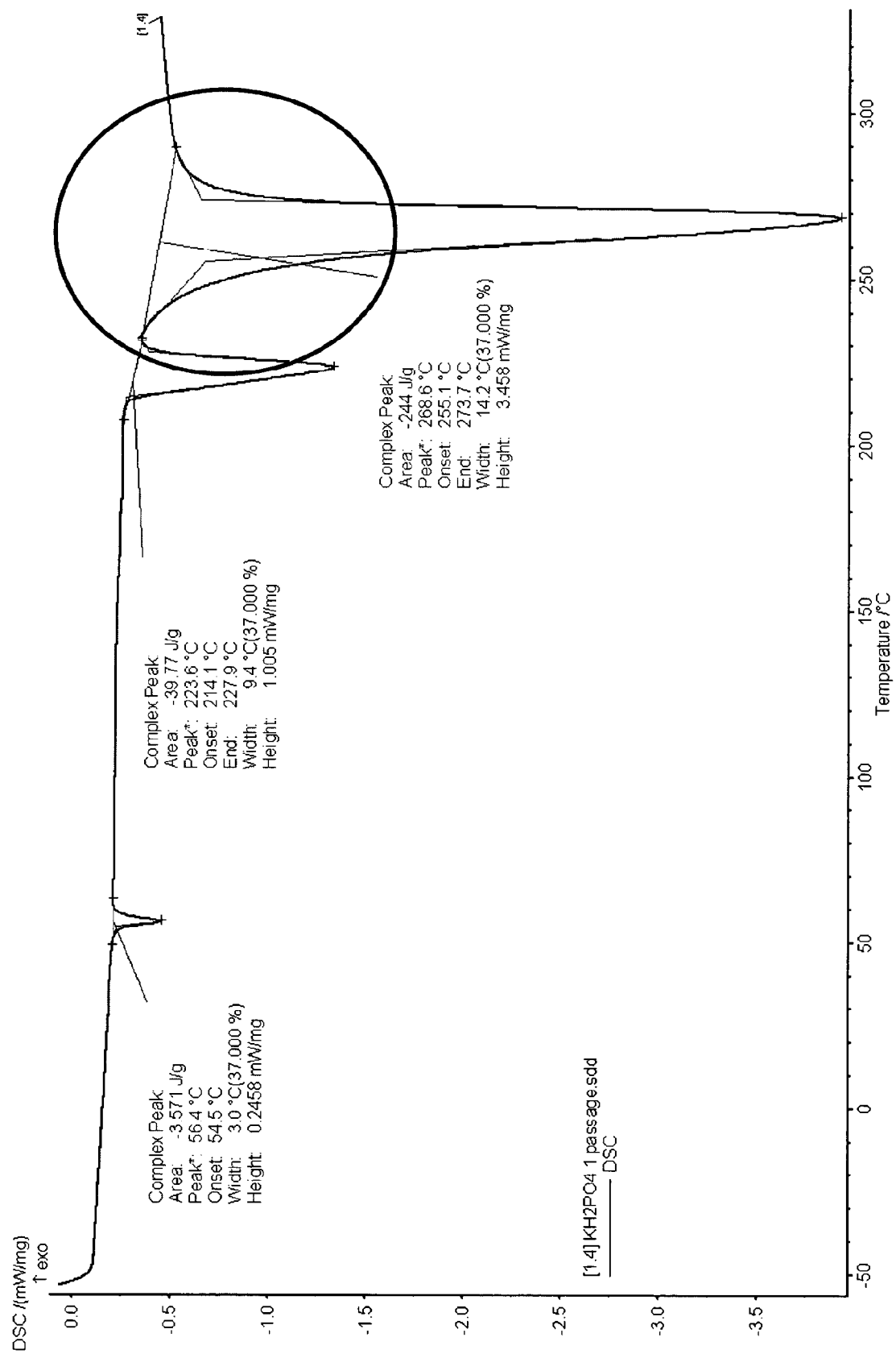
FIG. 10 is a DSC thermogram for sample A ($KH_2PO_4$).
Figure 11:
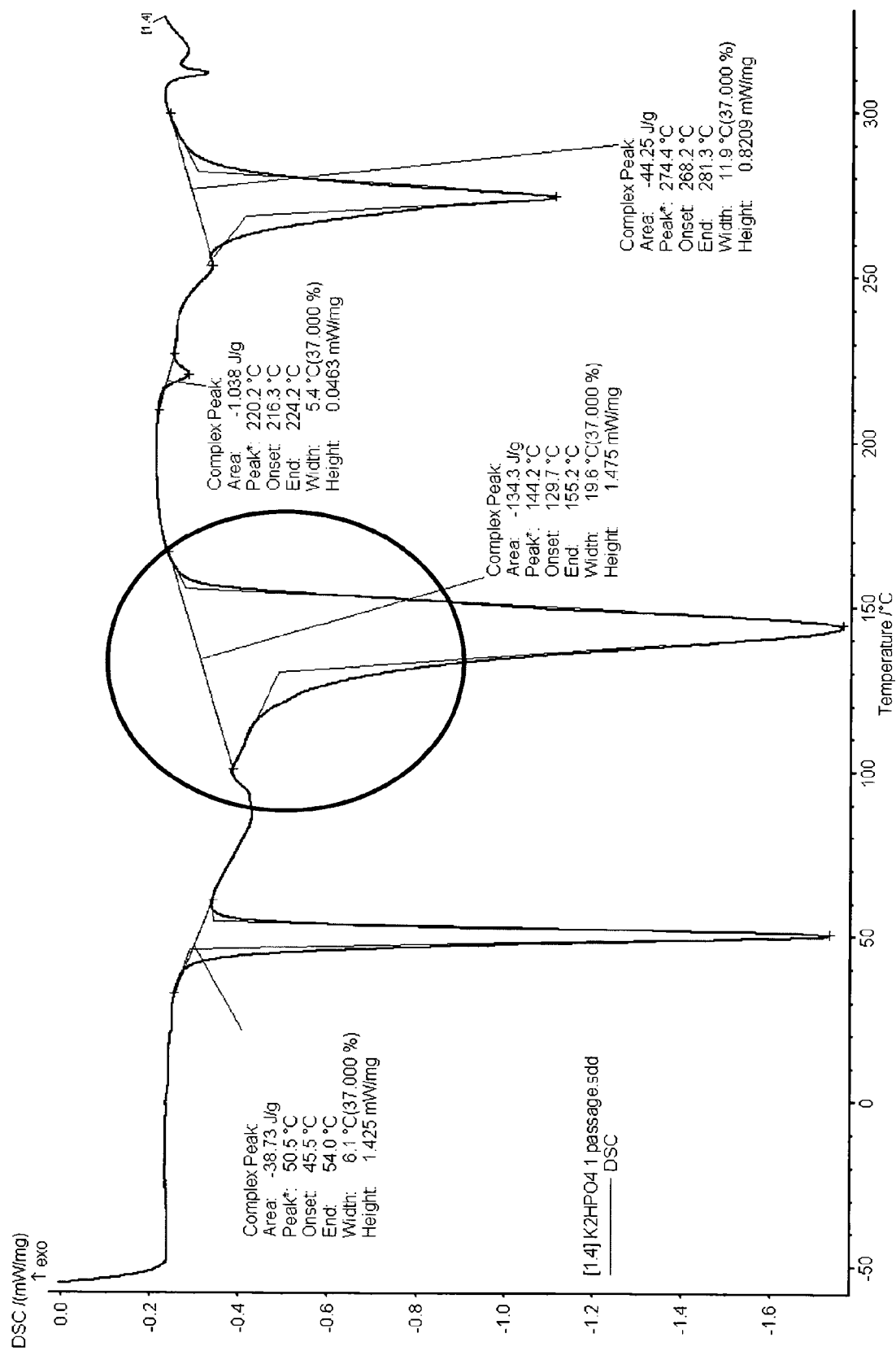
FIG. 11 is a DSC thermogram for sample B ($K_2HPO_4$).
Figure 12:
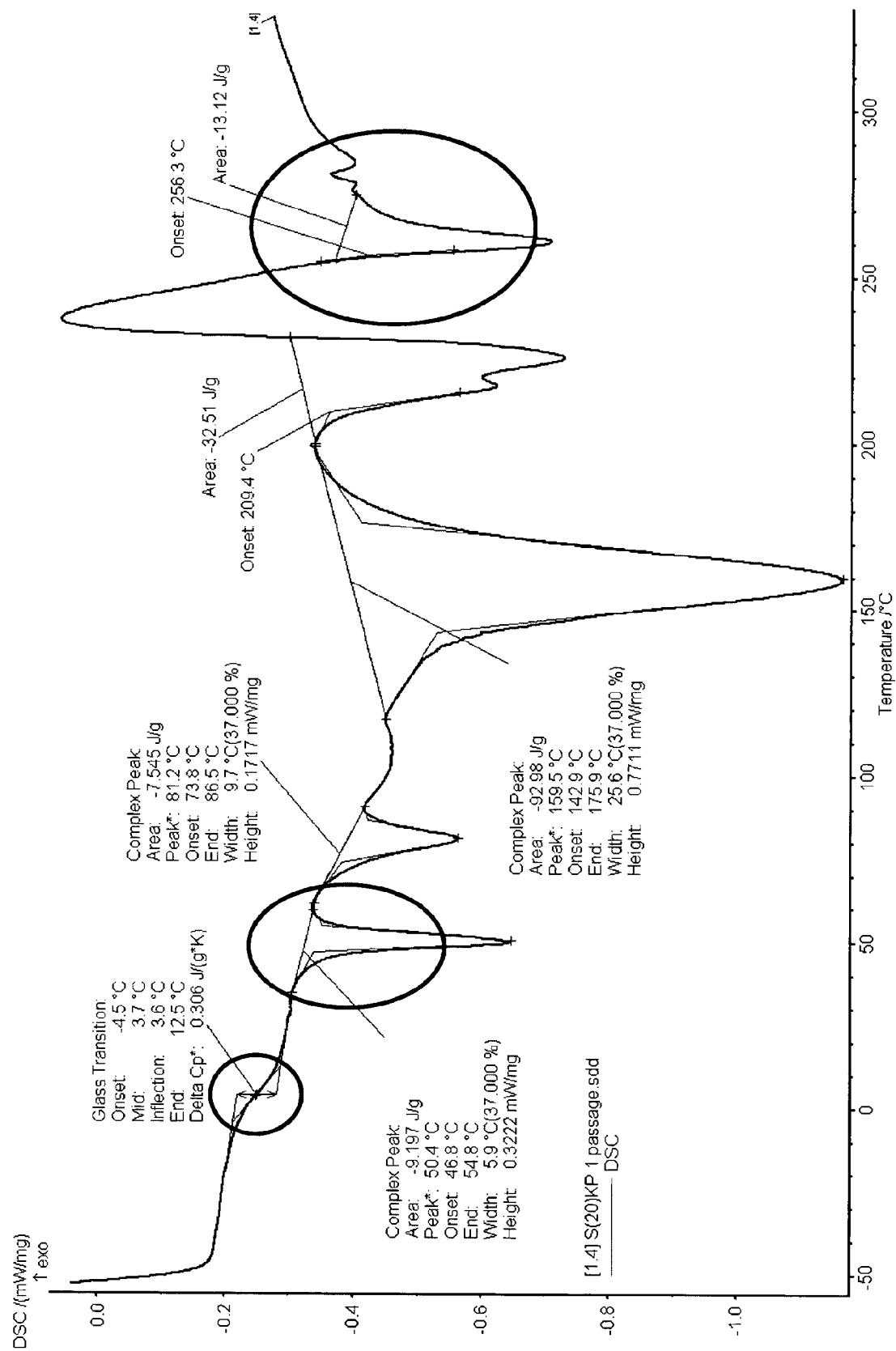
FIG. 12 is a DSC thermogram for sample C ($KH_2PO_4$/$K_2HPO_4$/sucrose).

Interpretation of DSC Data (Part 1):

The degree of crystallinity of the salt(s) in the coating of the present invention was determined based on the heat of crystallization of peaks measured for samples A, B and C. The heat of crystallization will depend on the amount of crystalline material present in the sample. Interpretation of thermogram of these three samples are shown in FIGS. 10, 11 and 12. The crystalline melting point (onset temperature) and the heat of crystallization (area in J per g) were determined for each crystallization peak observed and are reported in Table 16.

TABLE 16

| | Endothermic peaks (T ° C. and area in J/g) | | | |
|---|---|---|---|---|
| | $K_2HPO_4$ | | $KH_2PO_4$ | |
| sample | T ° C. | *Area in J/g (K2HPO4) | T ° C. | *Area in J/g (KH2PO4) |
| A | | | 255.1 | −244.2 |
| B | 45.5 | −38.7 | | |
| C | 46.8 | −9.2 | 256.3 | −13.1 |

*area corresponds to heat of crystallization

For $KH_2PO_4$, a crystalline melting point with onset T° C.=255° C. and heat of crystallization −244.2 J/g was measured.

For $K_2HPO_4$, a crystalline melting point with onset T° C.=45° C. and heat of crystallization −38 J/g was measured.

For the $KH_2PO_4$/$K_2HPO_4$/sucrose mixture,
- a peak was measured at 256.3° C. i.e. in the same T° C. range as that of $KH_2PO_4$ but its heat of crystallization −13.1 J/g was lower than that measured for $KH_2PO_4$ (sample A) and
- a peak was measured at 46.8° C., i.e. in the same T° C. range as that of $K_2HPO_4$ but its heat of crystallization 9.2 J/g was lower than that measured for $K_2HPO_4$ (sample B)

Taking into account the quantity of each phosphate salt present in the mixture, e.g. 35 wt % $KH_2PO_4$ and 45 wt % $K_2HPO_4$, and if both salts were 100% crystalline in the mixture, each salt should result in a heat of crystallization of
- 85.5 J/g for $KH_2PO_4$ (85.5 J/g=−244.2 J/g×35 wt % of $KH_2PO_4$) and
- 17.4 J/g for $K_2HPO_4$ (17.4 J/g=−38.7×45 wt % of $K_2HPO_4$)

However, the measured values for the coating (sample C) were much lower than estimated if both salts were 100% crystalline in the mixture
- 13.1 J/g for the peak with onset 256.3° C. corresponding to $KH_2PO_4$ and
- 9.2 J/g for the peak with onset 46.8° C. corresponding to $K_2HPO_4$.

The degree of crystallinity of each salt in the coating can hence be determined as following:
- 13.1/−85.5=15.3%, e.g. $KH_2PO_4$ is 15.3% crystalline and 84.7% amorphous
- 9.2/−17.4=52.9%, e.g. $K_2HPO_4$ is 52.9% crystalline and 47.1% amorphous In 1 g of the coating, there is 0.35 g of $KH_2PO_4$ and 0.45 g of $K_2HPO_4$
- 0.35 g×15.3% crystallinity=0.053 g of $KH_2PO_4$ in a crystalline form
- 0.45 g×52.9% crystallinity=0.238 g of $K_2HPO_4$ in a crystalline form Hence, the total amount of salts ($KH_2PO_4$+$K_2HPO_4$) in a crystalline form is 0.2916 g (0.053 g+0.238 g) per g of coating, so the crystallinity degree of the salts in the coating, once processed, is of 29.1%.

Figure 4:
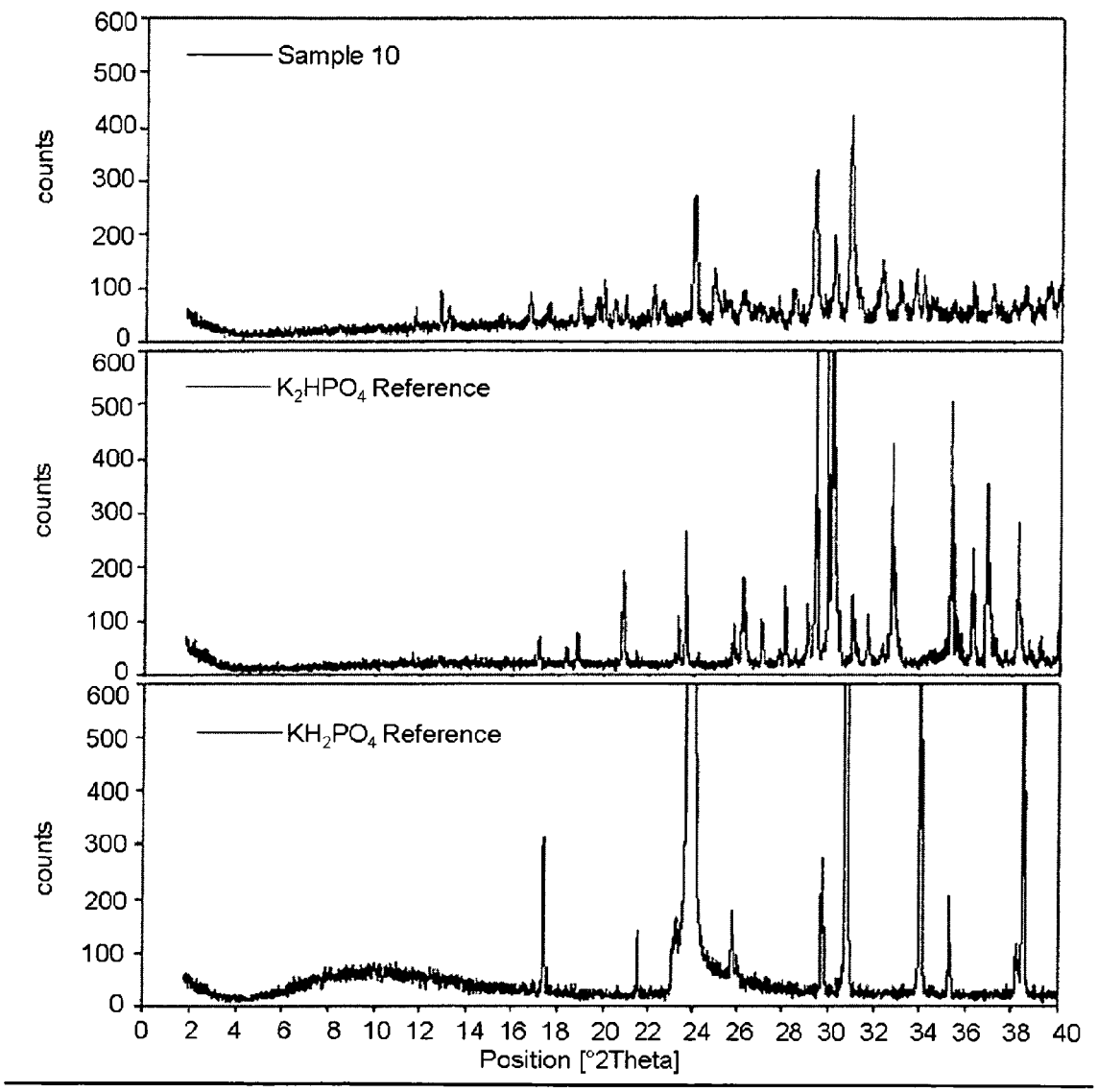
FIG. 4 is an X-ray diffraction pattern of coated dehydrated microorganism obtained by the liquid route, wherein the coating is a mixture of $K_2HPO_4$ (48% dry), $KH_2PO_4$ (35% dry), talc (17% dry) and 0% sucrose, co-processed by spray-coating (sample 10).
Figure 5:
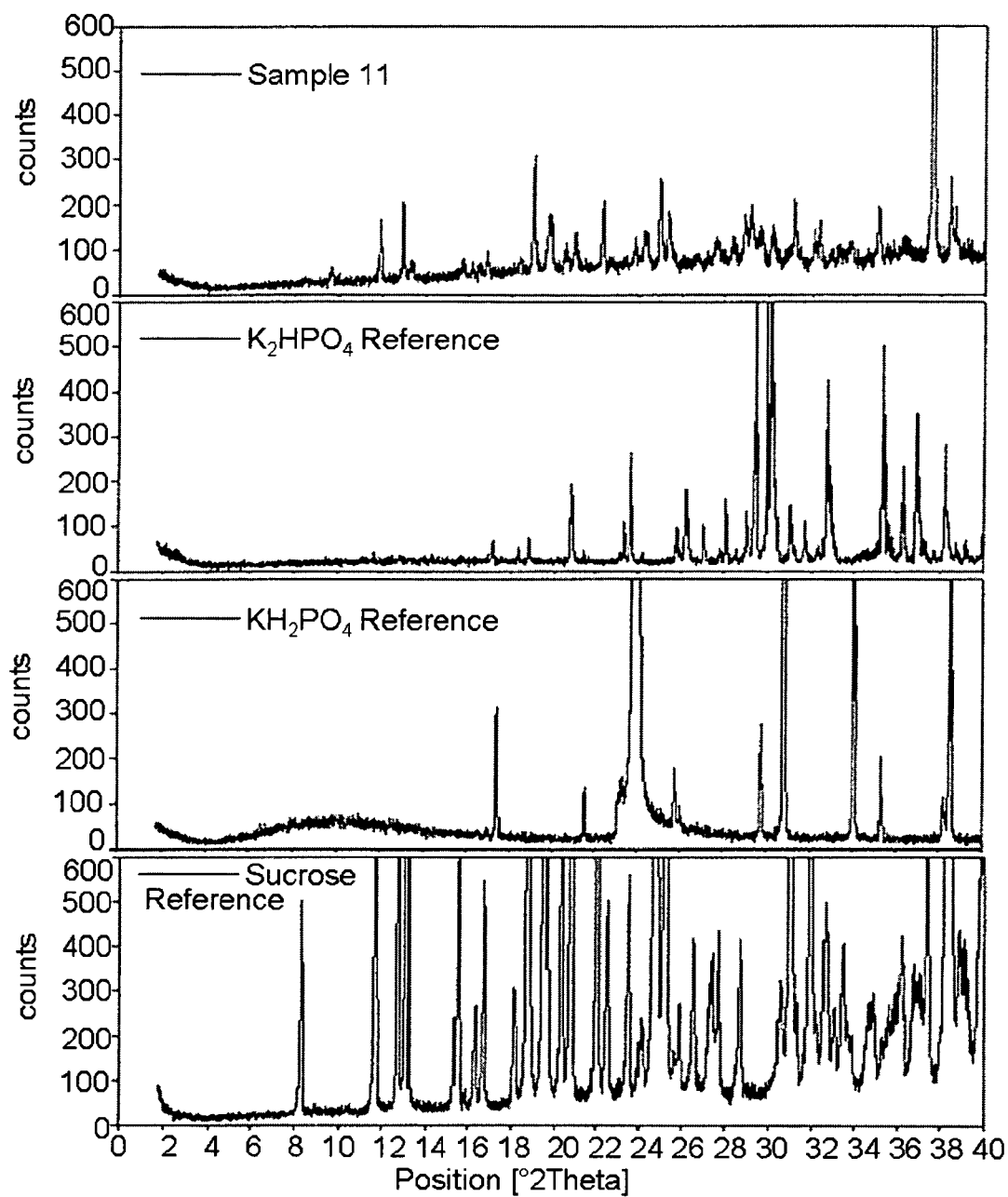
FIG. 5 is an X-ray diffraction pattern of coated dehydrated microorganism obtained by the liquid route, wherein the coating is a mixture $K_2HPO_4$ (40% dry), $KH_2PO_4$ (29% dry), talc (14% dry) and sucrose (17% dry), co-processed by spray-coating (sample 11).
Figure 6:
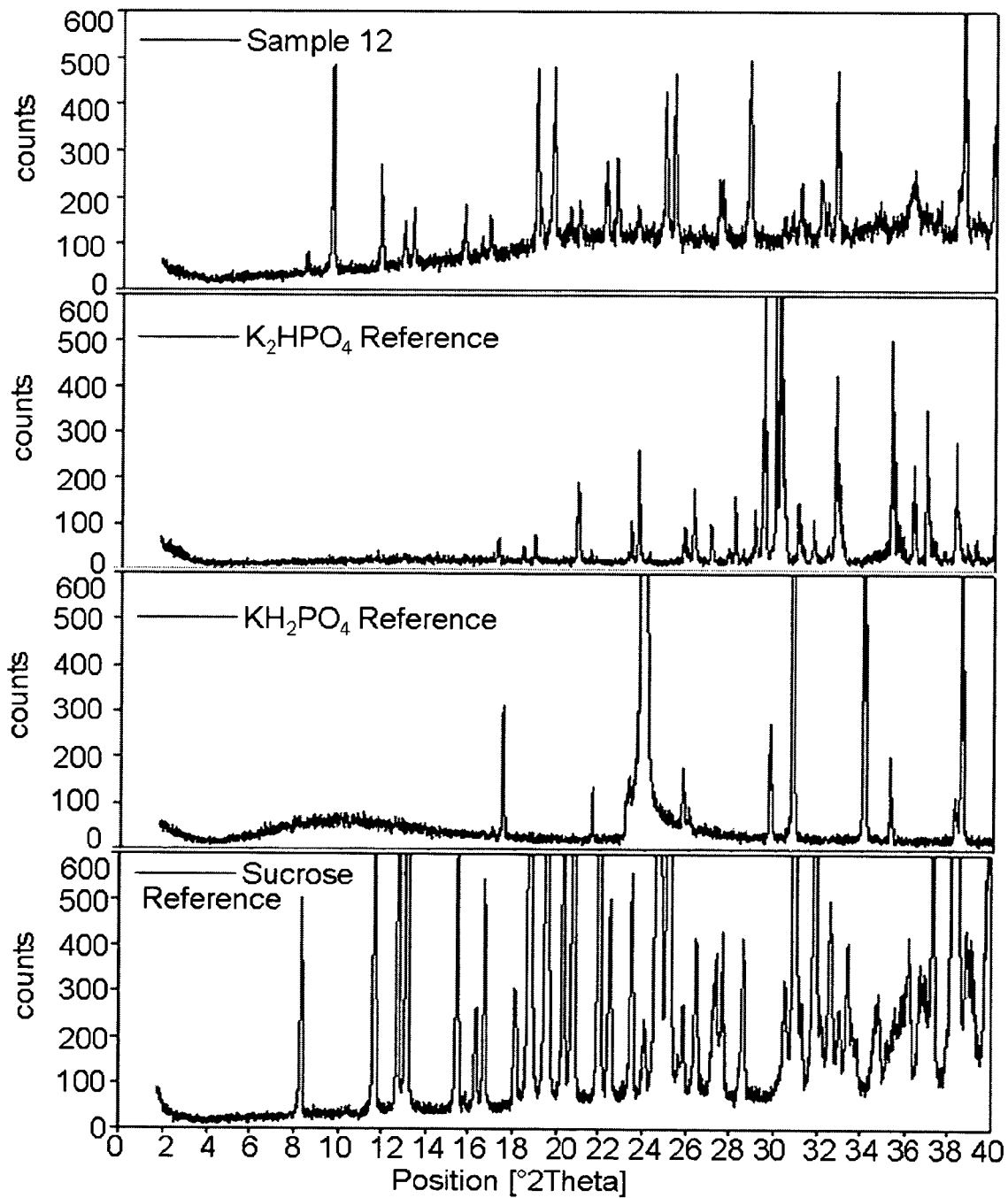
FIG. 6 is an X-ray diffraction pattern of a coated dehydrated microorganism obtained by the liquid route, wherein the coating is a mixture $K_2HPO_4$ (14% dry), $KH_2PO_4$ (11% dry), talc (22% dry) and sucrose (54% dry), co-processed by spray-coating (sample 12).
Figure 7:
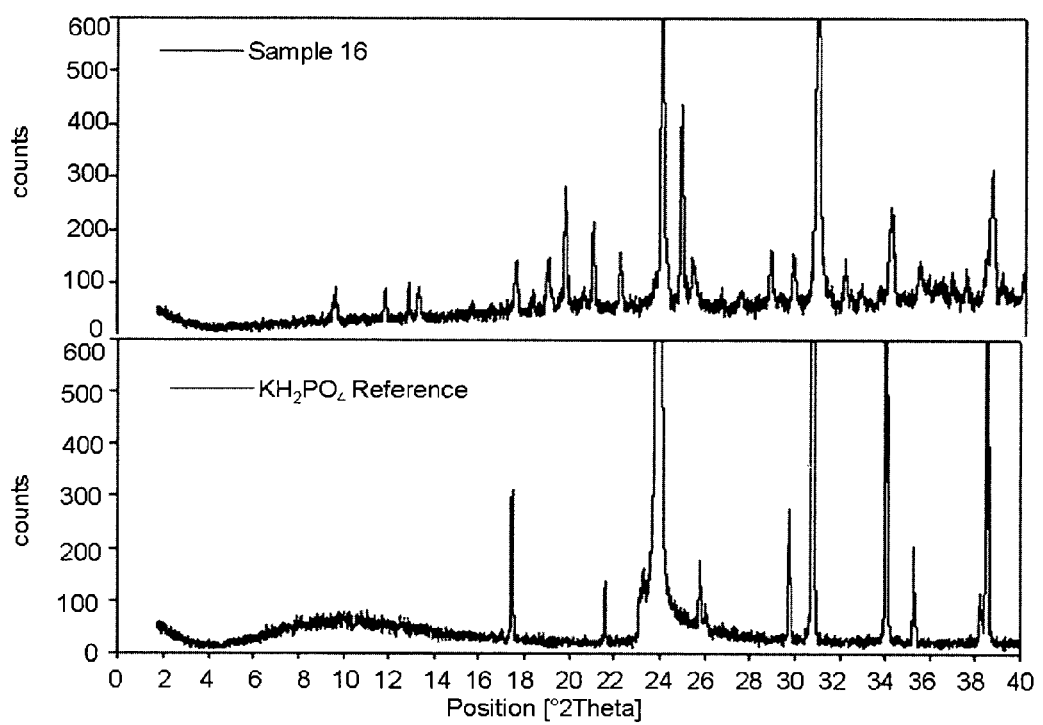
FIG. 7 is an X-ray diffraction pattern of a coated dehydrated microorganism obtained by the liquid route, wherein the coating is one non hygroscopic salt ($KH_2PO_4$) with talc processed by spray-coating (sample 16).
Figure 8:
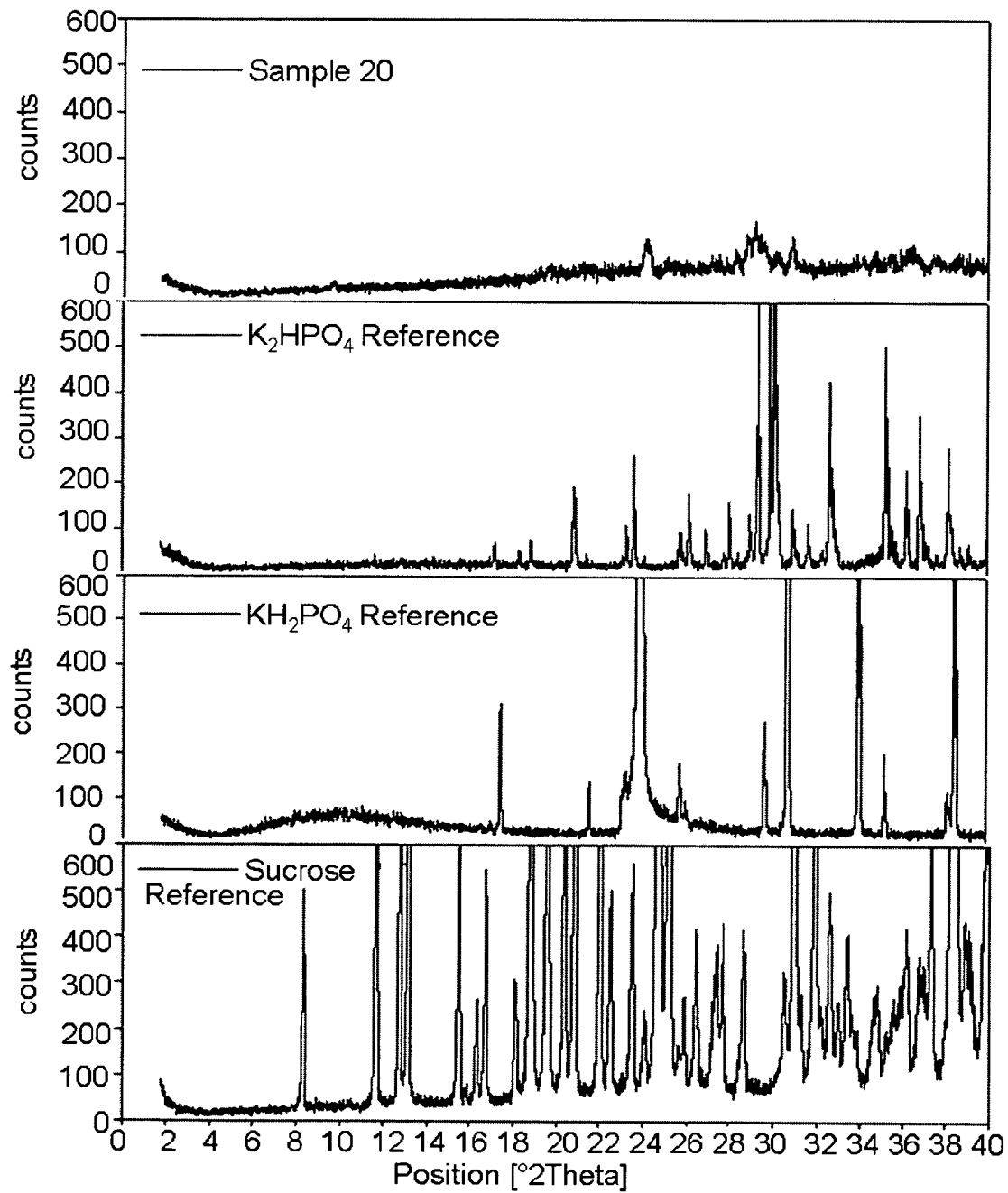
FIG. 8 is an X-ray diffraction pattern of a coated dehydrated microorganism obtained by the solid route, wherein the coating mixture is $K_2HPO_4$ (40% dry), $KH_2PO_4$ (29% dry), talc (14% dry) and sucrose (17% dry), co-processed by spray-coating (sample 20).
Figure 9:
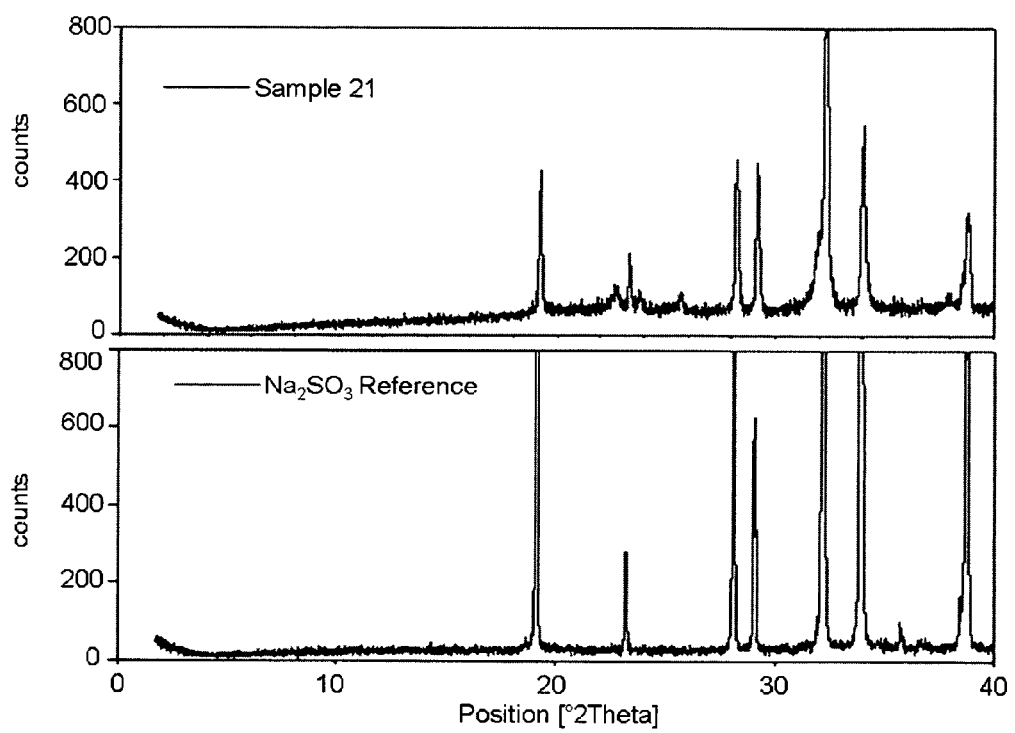
FIG. 9 is an X-ray diffraction pattern of a coated dehydrated microorganism obtained by the solid route, wherein the coating mixture is $Na_2SO_4$, co-processed by spray-coating (sample 21).

Interpretation of DSC Data (Part 2):

In addition, a glass transition temperature was measured for the sample C (35% KH2PO4, 45% K2HPO4 and 20% sucrose), as shown from FIG. 4. The presence of a Tg implies the presence of amorphous structure for the coating, validating the above approach using the heat of crystallization.

Conclusion from DSC data interpretation: a semi-crystalline structure was identified for fluid-bed dried sample C composition with a glass transition temperature. The degree of crystallinity of the salt(s) in the coating has been quantified to around 29%.

Example 12

Water Vapor Sorption Isotherm

Preparation of Samples:

Coated dehydrated microorganisms were produced with various coatings following the process according to the invention. These coatings were the equivalent to the ones described in table 1, "1st coating", of sample references no 10, 11, 13, 14, 15, 16, 23, 24, 25, 26, 27 and 28.

The coating was applied either on the dehydrated microorganism (labelled "+cells") or directly on the core in the absence of the dehydrated microorganism (labelled "−cells"). The amount of coating applied was 30 wt %. The process parameters were:

| Process parameters | Values |
|---|---|
| Step-up | Bottom spray |
| Nozzle | 1.2 mm |
| Inlet temperature | 65-70° C. |
| Product temperature | 55° C. |
| Atomization pressure | 2-2.5 bars |
| Air Flow | 120-200 m3/h |

Method:

In order to generate the sorption isotherms, each of the different samples were placed in a series of glass dessicators, each containing saturated salt solutions of certain salts, in order to adjust the samples to relative humidities (% RH) of 11.3%, 22.5%, 32.8%, 43% and 75%. Table 17 summarizes the salts used to achieve the targeted relative humidity at 25° C.

TABLE 17

| Salt | LiCl | $KCH_2CO_2$ | $MgCl_2$ | $K_2CO_3$ | NaCl |
|---|---|---|---|---|---|
| % RH (25° C.) | 11.3% | 22.5% | 32.8% | 43% | 75% |

The glass dessicator containing the samples were kept at constant temperature, e.g. 25° C. Each sample was weighed at regular interval (t). The Moisture Uptake Rate $MUR_{(t)}$ was determinate for each measurement according to the equation 1 (previously described in example 9) and an water vapour sorption isotherm was drawn (MUR $(_t)$=f (t), were MUR (t) represent the percentage of the water uptake as measured by % weight gain of the sample at the time of measurement.

Brief Explanation of the Figures

Figure 13:
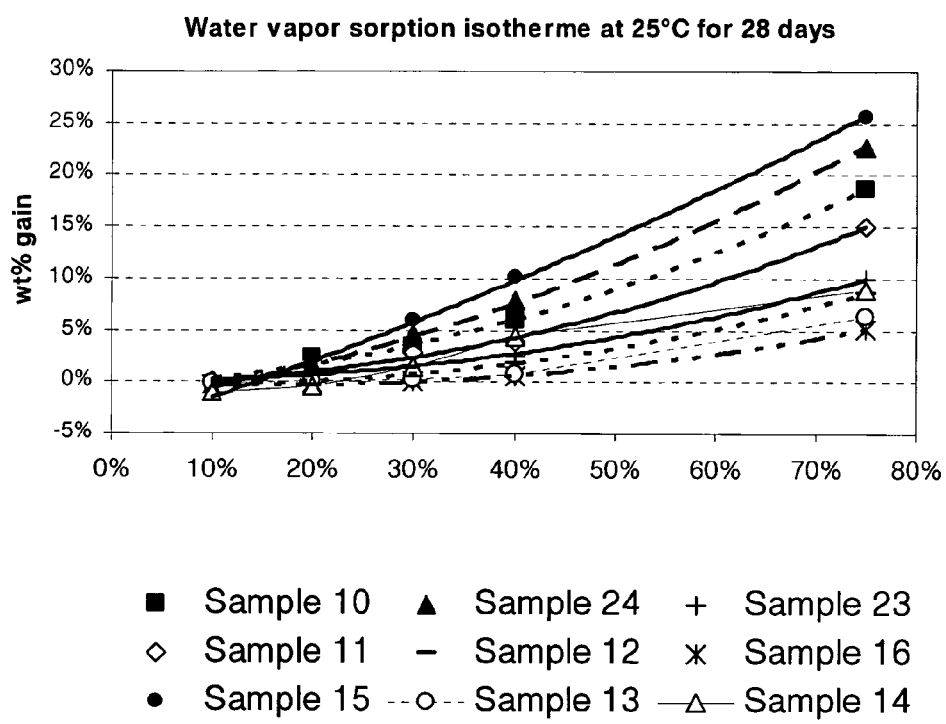
FIG. 13 is a water vapor sorption isotherm at 25° C. for dehydrated microorganisms surrounded by a coating comprising different composition, exposed to 0-75% RH at 25° C. at 28 days. All are fluid-bed dried NCFM surrounded by a coating of: Sample 10: $K_2HPO_4$ (48% dry), $KH_2PO_4$ (35% dry), sucrose (0% dry), talc (17% dry). Sample 11: $K_2HPO_4$ (40% dry), $KH_2PO_4$ (29% dry), sucrose (17% dry), talc (14% dry). Sample 12: $K_2HPO_4$ (14% dry), $KH_2PO_4$ (11% dry), sucrose (54% dry), talc (22% dry). Sample 13: $Na_2SO_4$. Sample 14: $MgSO_4$. Sample 15: $K_2HPO_4$ (83% dry), talc (17% dry). Sample 16: $KH_2PO_4$ (83% dry), talc (17% dry). Sample 23: $K_2HPO_4$ (23% dry), $KH_2PO_4$ (60% dry), talc (17% dry). Sample 24: $K_2HPO_4$ (19% dry), $KH_2PO_4$ (15% dry), sucrose (52% dry), talc (14% dry).
Figure 14:
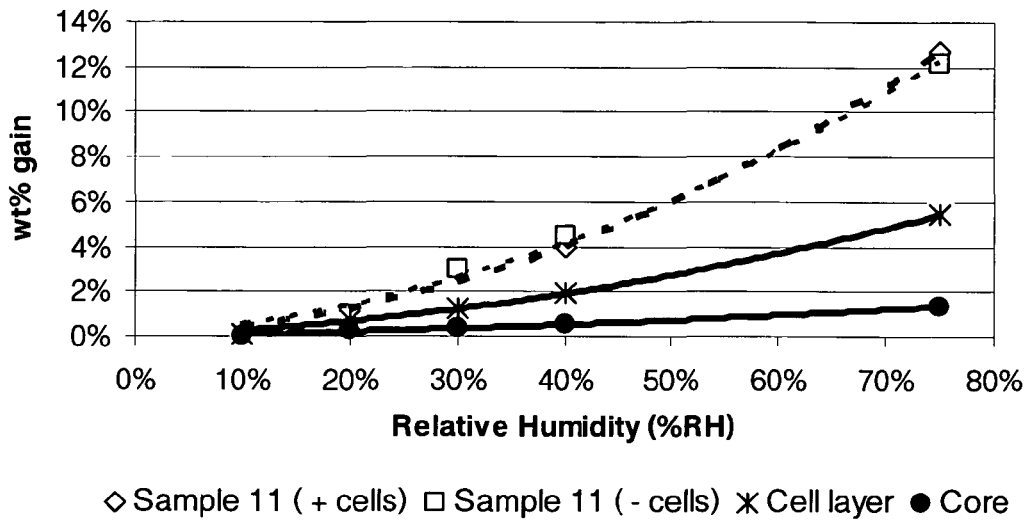
FIG. 14 is a water vapor sorption isotherm for uncoated particles (cores; core+dehydrated microorganism) and coated particles (core+salt coating; coated deshydrated microorganisms) with salt composition corresponding to sample 11 exposed to 0-75% RH at 25° C. at 28 days. Coating of sample 11: $K_2HPO_4$ (40% dry), $KH_2PO_4$ (29% dry), sucrose (17% dry), talc (14% dry).
Figure 15:
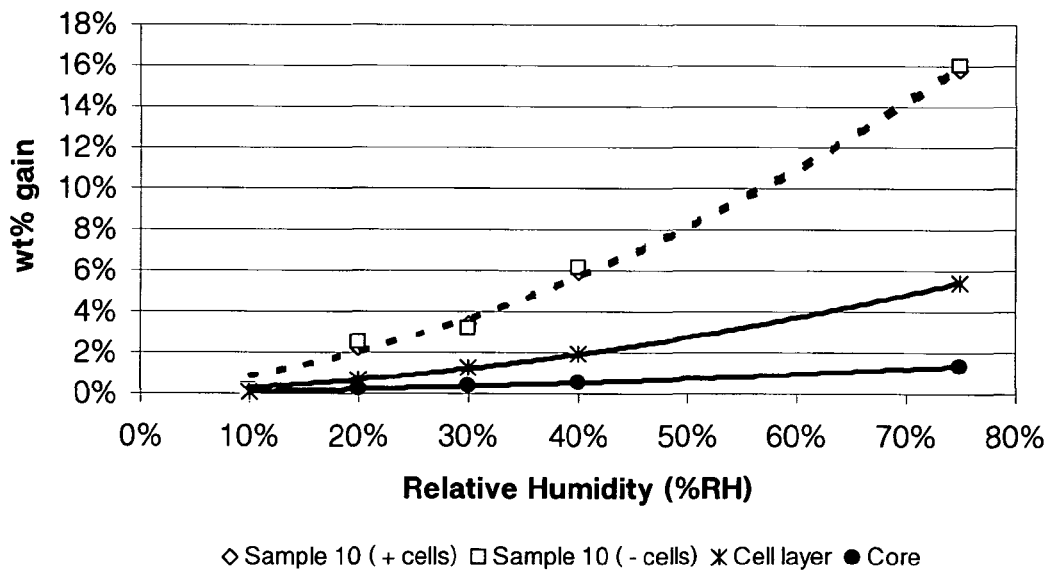
FIG. 15 is a water wapor sorption isotherm for uncoated particles (cores; core+dehydrated microorganism) and coated particles (core+salt coating; coated deshydrated microorganisms) with salt composition corresponding to sample 10 exposed to 0-75% RH at 25° C. at 28 days. Coating of sample 10: $K_2HPO_4$ (48% dry), $KH_2PO_4$ (35% dry), sucrose (0% dry), talc (17% dry)
Figure 16:
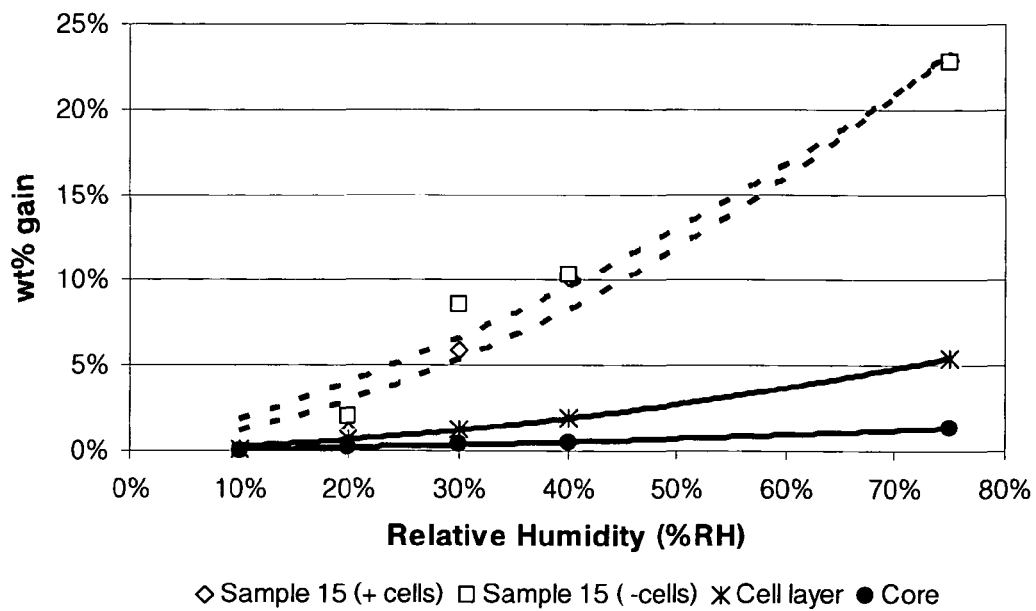
FIG. 16 is a water vapor sorption isotherm for uncoated particles (cores; core+dehydrated microorganism) and coated particles (core+salt coating; coated deshydrated microorganisms) with salt composition corresponding to sample 15 exposed to 0-75% RH at 25° C. at 28 days. Coating of sample 15: $K_2HPO_4$ (83% dry), talc (17% dry).
Figure 17:
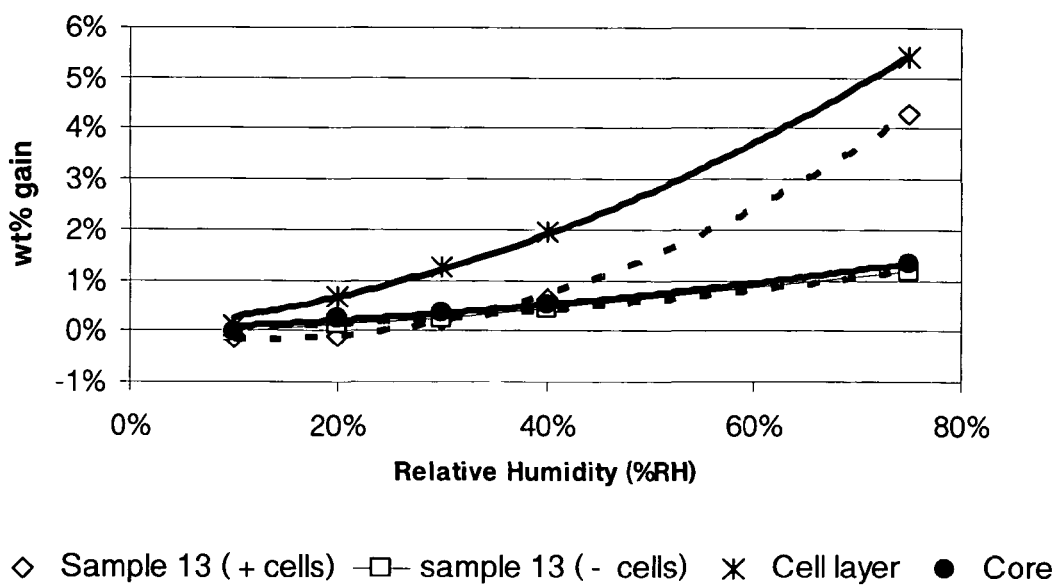
FIG. 17 is a water vapor sorption isotherm for uncoated particles (cores; core+dehydrated microorganism) and coated particles (core+salt coating; coated deshydrated microorganisms) with salt composition corresponding to sample 13 exposed to 0-75% RH at 25° C. at 28 days. Coating of sample 13: $Na_2SO_4$
Figure 18:
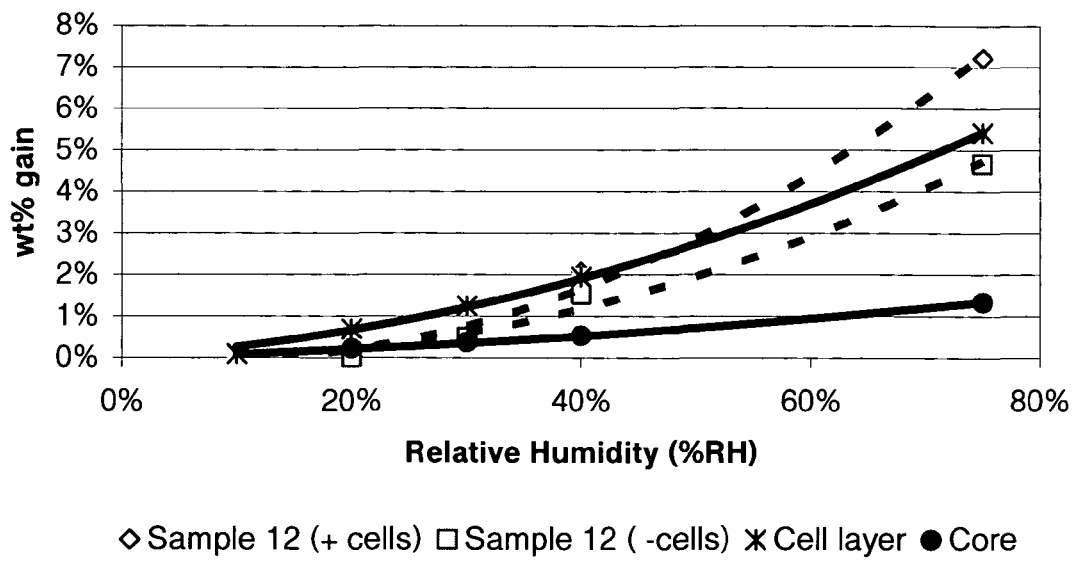
FIG. 18 is a water vapor sorption isotherm for uncoated particles (cores; core+dehydrated microorganism) and coated particles (core+salt coating; coated deshydrated microorganisms) with salt composition corresponding to sample 12 exposed to 0-75% RH at 25° C. at 28 days. Coating of sample 12: $K_2HPO_4$ (14% dry), $KH_2PO_4$ (11% dry), sucrose (54% dry), talc (22% dry).

FIG. 13 is a water vapor sorption isotherm at 25° C. for microorganisms coated with different salt coating compositions, exposed to relative humidity conditions ranging from 11.3%, 22.5%, 32.8%, 43% and 75% RH at 25° C. for 28 days.

FIGS. 14 to 19 concern water wapor sorption isotherms at 25° C. for particles including coated dehydrated microorganism exposed to various relative humidity conditions ranging from 11.3%, 22.5%, 32.8%, 43% and 75% RH for 28 days.

Figure 19:
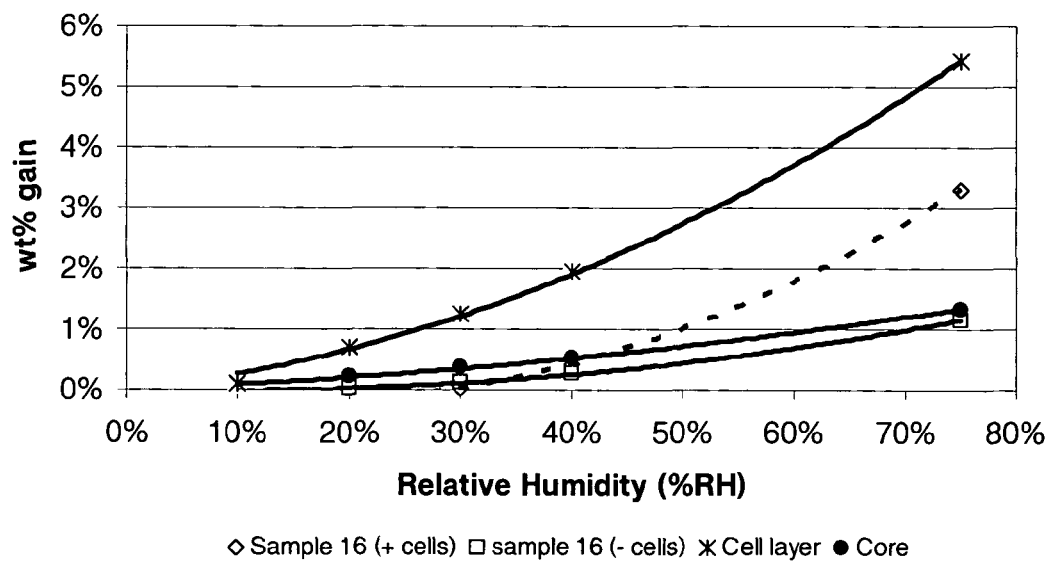
FIG. 19 is a water vapor sorption isotherm for uncoated particles (cores; core+dehydrated microorganism) and coated particles (core+salt coating; coated deshydrated microorganisms) with salt composition corresponding to sample 16 exposed to 0-75% RH at 25° C. at 28 days. Coating of sample 16: $KH_2PO_4$ (83% dry), talc (17% dry)

The particles are composed of:
the core only (●)
the core+the cell layer (*)—referred as "reference sample"
the core+the salt coating ( )
the core+cell layer+salt coating (◇)—referred as "product" or coated dehydrated microorganism The salt coatings were the ones described as 1st coating in table 1, i.e. sample 11 (FIG. 14), sample 10 (FIG. 15), sample 15 (FIG. 16), sample 13 (FIG. 17), sample 12 (FIG. 18), sample 16 (FIG. 19).

Data Interpretation (FIG. 13, Table 18 and Table 19):

The water sorption curves of the water vapor sorption isotherms allow a quantification of the effect of humidity on the moisture content of the coated dehydrated microorganisms. The Moisture Uptake Rate of the coated dehydrated microorganism or "product" was measured at 25° C., 75% RH at 2, 7 and 28 days days (Table 18). The MUR values presented in Table 19 were calculated for the coating according to equation 2.

$$MUR \text{ dehydrated coated microorganism}(t) \text{ in \%}=(mt-mt0)/mt0 \qquad \text{Equation 2:}$$

MUR (t): percentage of water uptake by dehydrated coated microorganisms at time T mt0: initial mass of dehydrated coated microorganism sample mt: mass of dehydrated coated microorganism at the time of measurement

TABLE 18

Moisture uptake rate (MUR) of the coated dehydrated microorganism at 75% RH, 25° C. at 2, 7 and 28 days
(% moisture of the coated dehydrated microorganism weight)

|  | 2 days | 7 days | 28 days |
|---|---|---|---|
| Sample 25 | 10% | 19% | 39% |
| Sample 15 | 8% | 17% | 26% |
| Sample 10 | 6% | 11% | 19% |
| Sample 11 | 5% | 9% | 15% |
| Sample 14 | 5% | 7% | 9% |
| Sample 23 | 3% | 5% | 10% |
| Sample 24 | 3% | 5% | 8% |
| Sample 13 | 0.6% | 2% | 6% |
| Sample 16 | 0.5% | 2% | 5% |

The results from Table 18 show a big difference in how much water is absorbed by the coated dehydrated microorganism, depending on the salt coating used. Samples 25, 15, 10, 11 are highly hygroscopic, absorbing between 9 wt % and 19 wt % of moisture per weight of the coated dehydrated microorganism. Sample 25 (MgCl$_2$) and sample 15 (K$_2$HPO$_4$) are the most hygroscopic. In addition, the water sorption profile in FIG. 13 shows a gradual increase in water content, which is characteristic of an amorphous or partially amorphous structure. In contrast, samples previously shown to offer little protection to the microorganism, e.g. sample 13 (Na$_2$SO4 layer (e.g. the coated dehydrated microorganisms) absorbs a greater amount of moisture compared to particules without the cell layer. This results shows that if the coating allows moisture to pass, the underlaying material will absorb greater amount of moisture. This is seen for samples containing the cell layer when the coating contains less than 25% of hygroscopic salts (sample 12) or do not contain any hygroscopic salts but non-hygroscopic salt instead (samples 13 and 16). These samples do not maintain cell viability under stressfull conditions.

Example 13

The Effect of pH of the Salt Coating on the Survival of the Coated Dehydrated *L. acidophilus* NCFM Results from the effect of pH of the salt coating on the survival of the coated dehydrated *L. acidophilus* NCFM are presented in Table 20.

iii) after heat treatment (64° C./18 hrs) with LOG loss for viable *L. acidophilus* NCFM reduced from >5.0 to 0.6 iv) storage in maltodextrine Aw=0.4 (37° C./9 days) with an increase in the recovery of viable *L. acidophilus* NCFM from 1% to 44%.

The hygrosocpicity of $KH_2PO_4$ coating with pH adjusted to 6.5 could be dramatically increased with moisture uptake of the coated dehydrated microorganism going from 1.3% prior to pH adjustement to 12.8 wt % moisture absorbed after pH adjustement with NaOH (conditions: 75% RH, 25° C., 6 days). These results showed that by pH adjustment it was possible to obtain a coating suitable by transformation of the non-hygroscopic nature into a hygroscopic one, hereby enabling stabilization of *L. acidophilus* NCFM in various stress conditions.

TABLE 20

| sample | 1st coating | pH* | Process survival % | Stability (14 days >30° C., dry) | Viability loss (log), heat (64° C./18 hrs) | % recovery (9 days, 37° C., aw 0.4) | MUR coated dehydrated microoroganisms (75% RH, 25° C., 6 days) |
|---|---|---|---|---|---|---|---|
| 15 | $K_2HPO_4$ | 8.0 | 65% | 7% | >5.3 | 2% | 12.8% |
| 27 | $K_2HPO_4$ and pH adjusted | 6.5 | 90% | 83% | 0.6 | Not measured | 11.6% |
| 16 | $KH_2PO_4$ | 5.0 | 47% | 2% | >5.0 | 1% | 1.3% |
| 28 | $KH_2PO_4$ and pH adjusted | 6.5 | 100% | 95% | 0.6 | 44% | 12.8% |

*pH of 10% solution of coated dehydrated microorganisms in water $K_2HPO_4$ is an alkaline salt and the pH of the $K_2HPO_4$ solution prior to coating was adjusted to a pH=6.5 using lactic acid. This resulted in a reduction of pH of the coated dehydrated microorganisms from pH 8 to pH 6.5 when measured as 10 wt % solution of the coated dehydrated microorganism in water. A significant improvement in the resistance of *L. acidophilus* NCFM was observed:
 i) during fluid-bed coating with process survival for *L. acidophilus* NCFM raised from 65% to 90%,
 ii) after 14 days of storage at 37° C. in dry conditions with recovery of viable *L. acidophilus* NCFM increased from 7% to 83%,
 iii) after heat treatment (64° C./18 hrs) with LOG loss for *L. acidophilus* NCFM reduced from more than 5.3 to 0.6.

$K_2HPO_4$ coating with pH adjusted to 6.5 remained hygroscopic with a moisture uptake for the coated dehydrated microorganism of 12.8 wt % moisture absorbed prior to pH adjustement and 11.6 wt % moisture absorbed after pH adjustement. (Conditions: 75% RH, 25° C., 6 days).

These results demonstrate that it is needed to have the pH of the coating compatible with the viability of the microorganism.

$KH_2PO_4$ is an acid salt and the pH of the $KH_2PO_4$ solution prior to coating was adjusted to pH 6.5 using Sodium Hydroxide (NaOH). This resulted in an increase of pH from pH 5.0 to pH 6.5 when measured after suspended the coated dehydrated microorganism into 10 wt % of water. A significant reduction in the viability loss of *L. acidophilus* NCFM was observed:
 i) during fluid-bed coating with process survival of *L. acidophilus* NCFM was raised from 47% to 100%,
 ii) after 14 days of storage at 30° C. in dry conditions with an increase in the recovery of viable *L. acidophilus* NCFM from 2% to 95%.

Example 14

Solid Route

The viability of dehydrated *L. acidophilus* NCFM in freeze-dried form and in the coated particles (solid route) has been studied in the conditions described in example 6.

The bacteria preparation was mixed into the maltodextrin powder (aw=0.4) at a ratio of 10% wt of coated bacteria and 90% wt of maltodextrin powder. The vials were kept at 30° C. in an incubator. After 2 months storage at 30° C., a vial of the mixture was analyzed for its content of viable cells by standard plating methods. The results are listed in Table 21. The concentration of viable cells is expressed as CFU/g and as a percentage of the concentration of each samples at T=0.

TABLE 21

| Sample | T = 0 | 2 months | % survival | Protection factor over control |
|---|---|---|---|---|
| 2 | 2.52E+11 | 9.78E+08 | 0.4% | n.a. |
| 20 | 1.84E+11 | 5.30E+10 | 29% | 74 | n.a. non applicable (control)
* Protection factor calculated at 2 month-storage, 30° C.

The coating of the invention (sample 20: $K_2HPO_4$ (40% dry), $KH_2PO_4$ (29% dry), talc (14% dry) and sucrose (17% dry)) applied onto freeze-dried *L. acidophilus* NCFM powder is very effective in maintaining the viability of *L. acidophilus* NCFM at intermediate moisture. The effectiveness of the coating of the invention in stabilizing dehydrated microorganisms was previously demonstrated for the coated dehydrated microorganism prepared according to the liquid route. It is now demonstrated in this example that the coating of the invention is also effective for coated dehydrated microorganism prepared according to the solid route.

Example 15

Stability in Infant Formula

The viability of *L. acidophilus* NCFM in freeze-dried form (sample 2) and in the coated dehydrated microorganisms according to the present invention (sample 11) has been studied in the following conditions:

The test samples were blended into commercial "Good Sense Gentle Plus" Instant Baby Formula from Nestle (Aw=0.157) at a ratio of test sample to baby formula powder of 1:10. The mixtures were then divided into 10 g samples in separate sealed hermetic sachets. The sachets were kept in an incubator at 30° C. At time 0 and after 1, 3, 6 and 9 months of storage at 30° C., a sachet of each blend was analysed for the content of viable cells, by standard plating methods.

TABLE 22

| Sample | Aw T = 0 | T = 0 | 1 Months | 3 Months | 6 Months | 9 Months | *Protection factor over control (2) |
|---|---|---|---|---|---|---|---|
| 2 | 0.17 | $2.7^{E+10}$ (100%) | $1.2^{E+10}$ (43.6%) | $1.1^{E+10}$ (39.6%) | $1.0^{E+10}$ (36.6%) | $1.7^{E+09}$ (6%) | n.a. |
| 11 | 0.15 | $1.4^{E+09}$ (100%) | $1.45^{E+09}$ (104%) | $1.47^{E+09}$ (105%) | $1.2^{E+09}$ (85%) | $1.2^{E+08}$ (86%) | 14 | n.a. non applicable (control)
*Protection factor calculated at 9 month-storage, 30° C.

The results from Table 22 show that the presence of the coating according to the invention (samples 11) improves stability over uncoated dehydrated bacteria (sample 2).

The invention claimed is:

1. A coated dehydrated microorganism comprising a dehydrated microorganism surrounded by at least one coating, said coating contacting the microorganism and comprising by dry weight at least 25% of hygroscopic salt(s), wherein the hygroscopic salt(s) has/have a Moisture Uptake Rate (MUR) of at least 20% w/w at 25° C. at 75% RH after 7 days and is selected from at least one hygroscopic salt from the group consisting of dipotassium phosphate ($K_2HPO_4$), disodium hydrogen phosphate anhydrous ($Na_2HPO_4$), sodium hexametaphosphate ($NaPO_3)_6$, sodium acetate anhydrous ($CH_3COONa$), magnesium nitrate ($Mg(NO_3)_2$), calcium bromide (CaBr), lithium bromide (LiBr), calcium chloride ($CaCl_2$), magnesium chloride ($MgCl_2$), lithium chloride (LiCl), phosphorus pentoxide ($P_4O_{10}$), disodium hydrogen phosphate dihydrate ($Na_2HPO_4.2H_2O$), disodium hydrogen phosphate heptahydrate ($Na_2HPO_4.7H_2O$), ammonium acetate ($CH_3COONH_3$), calcium acetate ($CH_3COO)_2Ca$, potassium acetate ($CH_3COOK$), potassium carbonate ($K_2CO_3$), sodium carbonate ($Na_2CO_3$), sodium formate ($NaCHO_2$), potassium citrate monohydrate ($K_3C_6H_5O_7.H_2O$), Sodium citrate pentahydrate ($C_6H_5Na_3O_7.5H_2O$) and mixtures thereof, wherein the microorganism is a bacteria, and wherein the pH of the coating is from 5.5 to 7.9 and improves the viability or the stability of the bacteria over the uncoated bacteria.

2. The coated dehydrated microorganism according to claim 1, wherein said coating comprises by dry weight at least 28% of the hygroscopic salt or mixture thereof.

3. The coated dehydrated microorganism according to claim 1, wherein the coating consists of 100% by dry weight of the hygroscopic salt(s).

4. The coated dehydrated microorganism according to claim 1, wherein the hygroscopic salt(s) has/have a MUR of at least 30% w/w at 25° C. at 75% RH after 7 days.

5. The coated dehydrated microorganism according to claim 1, wherein the coating also comprises by dry weight from 0 to 60% of a non hygroscopic salt or mixture thereof.

6. The coated dehydrated microorganism according to claim 1, wherein the coating also comprises by dry weight from 0 to 70% other ingredient(s).

7. The coated dehydrated microorganism according to claim 1, wherein the coating comprises dipotassium phosphate $K_2HPO_4$ as the hygroscopic salt or comprises a mixture of the hygroscopic salts including dipotassium phosphate $K_2HPO_4$.

8. The coated dehydrated microorganism according to claim 5, wherein the non-hygroscopic salt is selected from the group consisting of monopotassium phosphate ($KH_2PO_4$), sodium acetate tri hydrate ($CH_3COONa.3H_2O$), calcium sulphate dihydrate ($CaSO_3.2H_2O$), sodium sulphate ($Na_2SO_4$), magnesium sulphate ($MgSO_4$), potassium sulphate ($K_2SO_4$), sodium chloride (NaCl), potassium chloride (KCl), calcium carbonate ($CaCO_3$), calcium lactate (($CH_3CHOHCOO)_2Ca$), calcium citrate tetrahydrate (($Ca_3C_6H_5O_7)_2.4H_2O$), sodium citrate dihydrate ($HOC(COONa)(CH_2COONa)_2.2H_2O$), and mixtures thereof.

9. The coated dehydrated microorganism according to claim 6, wherein the other ingredient(s) can be selected from the group of polyhydroxy compounds, anti-sticking agents, compounds having health and/or nutritional benefits, hydrocolloids, fillers, lubricants, binders, acids, alkali, hydrophobic species, polymers, and mixtures thereof.

10. The coated dehydrated microorganism according to claim 1, wherein the coating comprises $K_2HPO_4$ (83 wt % dry) and talc (17 wt % dry) or $K_2HPO_4$ (30 wt % dry), sodium acetate trihydrate (30 wt % dry), sucrose (17 wt % dry) and talc (14 wt % dry).

11. The coated dehydrated microorganism according to claim 1, wherein the coating comprises at least $K_2HPO_4$ and $KH_2PO_4$.

12. The coated dehydrated microorganism according to claim 1, which has at least one outercoating.

13. The coated dehydrated microorganism according to claim 1, wherein the salt(s) in the coating has/have a salt crystallinity degree of up to 60% once applied onto the dehydrated microorganism.

14. The coated dehydrated microorganism according to claim 1, wherein the coating has a Moisture Uptake Rate of at least 15% at 25° C. and at 75% relative humidity (RH) after 7 days.

15. The coated dehydrated microorganism according to claim 1, wherein the coated dehydrated microorganism has a Moisture Uptake Rate of at least 8%, at 25° C. and at 75% relative humidity (RH) after 7 days.

16. The coated dehydrated microorganism according to claim 1, wherein the coating is in a quantity of at least 10% by weight of the coated dehydrated microorganism.

17. The coated dehydrated microorganism according to claim 1, which has a stability of minimum 40% survival upon storage from 15° C. to 40° C. for up to 2 years when stored in sealed conditions.

18. The coated dehydrated microorganism according to claim 1, which has a viability loss of <1.5 LOG upon 12 months storage at temperature from 15° C. to 40° C., in a feed product, a food product, a consumer healthcare product or an agri-product having a water activity (aw) greater than 0.10.

19. The coated dehydrated microorganism according to claim 1, which has a viability loss of <3 LOG upon 2 years storage at temperature from 15° C. to 40° C., in a feed product, a food product, a consumer healthcare product or an agri-product having an aw greater than 0.10.

20. The coated dehydrated microorganism according to claim 1, wherein the bacteria are probiotics or direct fed microbials (DFMs).

21. A method for the preparation of a food product, a feed product, a consumer healthcare product or an agri-product, wherein the coated dehydrated microorganism as defined in claim 1 is subsequently added to a food product, feed product, consumer healthcare product or agri-product.

22. A food product, a feed product, a consumer healthcare product or an agri-product comprising the coated dehydrated microorganism as defined in claim 1.

23. The coated dehydrated microorganism according to claim 11, wherein the coating is selected from the group consisting of:
   $K_2HPO_4$ (40 wt % dry), $KH_2PO_4$ (29 wt % dry), sucrose (17 wt % dry), and talc (14 wt % dry);
   $K_2HPO_4$ (48 wt % dry), $KH_2PO4$ (35 wt % dry), and talc (17 wt % dry); and
   $K_2HPO_4$ (63 wt % dry), $KH_2PO_4$ (20 wt % dry), and talc (17 wt % dry).

24. The coated dehydrated microorganism according to claim 12, wherein said outercoating comprises a compound selected from the group consisting of fats, fatty acids, emulsifiers, oils, waxes, resins, low permeability polymers, hydrocolloids, starches, cyclodextrines, polyols, cellulose, cellulose derivatives and mixtures thereof.

25. The coated dehydrated microorganism according to claim 16, wherein the coating is in a quantity of at least 30% by weight of the coated dehydrated microorganism.

26. A liquid coating composition for coating a dehydrated microorganism comprising at least 25% of a hygroscopic salt or mixture thereof by dry weight of dry solids within the composition, wherein the hygroscopic salt is selected from the group consisting of dipotassium phosphate ($K_2HPO_4$), disodium hydrogen phosphate anhydrous ($Na_2HPO_4$), sodium hexametaphosphate ($NaPO_3)_6$, sodium acetate anhydrous ($CH_3COONa$), magnesium nitrate ($Mg(NO_3)_2$), calcium bromide (CaBr), lithium bromide (LiBr), calcium chloride ($CaCl_2$), magnesium chloride ($MgCl_2$), lithium chloride (LiCl), phosphorus pentoxide ($P_4O_{10}$), disodium hydrogen phosphate dihydrate ($Na_2HPO_4.2H_2O$), disodium hydrogen phosphate heptahydrate ($Na_2HPO_4.7H_2O$), ammonium acetate ($CH_3COONH_3$), calcium acetate ($CH_3COO)_2Ca$, potassium acetate ($CH_3COOK$), potassium carbonate ($K_2CO_3$), sodium carbonate ($Na_2CO_3$), sodium formate ($NaCHO_2$), potassium citrate monohydrate ($K_3C_6H_5O_7.H_2O$), Sodium citrate pentahydrate ($C_6H_5Na_3O_7.5H_2O$) and mixtures thereof, wherein the microorganism is a bacteria, and wherein the pH of the coating, when the liquid coating is applied onto bacteria, is from 5.5 to 7.9 and said coating improves the viability or the stability of the bacteria over the uncoated bacteria.

27. A method for coating a dehydrated microorganism, said method comprising the steps of:
   (a) preparing a liquid coating composition comprising by dry weight at least 25% of hygroscopic salt(s), wherein said hygroscopic salt(s) has/have a MUR of at least 20% w/w at 25° C. at 75% RH after 7 days, and is selected from at least one hygroscopic salt from the group consisting of dipotassium phosphate ($K_2HPO_4$), disodium hydrogen phosphate anhydrous ($Na_2HPO_4$), sodium hexametaphosphate ($NaPO_3)_6$, sodium acetate anhydrous ($CH_3COONa$), magnesium nitrate ($Mg(NO_3)_2$), calcium bromide (CaBr), lithium bromide (LiBr), calcium chloride ($CaCl_2$), magnesium chloride ($MgCl_2$), lithium chloride (LiCl), phosphorus pentoxide ($P_4O_{10}$), disodium hydrogen phosphate dihydrate ($Na_2HPO_4.2H_2O$), disodium hydrogen phosphate heptahydrate ($Na_2HPO_4.7HO_2O$), ammonium acetate ($CH_3COONH_3$), calcium acetate ($CH_3COO)_2Ca$, potassium acetate ($CH_3COOK$), potassium carbonate ($K_2CO_3$), sodium carbonate ($Na_2CO_3$), sodium formate ($NaCHO_2$), potassium citrate monohydrate ($K_3C_6H_5O_7.H_2O$), Sodium citrate pentahydrate ($C_6H_5Na_3O_7.5H_2O$) and mixtures thereof, and
   (b) coating onto a dehydrated microorganism the liquid coating composition obtained after step (a) in order to obtain a coated dehydrated microorganism comprising a dehydrated microorganism surrounded by at least one coating, said coating comprising by dry weight at least 25% of the hygroscopic salt(s), wherein the microorganism is a bacteria, and wherein the pH of the coating is from 5.5 to 7.9 and wherein the coating improves the viability or the stability of the bacteria over the uncoated bacteria.

28. A method according to claim 27 further comprising a step (c):
   (c) coating the coated dehydrated microorganism obtained after step (b) with at least one outercoating comprising at least one compound selected from the group consisting of fats, fatty acids, emulsifiers, oils, waxes, resins, low permeability polymers, hydrocolloids, starches, cyclodextrines, polyols, cellulose, cellulose derivatives and mixtures thereof.

29. A method for protecting a dehydrated microorganism, said method comprising preparing a coated dehydrated microorganism by applying onto the dehydrated microorganism at least one liquid coating composition comprising by dry weight at least 25% of a hygroscopic salt or mixture of hygroscopic salts, wherein said hygroscopic salt(s) has/have a MUR of at least 20% w/w at 25° C. at 75% RH after 7 days and is selected from at least one hygroscopic salt from the group consisting of dipotassium phosphate ($K_2HPO_4$), disodium hydrogen phosphate anhydrous ($Na_2HPO_4$), sodium hexametaphosphate ($NaPO_3)_6$, sodium acetate anhydrous ($CH_3COONa$), magnesium nitrate ($Mg(NO_3)_2$), calcium bromide (CaBr), lithium bromide (LiBr), calcium chloride ($CaCl_2$), magnesium chloride ($MgCl_2$), lithium chloride (LiCl), phosphorus pentoxide ($P_4O_{10}$), disodium hydrogen phosphate dihydrate ($Na_2HPO_4.2H_2O$), disodium hydrogen phosphate heptahydrate ($Na_2HPO_4.7H_2O$), ammonium acetate ($CH_3COONH_3$), calcium acetate ($CH_3COO)_2Ca$, potassium acetate ($CH_3COOK$), potassium carbonate ($K_2CO_3$), sodium carbonate ($Na_2CO_3$), sodium formate (NaCHO$_2$), potassium citrate monohydrate ($K_3C_6H_5O_7 \cdot H_2O$), Sodium citrate pentahydrate ($C_6H_5Na_3O_7 \cdot 5H_2O$) and mixtures thereof, wherein the microorganism is a bacteria, and wherein the pH of the coating is from 5.5 to 7.9 and wherein the coating improves the viability or the stability of the bacteria over the uncoated bacteria.

30. A coated dehydrated microorganism obtainable by a method comprising the steps of:
    (a) preparing a liquid coating composition comprising by dry weight at least 25% of hygroscopic salt(s), wherein said hygroscopic salt(s) has/have a MUR of at least 20% w/w at 25° C. at 75% RH after 7 days and is selected from the group consisting of dipotassium phosphate ($K_2HPO_4$), disodium hydrogen phosphate anhydrous ($Na_2HPO_4$), sodium hexametaphosphate ($NaPO_3)_6$, sodium acetate anhydrous ($CH_3COONa$), magnesium nitrate ($Mg(NO_3)_2$), calcium bromide (CaBr), lithium bromide (LiBr), calcium chloride ($CaCl_2$), magnesium chloride ($MgCl_2$), lithium chloride (LiCl), phosphorus pentoxide ($P_4O_{10}$), disodium hydrogen phosphate dihydrate ($Na_2HPO_4 \cdot 2H_2O$), disodium hydrogen phosphate heptahydrate ($Na_2HPO_4 \cdot 7H_2O$), ammonium acetate ($CH_3COONH_3$), calcium acetate ($CH_3COO)_2Ca$, potassium acetate ($CH_3COOK$), potassium carbonate ($K_2CO_3$), sodium carbonate ($Na_2CO_3$), sodium formate ($NaCHO_2$), potassium citrate monohydrate ($K_3C_6H_5O_7 \cdot H_2O$), Sodium citrate pentahydrate ($C_6H_5Na_3O_7 \cdot 5H_2O$) and mixtures thereof, and
    (b) coating onto a dehydrated microorganism the liquid coating composition obtained after step (a), in order to obtain a coated dehydrated microorganism comprising a dehydrated microorganism surrounded by at least one coating, said coating comprising by dry weight at least 25% of the hygroscopic salt(s), wherein the microorganism is a bacteria, and wherein the pH of the coating is from 5.5 to 7.9, and wherein the coating improves the viability or the stability of the bacteria over the uncoated bacteria.

* * * * *